US009453050B2

(12) United States Patent
Kaminska-Kaczmarek et al.

(10) Patent No.: US 9,453,050 B2
(45) Date of Patent: Sep. 27, 2016

(54) COMPOSITIONS FOR TREATING GLIOMA

(71) Applicant: GLIA SP Z.O.O., Warsaw (PL)

(72) Inventors: Bozena Kaminska-Kaczmarek, Komorow (PL); Malgorzata Sielska, Karczew (PL); Pawel Wisniewski, Warsaw (PL); Aleksandra Ellert-Miklaszewska, Komorow (PL)

(73) Assignee: GLIA SP Z.O.O., Warsaw (PL)

( * ) Notice: Subject to any disclaimer, the term of this patent is extended or adjusted under 35 U.S.C. 154(b) by 0 days.

(21) Appl. No.: 14/280,095

(22) Filed: May 16, 2014

(65) Prior Publication Data

US 2014/0256628 A1  Sep. 11, 2014

Related U.S. Application Data

(63) Continuation of application No. PCT/IB2012/056533, filed on Nov. 18, 2012.

(60) Provisional application No. 61/583,745, filed on Jan. 6, 2012, provisional application No. 61/561,080, filed on Nov. 17, 2011.

(51) Int. Cl.
| | |
|---|---|
| *A61K 38/08* | (2006.01) |
| *A61K 38/12* | (2006.01) |
| *C07K 7/08* | (2006.01) |
| *C07K 14/52* | (2006.01) |
| *C07K 14/535* | (2006.01) |
| *C07K 14/715* | (2006.01) |
| *C07K 7/06* | (2006.01) |
| *C07K 7/64* | (2006.01) |
| *A61K 38/00* | (2006.01) |

(52) U.S. Cl.
CPC . *C07K 7/08* (2013.01); *C07K 7/06* (2013.01); *C07K 7/64* (2013.01); *C07K 14/52* (2013.01); *C07K 14/535* (2013.01); *C07K 14/715* (2013.01); *A61K 38/00* (2013.01)

(58) Field of Classification Search
CPC ............ C07K 7/06; C07K 7/08; C07K 7/52; C07K 7/64; C07K 14/52; C07K 14/535
See application file for complete search history.

(56) References Cited

U.S. PATENT DOCUMENTS

| | | | |
|---|---|---|---|
| 6,372,720 B1 | 4/2002 | Longmuir et al. | |
| 6,410,516 B1 | 6/2002 | Baltimore et al. | |
| 2002/0164667 A1* | 11/2002 | Alitalo ................... | C07K 14/71 435/7.23 |
| 2003/0108597 A1 | 6/2003 | Chancellor et al. | |
| 2004/0010116 A1 | 1/2004 | Ashkar | |
| 2005/0176667 A1 | 8/2005 | Vornlocher | |
| 2009/0130093 A1* | 5/2009 | Cohen ................. | C07K 16/2866 424/130.1 |

FOREIGN PATENT DOCUMENTS

| | | |
|---|---|---|
| EP | 0409091 A1 | 1/1991 |
| EP | 1002543 A1 | 5/2000 |
| WO | 9102063 A1 | 2/1991 |
| WO | 0038665 A2 | 7/2000 |
| WO | 0044404 A2 | 8/2000 |
| WO | 0174855 A2 | 10/2001 |
| WO | 2006119767 A2 | 11/2006 |
| WO | 2007035843 A2 | 3/2007 |
| WO | 2007084670 A2 | 7/2007 |
| WO | WO 2007/110631 * | 10/2007 |
| WO | 2008112659 A2 | 9/2008 |
| WO | 2009052286 A1 | 4/2009 |
| WO | 2009094172 A2 | 7/2009 |
| WO | 2010057596 A2 | 5/2010 |
| WO | 2010136168 A2 | 12/2010 |
| WO | 2011136828 A1 | 11/2011 |

OTHER PUBLICATIONS

Pardridge, Current Opinion in Pharmacology, 6: 494-500, 2006.*
Scherr et al., (2003) Inhibition of GM-CSF receptor function by stable RNA interference in a NOD/SCID mouse hematopoietic stem cell transplantation model. Oligonucleotides 13(5): 353-63.
Sharp (2001) RNA interference—2001. Genes Dev 15(5): 485-90.
Shevde et al., (2006) Osteopontin knockdown suppresses tumorigenicity of human metastatic breast carcinoma, MDA-MB-435. Clin Exp Metastasis 23(2): 123-33.
Sliwa et al., (2007) The invasion promoting effect of microglia on glioblastoma cells is inhibited by cyclosporin A. Brain 130(Pt 2): 476-89.
Sreekanthreddy et al., (2010) Identification of potential serum biomarkers of glioblastoma: serum osteopontin levels correlate with poor prognosis. Cancer Epidemiol Biomarkers Prev 19(6): 1409-22.
Stupp et al., (2005) Radiotherapy plus concomitant and adjuvant temozolomide for glioblastoma. N Engl J Med 352 (10): 987-96.
Takafuji et al., (2007) An osteopontin fragment is essential for tumor cell invasion in hepatocellular carcinoma. Oncogene 26(44): 6361-71.
Tseng et al., (1997) Induction of antitumor immunity by intracerebrally implanted rat C6 glioma cells genetically engineered to secrete cytokines. J Immunother 20(5): 334-42.
Uemura et al., (2006) Effects of GM-CSF and M-CSF on tumor progression of lung cancer: roles of MEK1/ERK and AKT/PKB pathways. Int J Mol Med 18(2): 365-73.
VonFeldt et al., (1995) Development of GM-CSF antagonist peptides. Pept Res 8(1): 20-7, 30-2.
Wang et al., (2011) Overexpression of osteopontin induces angiogenesis of endothelial progenitor cells via the $\alpha v \beta 3$/PI3K/AKT/eNOS/NO signaling pathway in glioma cells. Eur J Cell Biol 90(8): 642-8.
Wesolowska et al., (2008) Microglia-derived TGF-beta as an important regulator of glioblastoma invasion—an inhibition of TGF-beta-dependent effects by shRNA against human TGF-beta type II receptor. Oncogene 27(7): 918-30.
Wisniewski et al., (2010) Non-apoptotic Fas signaling regulates invasiveness of glioma cells and modulates MMP-2 activity via NFkappaB-TIMP-2 pathway. Cell Signal 22(2): 212-20.
Wisniewski P (2009) The role of FAS ligand in pathogenesis of glioma. PhD Thesis, Institute for Experimental Biology, Polish Academy of Science. Translation of part of thesis.

(Continued)

*Primary Examiner* — Gyan Chandra
(74) *Attorney, Agent, or Firm* — The Roy Gross Law Firm, LLC; Roy Gross

(57) ABSTRACT

Isolated peptides, compositions and methods of use for treating tumors infiltrated with macrophages, such as glioblastomas.

5 Claims, 26 Drawing Sheets

(56) References Cited

OTHER PUBLICATIONS

Yan et al., (2010) Expression pattern of osteopontin splice variants and its functions on cell apoptosis and invasion in glioma cells. Neuro Oncol 12(8): 765-75.
Aharinejad et al., (2004) Colony-stimulating factor-1 blockade by antisense oligonucleotides and small interfering RNAs suppresses growth of human mammary tumor xenografts in mice. Cancer Res 64(15): 5378-84.
Anborgh et al., (2010) Role of the metastasis-promoting protein osteopontin in the tumour microenvironment. J Cell Mol Med 14(8): 2037-44.
Bettinger et al., (2002) Microglia promote glioma migration. Acta Neuropathol 103(4): 351-5.
Burns and Wilks (2011) c-FMS inhibitors: a patent review. Expert Opin Ther Pat 21(2): 147-65.
Chen et al., (2011) Down-regulation of osteopontin inhibits metastasis of hepatocellular carcinoma cells via a mechanism involving MMP-2 and uPA. Oncol Rep 25(3): 803-8.
Ciechomska and Kaminska (2012) ER stress and autophagy contribute to CsA-induced death of malignant glioma cells. Autophagy 8(10): 1526-8.
Clavreul et al., (2010) Autologous tumor cell vaccination plus infusion of GM-CSF by a programmable pump in the treatment of recurrent malignant gliomas. J Clin Neurosci 17(7): 842-8.
Conductier et al., (2010) The role of monocyte chemoattractant protein MCP1/CCL2 in neuroinflammatory diseases. J Neuroimmunol 224(1-2): 93-100.
Crawford et al., (1998) Distinct roles of osteopontin in host defense activity and tumor survival during squamous cell carcinoma progression in vivo. Cancer Res 58(22): 5206-15.
Curran et al., (2011) GM-CSF production by glioblastoma cells has a functional role in eosinophil survival, activation, and growth factor production for enhanced tumor cell proliferation. J Immunol 187(3): 1254-63.
Dai et al., (2010) A humanized anti-osteopontin antibody inhibits breast cancer growth and metastasis in vivo. Cancer Immunol Immunother 59(3): 355-66.
Färber et al., (2008) An alpha5beta1 integrin inhibitor attenuates glioma growth. Mol Cell Neurosci 39(4): 579-85.
Gabrusiewicz et al., (2011) Characteristics of the alternative phenotype of microglia/macrophages and its modulation in experimental gliomas. PLoS One 6(8): e23902.
Groblewska et al., (2007) Serum levels of granulocyte colony-stimulating factor (G-CSF) and macrophage colony-stimulating factor (M-CSF) in pancreatic cancer patients. Clin Chem Lab Med 45(1): 30-4.
Hanisch and Kettenmann (2007) Microglia: active sensor and versatile effector cells in the normal and pathologic brain. Nat Neurosci 10(11): 1387-94.
Hansen et al., (2008) The structure of the GM-CSF receptor complex reveals a distinct mode of cytokine receptor activation. Cell 134(3): 496-507.
Held-Feindt et al., (2010) CX3CR1 promotes recruitment of human glioma-infiltrating microglia/macrophages (GIMs). Exp Cell Res 316(9): 1553-66.
Hercus et al., (1994) Specific human granulocyte-macrophage colony-stimulating factor antagonists. Proc Natl Acad Sci U S A 91(13): 5838-42.
Hibbs et al., (2007) Mice lacking three myeloid colony-stimulating factors (G-CSF, GM-CSF, and M-CSF) still produce macrophages and granulocytes and mount an inflammatory response in a sterile model of peritonitis. J Immunol 178 (10): 6435-43.
Iversen et al., (1996) Inhibition of proliferation and induction of apoptosis in juvenile myelomonocytic leukemic cells by the granulocyte-macrophage colony-stimulating factor analogue E21R. Blood 88(7): 2634-9.
Iversen et al., (1997) The apoptosis-inducing granulocyte-macrophage colony-stimulating factor (GM-CSF) analog E21R functions through specific regions of the heterodimeric GM-CSF receptor and requires interleukin-1beta-converting enzyme-like proteases. J Biol Chem 272(15): 9877-83.
Jan et al., (2010) Osteopontin regulates human glioma cell invasiveness and tumor growth in mice. Neuro Oncol 12(1): 58-70.
Jinushi et al., (2009) Milk fat globule epidermal growth factor-8 blockade triggers tumor destruction through coordinated cell-autonomous and immune-mediated mechanisms. J Exp Med 206(6): 1317-26.
Kaminska et al., (2011) Characteristics of phenotype and pro-tumorigenic roles of glioma infiltrating microglia/macrophages. J Neurol Neurophysiol S5: 1-8.
Kwiatkowska et al., (2011) Downregulation of Akt and FAK phosphorylation reduces invasion of glioblastoma cells by impairment of MT1-MMP shuttling to lamellipodia and downregulates MMPs expression. Biochim Biophys Acta 1813 (5): 655-67.
Lamour et al., (2010) Selective osteopontin knockdown exerts anti-tumoral activity in a human glioblastoma model. Int J Cancer 126(8): 1797-805.
Lin et al., (2002) The macrophage growth factor CSF-1 in mammary gland development and tumor progression. J Mammary Gland Biol Neoplasia 7(2): 147-62.
Lin et al., (2006) Macrophages regulate the angiogenic switch in a mouse model of breast cancer. Cancer Res 66(23): 11238-46.
Lin et al. (2011) Overexpression of osteopontin in hepatocellular carcinoma and its relationships with metastasis, invasion of tumor cells. Mol Biol Rep 38(8): 5205-10.
Liu et al., (2008) CX3CL1 and CX3CR1 in the GL261 murine model of glioma: CX3CR1 deficiency does not impact tumor growth or infiltration of microglia and lymphocytes. J Neuroimmunol 198(1-2): 98-105.
Liu et al., (2010) A short-hairpin RNA targeting osteopontin downregulates MMP-2 and MMP-9 expressions in prostate cancer PC-3 cells. Cancer Lett 295(1): 27-37.
Markovic et al., (2005) Microglia stimulate the invasiveness of glioma cells by increasing the activity of metalloprotease-2. J Neuropathol Exp Neurol 64(9): 754-62.
Markovic et al., (2009) Gliomas induce and exploit microglial MT1-MMP expression for tumor expansion. Proc Natl Acad Sci U S A 106(30): 12530-5.
Monfardini et al., (1996) Rational design of granulocyte-macrophage colony-stimulating factor antagonist peptides. J Biol Chem 271(6): 2966-71.
Monfardini et al., (2002) Structure-based design of mimetics for granulocyte-macrophage colony stimulating factor (GM-CSF). Curr Pharm Des 8(24): 2185-99.
Mroczko et al., (2007) Serum macrophage-colony stimulating factor levels in colorectal cancer patients correlate with lymph node metastasis and poor prognosis. Clin Chim Acta 380(1-2): 208-12.
Neumann et al., (2009) Debris clearance by microglia: an essential link between degeneration and regeneration. Brain 132(Pt 2): 288-95.
Neutzner et al., (2007) MFG-E8/lactadherin promotes tumor growth in an angiogenesis-dependent transgenic mouse model of multistage carcinogenesis. Cancer Res 67(14): 6777-85.
Nowicki et al., (1996) Impaired tumor growth in colony-stimulating factor 1 (CSF-1)-deficient, macrophage-deficient op/op mouse: evidence for a role of CSF-1-dependent macrophages in formation of tumor stroma. Int J Cancer 65(1): 112-9.
Okada et al., (2009) Tumor-associated macrophage/microglia infiltration in human gliomas is correlated with MCP-3, but not MCP-1. Int J Oncol 34(6): 1621-7.
Platten et al., (2003) Monocyte chemoattractant protein-1 increases microglial infiltration and aggressiveness of gliomas. Ann Neurol 54(3): 388-92.
Pollard (2009) Trophic macrophages in development and disease. Nat Rev Immunol 9(4): 259-70.
Rafat et al., (2010) Circulating endothelial progenitor cells in malignant gliomas. J Neurosurg 112(1): 43-9.
Revoltella et al., (2012) Granulocyte-macrophage colony-stimulating factor as an autocrine survival-growth factor in human gliomas. Cytokine 57(3): 347-59.

* cited by examiner

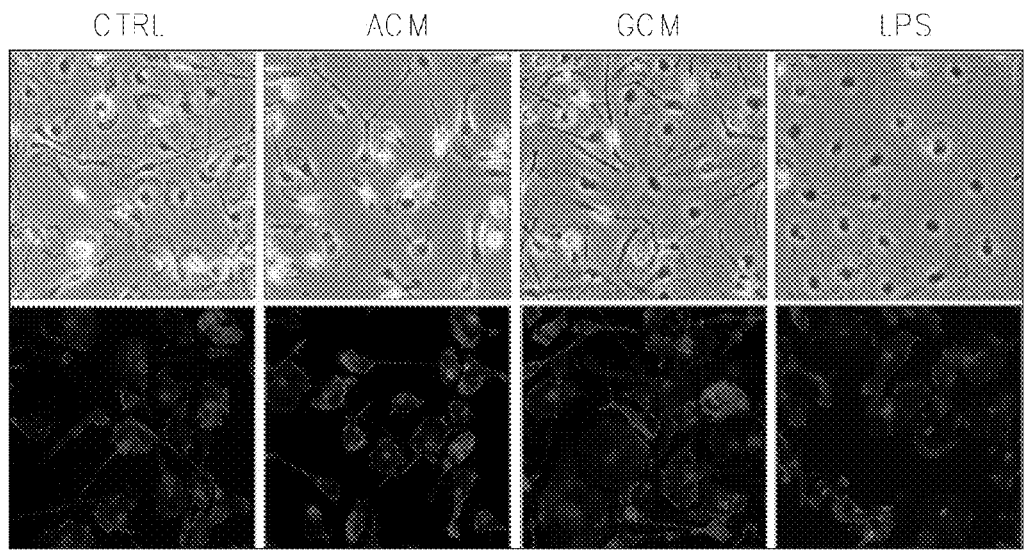
Figure 1A
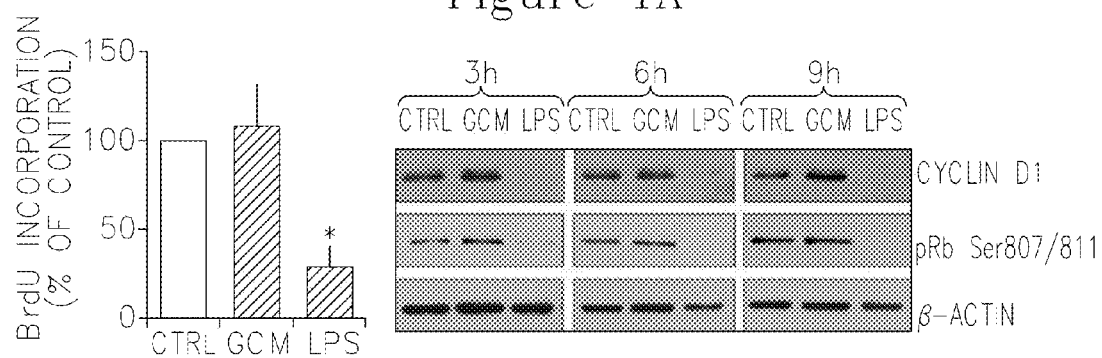
Figure 1B
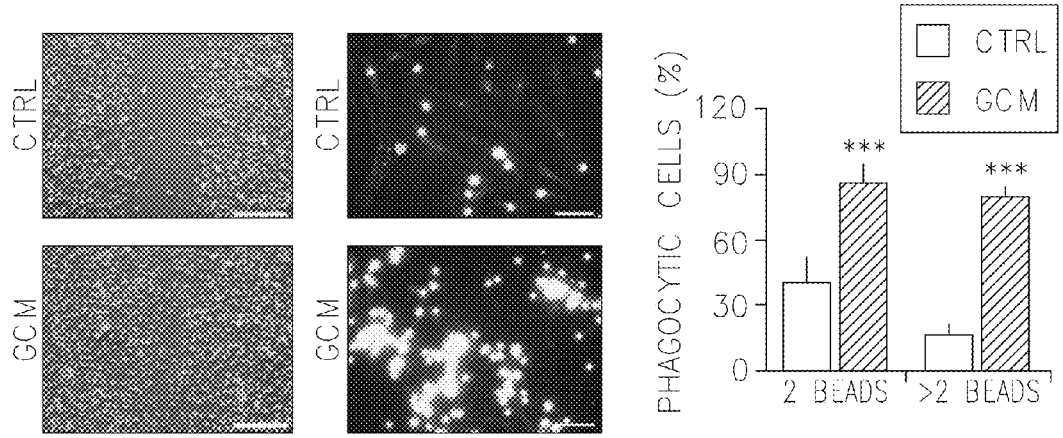
Figure 1C
Figure 1D

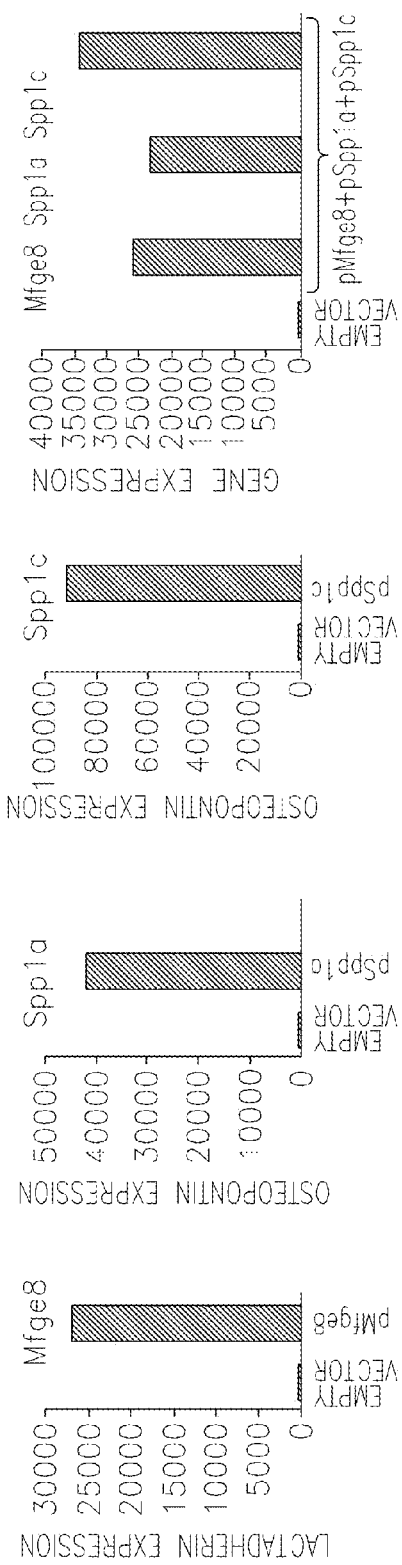
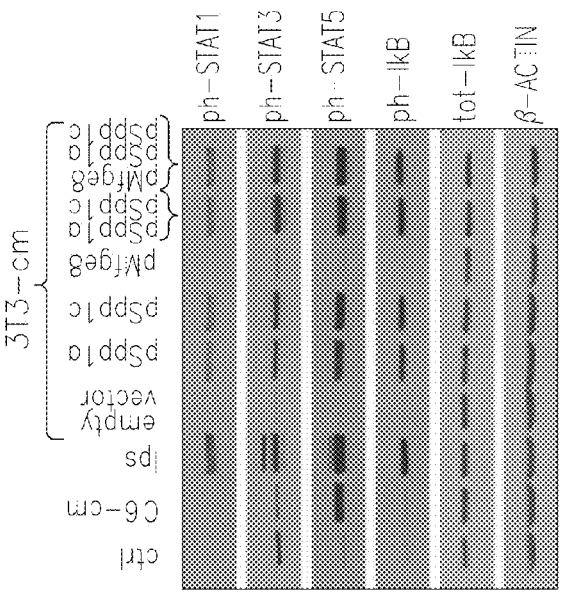
Figure 9A
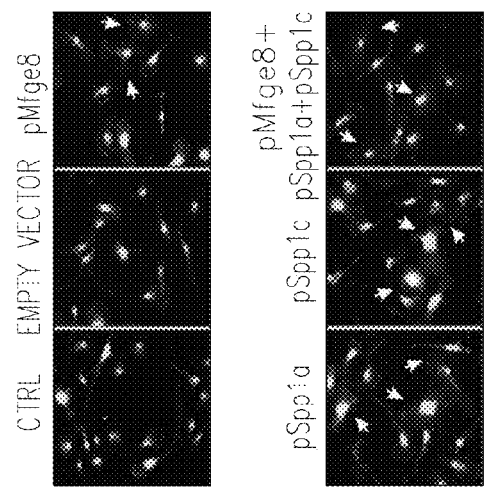
Figure 8A
Figure 8C
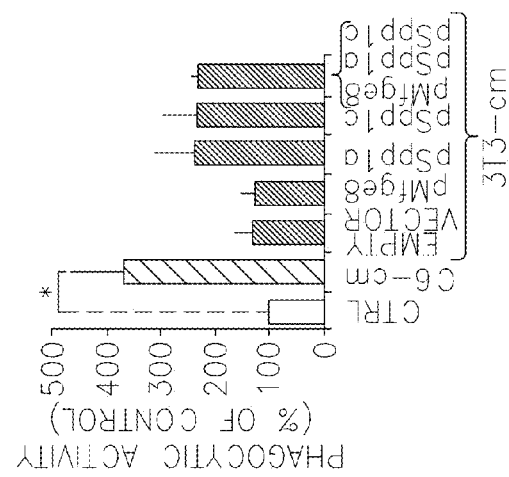
Figure 8B

SEQUENCE LISTING

```
<160> NUMBER OF SEQ ID NOS: 53

<210> SEQ ID NO 1
<211> LENGTH: 17
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 1

Cys Gly Lys Ala Ser Ala Thr Lys Gly Lys Gly Glu Ala Thr Gly Gly
1               5                   10                  15

Cys

<210> SEQ ID NO 2
<211> LENGTH: 19
<212> TYPE: PRT
<213> ORGANISM: ARTIFICIAL
<220> FEATURE:
<223> OTHER INFORMATION: SYNTHETIC PEPTIDE

<400> SEQUENCE: 2

Cys Gly Thr Ala Glu Gly Lys Gly Gly Lys Gly Thr Ala Ser Ala Lys
1               5                   10                  15

Gly Gly Cys

<210> SEQ ID NO 3
<211> LENGTH: 19
<212> TYPE: PRT
<213> ORGANISM: ARTIFICIAL
<220> FEATURE:
<223> OTHER INFORMATION: SYNTHETIC PEPTIDE

<400> SEQUENCE: 3

Gln Pro Trp Glu His Val Asn Ala Ile Gln Glu Arg Arg Leu Leu Asn
1               5                   10                  15

Leu Ser Arg
```

```
<210> SEQ ID NO 4
<211> LENGTH: 17
<212> TYPE: PRT
<213> ORGANISM: ARTIFICIAL
<220> FEATURE:
<223> OTHER INFORMATION: SYNTHETIC PEPTIDE

<400> SEQUENCE: 4

Lys Asp Phe Leu Leu Val Ile Pro Phe Asp Cys Trp Glu Pro Val Gln
1               5                   10                  15

Glu

<210> SEQ ID NO 5
<211> LENGTH: 11
<212> TYPE: PRT
<213> ORGANISM: ARTIFICIAL
<220> FEATURE:
<223> OTHER INFORMATION: SYNTHETIC PEPTIDE

<400> SEQUENCE: 5

Phe Gln Tyr Gln Leu Asp Val His Arg Lys Asn
1               5                   10

<210> SEQ ID NO 6
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 6

Ala Asp Val Arg Ile Leu Asn
1               5

<210> SEQ ID NO 7
<211> LENGTH: 7
<212> TYPE: PRT
<213> ORGANISM: ARTIFICIAL
<220> FEATURE:
<223> OTHER INFORMATION: SYNTHTIC PEPTIDE

<400> SEQUENCE: 7

Asp Gly Arg Gly Asp Ser Val
1               5

<210> SEQ ID NO 8
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 8

Glu Val Arg Gly Asp Val Phe
1               5

<210> SEQ ID NO 9
<211> LENGTH: 314
<212> TYPE: PRT
<213> ORGANISM: HUMAN

<400> SEQUENCE: 9

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30
```

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Phe Arg Arg
                165                 170                 175

Pro Asp Ile Gln Tyr Pro Asp Ala Thr Asp Glu Asp Ile Thr Ser His
                180                 185                 190

Met Glu Ser Glu Glu Leu Asn Gly Ala Tyr Lys Ala Ile Pro Val Ala
            195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
    275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 10
<211> LENGTH: 300
<212> TYPE: PRT
<213> ORGANISM: HUMAN

<400> SEQUENCE: 10

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Thr Leu Pro Ser Lys Ser
    50                  55                  60

Asn Glu Ser His Asp His Met Asp Asp Met Asp Glu Asp Asp Asp
65                  70                  75                  80

Asp His Val Asp Ser Gln Asp Ser Ile Asp Ser Asn Asp Ser Asp Asp

```
                    85                   90                   95
Val Asp Asp Thr Asp Asp Ser His Gln Ser Asp Glu Ser His His Ser
                100                 105                 110

Asp Glu Ser Asp Glu Leu Val Thr Asp Phe Pro Thr Asp Leu Pro Ala
            115                 120                 125

Thr Glu Val Phe Thr Pro Val Pro Thr Val Asp Thr Tyr Asp Gly
        130                 135                 140

Arg Gly Asp Ser Val Val Tyr Gly Leu Arg Ser Lys Ser Lys Lys Phe
145                 150                 155                 160

Arg Arg Pro Asp Ile Gln Tyr Pro Asp Ala Thr Asp Glu Asp Ile Thr
                165                 170                 175

Ser His Met Glu Ser Glu Leu Asn Gly Ala Tyr Lys Ala Ile Pro
                180                 185                 190

Val Ala Gln Asp Leu Asn Ala Pro Ser Asp Trp Asp Ser Arg Gly Lys
            195                 200                 205

Asp Ser Tyr Glu Thr Ser Gln Leu Asp Asp Gln Ser Ala Glu Thr His
        210                 215                 220

Ser His Lys Gln Ser Arg Leu Tyr Lys Arg Lys Ala Asn Asp Glu Ser
225                 230                 235                 240

Asn Glu His Ser Asp Val Ile Asp Ser Gln Glu Leu Ser Lys Val Ser
                245                 250                 255

Arg Glu Phe His Ser His Glu Phe His Ser His Glu Asp Met Leu Val
                260                 265                 270

Val Asp Pro Lys Ser Lys Glu Glu Asp Lys His Leu Lys Phe Arg Ile
            275                 280                 285

Ser His Glu Leu Asp Ser Ala Ser Ser Glu Val Asn
        290                 295                 300

<210> SEQ ID NO 11
<211> LENGTH: 287
<212> TYPE: PRT
<213> ORGANISM: HUMAN

<400> SEQUENCE: 11

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Asn
                20                  25                  30

Ala Val Ser Ser Glu Glu Thr Asn Asp Phe Lys Gln Glu Thr Leu Pro
            35                  40                  45

Ser Lys Ser Asn Glu Ser His Asp His Met Asp Asp Met Asp Asp Glu
        50                  55                  60

Asp Asp Asp Asp His Val Asp Ser Gln Asp Ser Ile Asp Ser Asn Asp
65                  70                  75                  80

Ser Asp Asp Val Asp Asp Thr Asp Asp Ser His Gln Ser Asp Glu Ser
                85                  90                  95

His His Ser Asp Glu Ser Asp Glu Leu Val Thr Asp Phe Pro Thr Asp
                100                 105                 110

Leu Pro Ala Thr Glu Val Phe Thr Pro Val Val Pro Thr Val Asp Thr
            115                 120                 125

Tyr Asp Gly Arg Gly Asp Ser Val Val Tyr Gly Leu Arg Ser Lys Ser
        130                 135                 140

Lys Lys Phe Arg Arg Pro Asp Ile Gln Tyr Pro Asp Ala Thr Asp Glu
145                 150                 155                 160
```

```
Asp Ile Thr Ser His Met Glu Ser Glu Glu Leu Asn Gly Ala Tyr Lys
            165                 170                 175

Ala Ile Pro Val Ala Gln Asp Leu Asn Ala Pro Ser Asp Trp Asp Ser
        180                 185                 190

Arg Gly Lys Asp Ser Tyr Glu Thr Ser Gln Leu Asp Asp Gln Ser Ala
            195                 200                 205

Glu Thr His Ser His Lys Gln Ser Arg Leu Tyr Lys Arg Lys Ala Asn
        210                 215                 220

Asp Glu Ser Asn Glu His Ser Asp Val Ile Asp Ser Gln Glu Leu Ser
225                 230                 235                 240

Lys Val Ser Arg Glu Phe His Ser His Glu Phe His Ser His Glu Asp
                245                 250                 255

Met Leu Val Val Asp Pro Lys Ser Lys Glu Glu Asp Lys His Leu Lys
            260                 265                 270

Phe Arg Ile Ser His Glu Leu Asp Ser Ala Ser Ser Glu Val Asn
                275                 280                 285

<210> SEQ ID NO 12
<211> LENGTH: 273
<212> TYPE: PRT
<213> ORGANISM: HUMAN

<400> SEQUENCE: 12

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Thr
            20                  25                  30

Leu Pro Ser Lys Ser Asn Glu Ser His Asp His Met Asp Asp Met Asp
        35                  40                  45

Asp Glu Asp Asp Asp Asp His Val Asp Ser Gln Asp Ser Ile Asp Ser
    50                  55                  60

Asn Asp Ser Asp Asp Val Asp Asp Thr Asp Asp Ser His Gln Ser Asp
65                  70                  75                  80

Glu Ser His His Ser Asp Glu Ser Asp Glu Leu Val Thr Asp Phe Pro
                85                  90                  95

Thr Asp Leu Pro Ala Thr Glu Val Phe Thr Pro Val Val Pro Thr Val
            100                 105                 110

Asp Thr Tyr Asp Gly Arg Gly Asp Ser Val Val Tyr Gly Leu Arg Ser
        115                 120                 125

Lys Ser Lys Lys Phe Arg Arg Pro Asp Ile Gln Tyr Pro Asp Ala Thr
130                 135                 140

Asp Glu Asp Ile Thr Ser His Met Glu Ser Glu Glu Leu Asn Gly Ala
145                 150                 155                 160

Tyr Lys Ala Ile Pro Val Ala Gln Asp Leu Asn Ala Pro Ser Asp Trp
                165                 170                 175

Asp Ser Arg Gly Lys Asp Ser Tyr Glu Thr Ser Gln Leu Asp Asp Gln
            180                 185                 190

Ser Ala Glu Thr His Ser His Lys Gln Ser Arg Leu Tyr Lys Arg Lys
        195                 200                 205

Ala Asn Asp Glu Ser Asn Glu His Ser Asp Val Ile Asp Ser Gln Glu
    210                 215                 220

Leu Ser Lys Val Ser Arg Glu Phe His Ser His Glu Phe His Ser His
225                 230                 235                 240

Glu Asp Met Leu Val Val Asp Pro Lys Ser Lys Glu Glu Asp Lys His
                245                 250                 255
```

```
Leu Lys Phe Arg Ile Ser His Glu Leu Asp Ser Ala Ser Ser Glu Val
            260                 265                 270

Asn

<210> SEQ ID NO 13
<211> LENGTH: 327
<212> TYPE: PRT
<213> ORGANISM: HUMAN

<400> SEQUENCE: 13

Met Gly Ile Val Pro Arg Ser Leu Asp Lys Lys Ala His Arg Val Gln
1               5                   10                  15

Phe Gln Leu Asn Arg Ile Lys Ala Lys Ile Glu Leu Pro Trp Gly Ser
            20                  25                  30

Leu Gln Leu Asp Cys Leu Met Lys Thr Leu Lys Glu Leu Tyr Asn Lys
        35                  40                  45

Tyr Pro Asp Ala Val Ala Thr Trp Leu Asn Pro Asp Pro Ser Gln Lys
    50                  55                  60

Gln Asn Leu Leu Ala Pro Gln Asn Ala Val Ser Ser Glu Glu Thr Asn
65                  70                  75                  80

Asp Phe Lys Gln Glu Thr Leu Pro Ser Lys Ser Asn Glu Ser His Asp
                85                  90                  95

His Met Asp Asp Met Asp Asp Glu Asp Asp Asp His Val Asp Ser
            100                 105                 110

Gln Asp Ser Ile Asp Ser Asn Asp Ser Asp Val Asp Asp Thr Asp
                115                 120                 125

Asp Ser His Gln Ser Asp Glu Ser His His Ser Asp Glu Ser Asp Glu
    130                 135                 140

Leu Val Thr Asp Phe Pro Thr Asp Leu Pro Ala Thr Glu Val Phe Thr
145                 150                 155                 160

Pro Val Val Pro Thr Val Asp Thr Tyr Asp Gly Arg Gly Asp Ser Val
                165                 170                 175

Val Tyr Gly Leu Arg Ser Lys Ser Lys Lys Phe Arg Arg Pro Asp Ile
            180                 185                 190

Gln Tyr Pro Asp Ala Thr Asp Glu Asp Ile Thr Ser His Met Glu Ser
        195                 200                 205

Glu Glu Leu Asn Gly Ala Tyr Lys Ala Ile Pro Val Ala Gln Asp Leu
    210                 215                 220

Asn Ala Pro Ser Asp Trp Asp Ser Arg Gly Lys Asp Ser Tyr Glu Thr
225                 230                 235                 240

Ser Gln Leu Asp Asp Gln Ser Ala Glu Thr His Ser His Lys Gln Ser
                245                 250                 255

Arg Leu Tyr Lys Arg Lys Ala Asn Asp Glu Ser Asn Glu His Ser Asp
            260                 265                 270

Val Ile Asp Ser Gln Glu Leu Ser Lys Val Ser Arg Glu Phe His Ser
        275                 280                 285

His Glu Phe His Ser His Glu Asp Met Leu Val Val Asp Pro Lys Ser
    290                 295                 300

Lys Glu Glu Asp Lys His Leu Lys Phe Arg Ile Ser His Glu Leu Asp
305                 310                 315                 320

Ser Ala Ser Ser Glu Val Asn
                325

<210> SEQ ID NO 14
```

<211> LENGTH: 387
<212> TYPE: PRT
<213> ORGANISM: HUMAN

<400> SEQUENCE: 14

```
Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Val Asp Leu Gly Ser Ser Lys Glu Val Thr Gly Ile Ile Thr
    290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
    370                 375                 380

Leu Gly Cys
```

<210> SEQ ID NO 15
<211> LENGTH: 144
<212> TYPE: PRT
<213> ORGANISM: HUMAN

<400> SEQUENCE: 15

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 16
<211> LENGTH: 335
<212> TYPE: PRT
<213> ORGANISM: HUMAN

<400> SEQUENCE: 16

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
                20                  25                  30

His Asn Gly Gly Leu Cys Glu Glu Ile Ser Gln Glu Val Arg Gly Asp
            35                  40                  45

Val Phe Pro Ser Tyr Thr Cys Thr Cys Leu Lys Gly Tyr Ala Gly Asn
        50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His

```
                    180                 185                 190
Val Asn Leu Phe Glu Thr Pro Val Glu Ala Gln Tyr Val Arg Leu Tyr
            195                 200                 205

Pro Thr Ser Cys His Thr Ala Cys Thr Leu Arg Phe Glu Leu Leu Gly
        210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Ile Phe Pro Gly Asn Trp Asp Asn His Ser His Lys Lys Asn
    290                 295                 300

Leu Phe Glu Thr Pro Ile Leu Ala Arg Tyr Val Arg Ile Leu Pro Val
305                 310                 315                 320

Ala Trp His Asn Arg Ile Ala Leu Arg Leu Glu Leu Leu Gly Cys
                325                 330                 335
```

<210> SEQ ID NO 17
<211> LENGTH: 4
<212> TYPE: PRT
<213> ORGANISM: ARTIFICIAL
<220> FEATURE:
<223> OTHER INFORMATION: MOTIF
<220> FEATURE:
<221> NAME/KEY: MISC_FEATURE
<222> LOCATION: (1)..(1)
<223> OTHER INFORMATION: X=ANY AMINO ACID
<220> FEATURE:
<221> NAME/KEY: MISC_FEATURE
<222> LOCATION: (1)..(1)
<223> OTHER INFORMATION: X =ANY AMINO ACID

<400> SEQUENCE: 17

Xaa Arg Gly Asp
1

<210> SEQ ID NO 18
<211> LENGTH: 7
<212> TYPE: PRT
<213> ORGANISM: ARTIFICIAL
<220> FEATURE:
<223> OTHER INFORMATION: SYNTHETIC PEPTIDE

<400> SEQUENCE: 18

Thr Gln Arg Gly Asp Ile Phe
1               5

<210> SEQ ID NO 19
<211> LENGTH: 21
<212> TYPE: DNA
<213> ORGANISM: ARTIFICIAL
<220> FEATURE:
<223> OTHER INFORMATION: SYNTHSIZED POLYNUCLEOTIDE

<400> SEQUENCE: 19
caagctagtc ctagacccta a                                        21

<210> SEQ ID NO 20
<211> LENGTH: 21
<212> TYPE: DNA

```
<213> ORGANISM: ARTIFICIAL
<220> FEATURE:
<223> OTHER INFORMATION: SYNTHESIZED POLYNUCLEOTIDE

<400> SEQUENCE: 20
caggatgaaa gcggaaccgg a                                              21

<210> SEQ ID NO 21
<211> LENGTH: 65
<212> TYPE: DNA
<213> ORGANISM: ARTIFICIAL
<220> FEATURE:
<223> OTHER INFORMATION: SYNTHESIZED POLYNUCLEOTIDE

<400> SEQUENCE: 21
gatccagcta gtcctagacc ctaattcaag agattagggt ctaggactag cttgtttttt    60
ggaaa                                                                65

<210> SEQ ID NO 22
<211> LENGTH: 65
<212> TYPE: DNA
<213> ORGANISM: ARTIFICIAL
<220> FEATURE:
<223> OTHER INFORMATION: SYNTHESIZED POLYNUCLEOTIDE

<400> SEQUENCE: 22
agcttttcca aaaacaagc tagtcctaga ccctaatctc ttgaattagg gtctaggact     60
agctg                                                                65

<210> SEQ ID NO 23
<211> LENGTH: 66
<212> TYPE: DNA
<213> ORGANISM: ARTIFICIAL
<220> FEATURE:
<223> OTHER INFORMATION: SYNTHESIZED POLYNUCLEOTIDE

<400> SEQUENCE: 23
gatcccggaa acggactgtg aaacattcaa gagatgtttc acagtccgtt tccggttttt    60
tggaaa                                                               66

<210> SEQ ID NO 24
<211> LENGTH: 66
<212> TYPE: DNA
<213> ORGANISM: ARTIFICIAL
<220> FEATURE:
<223> OTHER INFORMATION: SYNTHESIZED POLYNUCLEOTIDE

<400> SEQUENCE: 24
agcttttcca aaaaccgga acggactgt gaaacatctc ttgaatgttt cacagtccgt      60
ttccgg                                                               66

<210> SEQ ID NO 25
<211> LENGTH: 65
<212> TYPE: DNA
<213> ORGANISM: ARTIFICIAL
<220> FEATURE:
<223> OTHER INFORMATION: SYNTHESIZED DNA

<400> SEQUENCE: 25
gatccggatg aaagcggaac cggattcaag agatccggtt ccgctttcat cctgtttttt    60
ggaaa                                                                65
```

<210> SEQ ID NO 26
<211> LENGTH: 65
<212> TYPE: DNA
<213> ORGANISM: ARTIFICIAL
<220> FEATURE:
<223> OTHER INFORMATION: SYNTHESIZED DNA

<400> SEQUENCE: 26
agcttttcca aaaacagga tgaaagcgga accggatctc ttgaatccgg ttccgctttc    60
atccg                                                              65

<210> SEQ ID NO 27
<211> LENGTH: 25
<212> TYPE: DNA
<213> ORGANISM: ARTIFICIAL
<220> FEATURE:
<223> OTHER INFORMATION: PRIMER

<400> SEQUENCE: 27
tgcctgtcac gttgaatgaa gaggt                                        25

<210> SEQ ID NO 28
<211> LENGTH: 20
<212> TYPE: DNA
<213> ORGANISM: ARTIFICIAL
<220> FEATURE:
<223> OTHER INFORMATION: PRIMER

<400> SEQUENCE: 28
gccccgtaga ccctgctcga                                              20

<210> SEQ ID NO 29
<211> LENGTH: 22
<212> TYPE: DNA
<213> ORGANISM: ARTIFICIAL
<220> FEATURE:
<223> OTHER INFORMATION: PRIMER

<400> SEQUENCE: 29
cggacatcta agggcatcaa ca                                           22

<210> SEQ ID NO 30
<211> LENGTH: 21
<212> TYPE: DNA
<213> ORGANISM: ARTIFICIAL
<220> FEATURE:
<223> OTHER INFORMATION: PRIMER

<400> SEQUENCE: 30
aacgaacgag actctggcat g                                            21

<210> SEQ ID NO 31
<211> LENGTH: 34
<212> TYPE: DNA
<213> ORGANISM: ARTIFICIAL
<220> FEATURE:
<223> OTHER INFORMATION: PRIMER

<400> SEQUENCE: 31
atcaaagctt catatgagac tggcagtggt ttgc                              34

<210> SEQ ID NO 32
<211> LENGTH: 36
<212> TYPE: DNA
<213> ORGANISM: ARTIFICIAL
<220> FEATURE:

```
<223> OTHER INFORMATION: PRIMER

<400> SEQUENCE: 32
atcgcggccg cttaattgac ctcagaagat gaactc                              36

<210> SEQ ID NO 33
<211> LENGTH: 36
<212> TYPE: DNA
<213> ORGANISM: ARTIFICIAL
<220> FEATURE:
<223> OTHER INFORMATION: PRIMER

<400> SEQUENCE: 33
atcaaagctt catatgcagt tctcccgtgt gctggc                              36

<210> SEQ ID NO 34
<211> LENGTH: 33
<212> TYPE: DNA
<213> ORGANISM: ARTIFICIAL
<220> FEATURE:
<223> OTHER INFORMATION: PRIMER

<400> SEQUENCE: 34
atcgcggccg ctaacagccc agcagctcca ggc                                 33

<210> SEQ ID NO 35
<211> LENGTH: 19
<212> TYPE: RNA
<213> ORGANISM: ARTIFICIAL
<220> FEATURE:
<223> OTHER INFORMATION: SYNTHESIZED RNA

<400> SEQUENCE: 35
agcuaguccu agacccuaa                                                 19

<210> SEQ ID NO 36
<211> LENGTH: 19
<212> TYPE: RNA
<213> ORGANISM: ARTIFICIAL
<220> FEATURE:
<223> OTHER INFORMATION: SYNTHEZID RNA

<400> SEQUENCE: 36
uuagggucua ggacuagcu                                                 19

<210> SEQ ID NO 37
<211> LENGTH: 19
<212> TYPE: RNA
<213> ORGANISM: ARTIFICIAL
<220> FEATURE:
<223> OTHER INFORMATION: SYNTHESIZED RNA

<400> SEQUENCE: 37
ggaugaaagc ggaaccgga                                                 19

<210> SEQ ID NO 38
<211> LENGTH: 19
<212> TYPE: RNA
<213> ORGANISM: ARTIFICIAL
<220> FEATURE:
<223> OTHER INFORMATION: SYNTHESIZED RNA

<400> SEQUENCE: 38
uccgguuccg cuuucaucc                                                 19
```

```
<210> SEQ ID NO 39
<211> LENGTH: 66
<212> TYPE: DNA
<213> ORGANISM: ARTIFICIAL
<220> FEATURE:
<223> OTHER INFORMATION: SYNTHESIZED DNA

<400> SEQUENCE: 39
gatccaaaga gaacctgaag gacttttcaa gagaaagtcc ttcaggttct ctttgttttt      60
tggaaa                                                                66

<210> SEQ ID NO 40
<211> LENGTH: 66
<212> TYPE: DNA
<213> ORGANISM: ARTIFICIAL
<220> FEATURE:
<223> OTHER INFORMATION: SYNTHESIZED DNA

<400> SEQUENCE: 40
agcttttcca aaaacaaag agaacctgaa ggactttctc ttgaaaagtc cttcaggttc       60
tctttg                                                                66

<210> SEQ ID NO 41
<211> LENGTH: 65
<212> TYPE: DNA
<213> ORGANISM: ARTIFICIAL
<220> FEATURE:
<223> OTHER INFORMATION: SYNTHESIZED DNA

<400> SEQUENCE: 41
gatccccgga cagccctgtg gctatattca agagatatag ccacagggct gtccttttt       60 ggaag                                                                 65

<210> SEQ ID NO 42
<211> LENGTH: 65
<212> TYPE: DNA
<213> ORGANISM: ARTIFICIAL
<220> FEATURE:
<223> OTHER INFORMATION: SYNTHESIZED DNA

<400> SEQUENCE: 42
tcgacttcca aaaaggaca gccctgtggc tatatctctt gaatatagcc acagggctgt       60
ccggg                                                                 65

<210> SEQ ID NO 43
<211> LENGTH: 7
<212> TYPE: PRT
<213> ORGANISM: artificial
<220> FEATURE:
<223> OTHER INFORMATION: synthetic peptide

<400> SEQUENCE: 43

Asp Gln Ile Gly Phe Arg Thr
1               5

<210> SEQ ID NO 44
<211> LENGTH: 20
<212> TYPE: PRT
<213> ORGANISM: Artificial Sequence
<220> FEATURE:
<223> OTHER INFORMATION: peptide

<400> SEQUENCE: 44

Ser Phe Pro Val Ser Asp Glu Gln Tyr Pro Asp Ala Thr Asp Glu Asp
```

Leu Thr Ser Arg
            20

<210> SEQ ID NO 45
<211> LENGTH: 13
<212> TYPE: PRT
<213> ORGANISM: Artificial Sequence
<220> FEATURE:
<223> OTHER INFORMATION: peptide

<400> SEQUENCE: 45

Ile Ser His Glu Leu Glu Ser Ser Ser Glu Val Asn
1               5                   10

<210> SEQ ID NO 46
<211> LENGTH: 20
<212> TYPE: PRT
<213> ORGANISM: Artificial Sequence
<220> FEATURE:
<223> OTHER INFORMATION: peptide

<400> SEQUENCE: 46

Ser Phe Pro Val Ser Asp Glu Gln Tyr Pro Asp Ala Thr Asp Glu Asp
1               5                   10                  15

Leu Thr Ser Arg
            20

<210> SEQ ID NO 47
<211> LENGTH: 24
<212> TYPE: PRT
<213> ORGANISM: Artificial Sequence
<220> FEATURE:
<223> OTHER INFORMATION: peptide

<400> SEQUENCE: 47

Thr Gly Ile Val Asn Ala Trp Thr Ala Ser Ser Tyr Asp Ser Lys Pro
1               5                   10                  15

Trp Ile Gln Val Asp Phe Leu Arg
            20

<210> SEQ ID NO 48
<211> LENGTH: 25
<212> TYPE: PRT
<213> ORGANISM: Artificial Sequence
<220> FEATURE:
<223> OTHER INFORMATION: peptide

<400> SEQUENCE: 48

Phe Glu Phe Ile Gln Asp Glu Ser Gly Thr Gly Asp Lys Glu Phe Met
1               5                   10                  15

Gly Asn Gln Asp Asn Asn Ser Leu Lys
            20                  25

<210> SEQ ID NO 49
<211> LENGTH: 27
<212> TYPE: PRT
<213> ORGANISM: Artificial Sequence
<220> FEATURE:
<223> OTHER INFORMATION: peptide

<400> SEQUENCE: 49

Gly Asp Ile Phe Thr Glu Tyr Ile Cys Gln Cys Pro Val Gly Tyr Ser
1               5                   10                  15

-continued

```
Gly Ile His Cys Glu Leu Gly Cys Ser Thr Lys
            20                  25

<210> SEQ ID NO 50
<211> LENGTH: 20
<212> TYPE: PRT
<213> ORGANISM: Artificial Sequence
<220> FEATURE:
<223> OTHER INFORMATION: peptide

<400> SEQUENCE: 50

Val Ala His Ser Asp Asp Gly Val Gln Trp Thr Val Tyr Glu Glu Gln
1               5                   10                  15

Gly Thr Ser Lys
            20

<210> SEQ ID NO 51
<211> LENGTH: 12
<212> TYPE: PRT
<213> ORGANISM: Artificial Sequence
<220> FEATURE:
<223> OTHER INFORMATION: peptide

<400> SEQUENCE: 51

Asp Phe Gly His Ile Gln Tyr Val Ala Ser Tyr Lys
1               5                   10

<210> SEQ ID NO 52
<211> LENGTH: 20
<212> TYPE: PRT
<213> ORGANISM: Artificial Sequence
<220> FEATURE:
<223> OTHER INFORMATION: peptide

<400> SEQUENCE: 52

Val Ala His Ser Asp Asp Gly Val Gln Trp Thr Val Tyr Glu Glu Gln
1               5                   10                  15

Gly Thr Ser Lys
            20

<210> SEQ ID NO 53
<211> LENGTH: 27
<212> TYPE: PRT
<213> ORGANISM: Artificial Sequence
<220> FEATURE:
<223> OTHER INFORMATION: peptide

<400> SEQUENCE: 53

Gly Asp Ile Phe Thr Glu Tyr Ile Cys Gln Cys Pro Val Gly Tyr Ser
1               5                   10                  15

Gly Ile His Cys Glu Leu Gly Cys Ser Thr Lys
            20                  25
```

COMPOSITIONS FOR TREATING GLIOMA

FIELD OF THE INVENTION

The present invention is directed to isolated peptides, compositions comprising same and methods of use thereof for treating tumors infiltrated with macrophages, such as glioblastomas.

BACKGROUND OF THE INVENTION

Glioblastomas are considered to be one of the most difficult human malignancies to treat.

Clinical and experimental studies have shown infiltration of malignant glioma tissue with brain resident macrophages (microglia), peripheral monocyte/macrophages and myeloid-derived suppressive cells. Intratumoral density of those cells increases during glioma progression and correlates with malignancy and ablation of microglia in organotypic brain slice cultures and animal glioma models have demonstrated its significant role in supporting glioma invasion (Gabrusiewicz K. et al., *PLoS One;* 6(8):e23902, 2011).

It is suggested that macrophages are attracted by tumor-released molecules and instead of initiating anti-tumor responses, those cells support invasion, angiogenesis, extracellular matrix remodeling and immunosuppression in different types of tumors (Gabrusiewicz K. et al., ibid).

Osteopontin (OPN) is an integrin binding ligand shown to bind to several integrin receptors including $\alpha 4\beta 1$, $\alpha 9\beta 1$, and $\alpha 9\beta 4$ expressed by leukocytes. OPN is expressed in a range of immune cells, including macrophages, neutrophils, dendritic cells, and T and B cells. OPN is reported to act as an immune modulator. It has chemotactic properties, which promote cell recruitment to inflammatory sites. It also functions as an adhesion protein, involved in cell attachment and wound healing. In addition, OPN mediates cell activation and cytokine production, as well as promoting cell survival by regulating apoptosis.

The role of OPN in activation of macrophages has also been implicated in a cancer study, where researchers discovered that OPN-producing tumors were able to induce macrophage activation compared to OPN-deficient tumors (Crawford H C, et al. 1998 Cancer Res. 58 (22): 5206-15).

Lactadherin, also known as milk fat globule-epidermal growth factor 8 (EGF-8), is a glycoprotein secreted by macrophages. Lactadherin binds to apoptotic cells, activated platelets, and phosphatidylserine-expressing red blood cells and anchors them to macrophage integrins via its RGD sequence.

Granulocyte-macrophage colony-stimulating factor (GM-CSF) is a protein secreted by macrophages, T cells, mast cells, NK cells, endothelial cells and fibroblasts. GM-CSF is a cytokine that functions as a white blood cell growth factor. Thus, it is part of the immune/inflammatory cascade, by which activation of a small number of macrophages can rapidly lead to an increase in their numbers, a process crucial for fighting infection.

There is an unmet need for identifying inhibitors that can inhibit the pro-tumor activity of macrophages in tumors such as gliomas.

SUMMARY OF THE INVENTION

Provided herein are isolated peptides, compositions comprising same and methods of using thereof for treating a subject having a tumor that is infiltrated with macrophages ("infiltrating macrophages"), having pro-tumoral activity, and which contribute to the growth or maintenance of the tumor.

Thus, the present invention provides for the first time means for treating tumors having macrophages with pro-tumor activity, e.g., gliomas.

According to one aspect of the invention, there is provided an isolated peptide for inhibiting GM-CSF activity, the peptide comprising an amino acid sequence selected from the group consisting of: an amino acid sequence set forth in SEQ ID NO: 1 (CGKASATKGKGEATGGC), an amino acid sequence set forth in SEQ ID NO: 2 (CGTAEGKGG-KGTASAKGGC), an amino acid sequence set forth in SEQ ID NO: 3 (QPWEHVNAIQERRLLNLSR), an amino acid sequence set forth in SEQ ID NO: 4 (KDFLLVIPFD-CWEPVQE), an amino acid sequence set forth in SEQ ID NO: 5 (FQYQLDVHRKN); and an amino acid sequence set forth in SEQ ID NO: 6 (ADVRILN). Each possibility is a separate embodiment.

According to another aspect of the invention, there is provided an isolated peptide comprising an RGD (Arg-Gly-Asp) motif, wherein the isolated peptide comprises an amino acid sequence set forth in SEQ ID NO: 7 (DGRGDSV).

According to one embodiment, the peptide is of 7-25 amino acids. According to another embodiment, the peptide is of 7-20 amino acids.

According to yet another embodiment, the isolated peptide consists of the sequence set forth in SEQ ID NO: 1, or an analog or derivative thereof. Alternatively, the isolated peptide consists of the sequence set forth in SEQ ID NO: 2, or an analog or derivative thereof. Alternatively, the isolated peptide consists of the sequence set forth in SEQ ID NO: 3, or an analog or derivative thereof. Alternatively, the isolated peptide consists of the sequence set forth in SEQ ID NO: 4, or an analog or derivative thereof. Alternatively, the isolated peptide consists of the sequence set forth in SEQ ID NO: 5, or an analog or derivative thereof. Alternatively, the isolated peptide consists of the sequence set forth in SEQ ID NO: 6, or an analog or derivative thereof. Alternatively, the isolated peptide consists of the sequence set forth in SEQ ID NO: 7, or an analog or derivative thereof.

According to yet another embodiment, the peptide is a cyclic peptide.

According to yet another aspect of the invention, there is provided a pharmaceutical composition comprising an isolated peptide selected from the group consisting of: an amino acid sequence set forth in SEQ ID NO: 1, an amino acid sequence set forth in SEQ ID NO: 2, an amino acid sequence set forth in SEQ ID NO: 3, an amino acid sequence set forth in SEQ ID NO: 4, an amino acid sequence set forth in SEQ ID NO: 5, an amino acid sequence set forth in SEQ ID NO: 6 and an amino acid sequence set forth in SEQ ID NO: 7, essentially as disclosed in the previous aspect of the invention and a pharmaceutical acceptable carrier.

According to one embodiment, the pharmaceutical acceptable carrier is selected from the group consisting of: an aqueous solution, vegetable oil, alcohol, polyethylene glycol, propylene glycol or glycerin. Each possibility is a separate embodiment.

According to another embodiment, the pharmaceutical composition is for treating glioma. According to yet another embodiment, glioma is selected from the group consisting of: ependymoma, astrocytoma, oligodendroglioma, glioblastoma or a mixed glioma. Each possibility is a separate embodiment.

According to yet another aspect of the invention, there is provided a method for treating glioma comprising administering to a subject in need thereof a therapeutically effective amount of a pharmaceutical composition comprising a peptide capable of inhibiting GM-CSF activity, wherein said peptide comprises a sequence selected from the group consisting of: an amino acid sequence set forth in SEQ ID NO: 1, an amino acid sequence set forth in SEQ ID NO: 2, an amino acid sequence set forth in SEQ ID NO: 3, an amino acid sequence set forth in SEQ ID NO: 4, an amino acid sequence set forth in SEQ ID NO: 5 and an amino acid sequence set forth in SEQ ID NO: 6, essentially as disclosed in the previous aspect of the invention.

According to yet another aspect of the invention, there is provided a method for treating glioma comprising administering to a subject in need thereof a therapeutically effective amount of a pharmaceutical composition comprising a peptide comprising an RGD (Arg-Gly-Asp) motif; wherein said peptide comprises an amino acid sequence set forth in SEQ ID NO: 7.

According to one embodiment, the peptide is of 7-25 amino acids. According to another embodiment, the peptide is of 7-20 amino acids.

According to yet another embodiment, the peptide consists of the sequence set forth in SEQ ID NO: 1, or an analog or derivative thereof. Alternatively, the isolated peptide consists of the sequence set forth in SEQ ID NO: 2, or an analog or derivative thereof. Alternatively, the isolated peptide consists of the sequence set forth in SEQ ID NO: 3, or an analog or derivative thereof. Alternatively, the isolated peptide consists of the sequence set forth in SEQ ID NO: 4, or an analog or derivative thereof. Alternatively, the isolated peptide consists of the sequence set forth in SEQ ID NO: 5, or an analog or derivative thereof. Alternatively, the isolated peptide consists of the sequence set forth in SEQ ID NO: 6, or an analog or derivative thereof. Alternatively, the isolated peptide consists of the sequence set forth in SEQ ID NO: 7, or an analog or derivative thereof.

According to yet another embodiment, the peptide is a cyclic peptide.

According to yet another embodiment, glioma is selected from the group consisting of: ependymoma, astrocytoma, oligodendroglioma, glioblastoma, or a mixed glioma. Each possibility is a separate embodiment. According to yet another embodiment, treating glioma is selected from the group consisting of: reducing phagocytosis, reducing motility, reducing proliferation of tumor infiltrating macrophages having pro-tumor activity, and reducing secretion of pro-inflammatory cytokines or chemokines by said macrophage. Each possibility is a separate embodiment.

According to another aspect of the invention, there is provided a kit for the treatment of glioma comprising the pharmaceutical composition comprising the isolated peptide selected from the group consisting of: an amino acid sequence set forth in SEQ ID NO: 1, an amino acid sequence set forth in SEQ ID NO: 2, an amino acid sequence set forth in SEQ ID NO: 3, an amino acid sequence set forth in SEQ ID NO: 4, an amino acid sequence set forth in SEQ ID NO: 5 and an amino acid sequence set forth in SEQ ID NO: 6, an amino acid sequence set forth in SEQ ID NO: 7, essentially as disclosed in the previous aspect of the invention and instructions for use of the kit.

Other objects, features and advantages of the present invention will become clear from the following description.

BRIEF DESCRIPTION OF THE FIGURES

FIGS. 1A-1D show induced amoeboid transformation and motility of microglia cells treated with Glioma Condition Media (GCM): (A) Microscopy analysis of cytoskeletal changes of rat primary microglia cultures exposed to GCM conditioned media by either light contrast microscopy (upper panel) or immune-fluorescence microscopy of F-actin stained cells (lower panel); (B) Immunoblots cyclin D1 and pRb after LPS and GCM treatment; (C) Scratch assay of GCM-treated microglia cell; (D) Phagocytosis assay of GCM-treated microglia cells inoculated with fluorescently labeled beads.

FIGS. 8A-8C show induced phagocytosis and amoeboid transformation of microglia cells exposed to culture media from murine fibroblasts expressing recombinant osteopontin and lactadherin: (A) Quantitative PCR of lactadherin (mfge8) and osteopontin (spp1) in NIH3T3 fibroblasts transiently transfected with plasmids encoding osteopontin and/or lactadherin; (B) Phagocytosis assay of microglia cultures exposed to conditioned media from fibroblasts expressing rat lactadherin (mfge8) and/or osteopontin (spp1); (C) Immunofluorescence microscopy of F-actin in microglia cells exposed to conditioned media from fibroblasts expressing lactadherin (mfge8), and/or osteopontin (spp1).

FIGS. 9A-9B show induced expression of M2 phenotype marker genes in microglia cells exposed to culture media from murine fibroblasts expressing recombinant osteopontin: (A) Western blots using antibodies against phosphorylated (p) or total IκB and STAT1, 3 and 5 in microglia cells exposed to culture media from murine fibroblasts expressing recombinant osteopontin and/or lactadherin; (B) Real Time PCR of selected genes in microglia cultures exposed to conditioned media from fibroblasts expressing osteopontin and/or lactadherin.

DETAILED DESCRIPTION

Figure 2A:
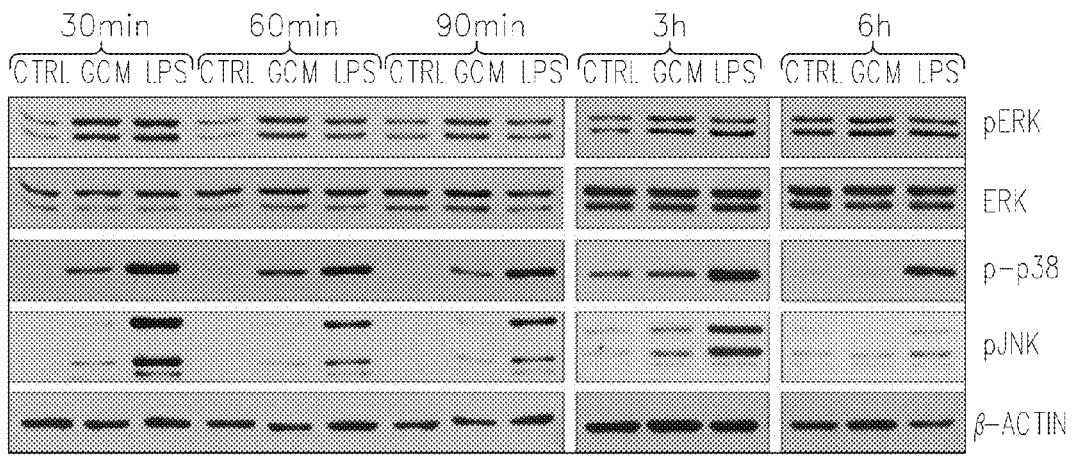
FIGS. 2A-2D show lack of inflammatory signaling in GCM treated microglia cells: (A) Western blots with antibodies against phosphorylated (p) or total MAPK kinases in GCM and LPS treated microglia cells; (B) Immunoblotting of NFκB inhibitor (IκB) and its phosphorylated form (pIκB) in GCM and LPS treated microglia cells; (C) Immunoblotting of phosphorylated STAT transcription factors (Signal Tranducers and Activators of Transcription) in GCM and LPS treated microglia cells; (D) Immunoblotting of inflammation mediators iNOS and COX2 in LPS and GCM, stimulated microglia cells.

Provided herein are methods and compositions for treating a subject having a tumor that is infiltrated with macrophages ("infiltrating macrophages"), e.g. microglia having pro-tumoral activity. Infiltrating macrophages having pro-tumoral activity may participate in matrix remodeling, invasion, angiogenesis and suppression of adaptive immunity and may proliferate, be phagocytic and be mobile. Infiltrating macrophages with pro-tumoral activity, and may contribute to the growth or maintenance of the tumor, are present in tumors, such as malignant tumors, e.g., brain tumors, such as gliomas.

The method of the present invention comprises administering to a subject having a tumor with infiltrating macrophages with pro-tumoral activity a therapeutically effective amount of an inhibitor of an integrin ligand, e.g., osteopontin ("OPN") or lactadherin, to thereby reduce the pro-tumor activity of the infiltrating macrophages with pro-tumoral activity. Alternatively, the method of the invention comprises administering to a subject having a tumor with infiltrating macrophages having pro-tumoral activity a therapeutically effective amount of an inhibitor of GM-CSF to thereby reduce the pro-tumor activity of the infiltrating macrophages with pro-tumoral activity. It is to be understood that an inhibitor according to the present invention, may inhibit the production or the synthesis of OPN, lactadherin and/or GM-CSF. Alternatively, the inhibitor may neutralize the activity of OPN, lactadherin and/or GM-CSF. Alternatively, the inhibitor may prevent or inhibit the binding of OPN, lactadherin and/or GM-CSF to their respective receptors. Alternatively, the inhibitor may inhibit the signal transduction pathway activated by binding of OPN, lactadherin and/or GM-CSF to their receptors on macrophages or microglia cells.

The methods of the invention are directed to treating a disease characterized by the presence of a tumor, e.g., a malignant tumor. By way of a non-limiting example, the tumor is a glioma.

The invention is based in part on the surprising discovery that inhibition of OPN synthesis or the interaction of OPN with an integrin on microglia reduces glioma induced activation of microglia, phagocytosis and integrin mediated signal transduction (e.g., phosphorylation of FAK and Akt kinases). In addition, as exemplified herein, a recombinant OPN mimicked most of glioma-induced functional responses and up-regulated the expression of putative alternative phenotype markers in microglia cultures.

Furthermore, the invention is based on the unexpected findings that inhibition of GM-CSF synthesis reduces invasion of a glioma by macrophages/microglia, reduces tumor size, tumor progression and angiogenesis. In addition, as exemplified herein, GM-CSF levels are highly up-regulated in glioblastoma multiforme patients, and high levels of GM-CSF correlates with poor prognosis.

OPN is also referred to as "secreted phosphoprotein 1," SPP1, BNSP; BSPI; and ETA-1, and has Gene ID: 6696. Human OPN exists as 5 different variants or isoforms, referred to as OPNa, OPNb, OPNc, OPNd, and OPNe, which precursor proteins consist of the amino acid sequences provided under GenBank Accession Nos NP_001035147.1, NP_000573.1, NP_001035149.1, NP_001238758.1, and NP_001238759.1, respectively, which are encoded by the nucleotide sequences provided under GenBank Accession No. NM_001040058.1, NM_000582.2, NM_001040060.1, NM_001251829.1 and NM_001251830.1, respectively. The amino acid sequences of OPNa-OPNe, are set forth as SEQ ID NOs: 9-13, respectively. OPNa-e interact with integrins, such as integrins αVβ3 and αvβ5.

Lactadherin is also referred to as "MFGE8 milk fat globule-EGF factor 8 protein," as well as MFGE8, BA46; HMFG; MFGM; SED1; hP47; EDIL1; MFG-E8; SPAG10; OAcGD3S; and HsT19888, and has Gene ID: 4240. Lactadherin exists as isoforms a and b. The nucleotide and amino acid sequences of human lactadherin isoform a preproprotein is provided under GenBank Accession Nos. NM_005928.2 and NP_005919.2, respectively, and the nucleotide and amino acid sequences of human lactadherin isoform b preproprotein is provided under GenBank Accession Nos. NM_001114614.1 and NP_001108086.1, respectively. Lactadherin isoforms a and b interact with integrins, such as integrins αVβ3 and αvβ5. The amino acid sequences of lactadherin isoforms a and b are set forth as SEQ ID NOs: 14 and 15, respectively.

Granulocyte Macrophage Colony Stimulating Factor is also referred to as "GM-CSF" as well as CSF2, molgramostin and sargramostin, and has Gene ID: 1437 and MIM: 138960. The active form of the protein is found extracellularly as a homodimer. The amino-acid sequence of the human GM-CSF precursor protein is provided under GenBank Accession No. NP_000749.2 (SEQ ID NO: 16), and is encoded by the nucleotide sequence provided under GenBank Accession No. NM_000758.2.

GM-CSF binds its receptor "GMR α" also referred to as CSF2RA, CD116, CDw116, CSF2R, CSF2RAX, CSF2RAY, CSF2RX, CSF2RY, GM-CSF-R-alpha, GMCSFR, GMRa and SMDP4, and has Gene ID: 1430. The amino acid sequences of the precursor of the human isoforms are provided under GenBank Accession Nos: NP_001155001.1, NP_001155002.1, NP_001155003.1, NP_001155004.1, NP_006131.2, NP_758448.1, NP_758449.1, NP_758450.1, and NP_758452.1.

As used herein, the term "integrin ligand inhibitor" refers to an agent that inhibits at least one biological activity of the integrin ligand. For example, an "OPN inhibitor" refers to an agent that inhibits at least one biological activity of OPN (isoforms a, b, c, d and/or e), and a "lactadherin inhibitor" refers to an agent that inhibits at least one biological activity of lactadherin (isoforms a and/or b). According to some embodiments, an OPN or lactadherin inhibitor is an agent that inhibits the ability of OPN or lactadherin, respectively, to induce the pro-tumor activity of a macrophage or reduces the pro-tumor activity of a macrophage by at least 10%, 20%, 30%, 40%, 50%, 60%, 70%, 80%, 90%, 95%, 99% or 100%. An integrin ligand inhibitor can, e.g., prevent or reduce the increased phagocytosis, motility, or proliferation of pro-tumor macrophages or reduce the secretion of pro-inflammatory cytokines or chemokines by pro-tumor macrophages. An exemplary integrin ligand inhibitor, e.g., an OPN inhibitor, is an agent that inhibits or reduces the interaction between the integrin ligand, e.g., OPN, and a protein on the surface of a macrophage, e.g., a microglia, such as an integrin. An integrin ligand inhibitor may be protein or peptide based. An integrin ligand inhibitor may also be an agent that inhibits the expression of the integrin ligand protein, e.g., an inhibitory nucleic acid, e.g., an siRNA, shRNA, antisense molecule, a ribozyme or an aptamer. An "agent" refers to any type of molecule or complex of molecules, such as macromolecules or small molecules.

According to some embodiments, the OPN inhibitor inhibits the activity of all five OPN isoforms. According to some embodiments, the OPN inhibitor inhibits the activity of 1, 2, 3 or 4 OPN isoforms. According to some embodiments, the OPN inhibitor inhibits the activity of OPNc.

According to some embodiments, a lactadherin inhibitor inhibits the activity of both lactadherin isoforms. According to some embodiments, a lactadherin inhibitor inhibits the activity of one or the other isoform only.

An integrin ligand inhibitor may inhibit a biological activity of the integrin ligand by at least 10%, 20%, 30%, 40%, 50%, 60%, 70%, 80%, 90%, 95%, 99% or 100%. For example, an integrin ligand inhibitor may reduce the interaction between the integrin ligand and the integrin by at least 10%, 20%, 30%, 40%, 50%, 60%, 70%, 80%, 90%, 95%, 99% or 100%. An integrin ligand inhibitor may also be an agent that blocks the expression of the integrin ligand protein and may, e.g., reduce its expression by at least 10%, 20%, 30%, 40%, 50%, 60%, 70%, 80%, 90%, 95%, 99% or 100%.

As used herein, the term "GM-CSF inhibitor" refers to an agent that inhibits at least one biological activity of GM-CSF. According to some embodiments, a GM-CSF inhibitor is an agent that inhibits the progression of a tumor, e.g., a glioma, such as by slowing down tumor progression by at least 10%, 20%, 30%, 40%, 50%, 60%, 70%, 80%, 90%, 95%, 99% or 100%, relative to tumor progression in the absence of the GM-CSF inhibitor. The GM-CSF inhibitor can also be an inhibitor that stabilizes tumor (e.g., glioma) size or reduces it by at least 10%, 20%, 30%, 40%, 50%, 60%, 70%, 80%, 90%, 95%, 99% 100% (2 fold), 3 fold, 5 fold or more. The GM-CSF inhibitor can, e.g., reduce tumor invasion by macrophages or microglia; reduce stimulation and/or transformation of tumor infiltrating macrophages into cells having pro-tumor activity; and/or reduce angiogenesis in the tumor. The GM-CSF inhibitor may have one of the following characteristics: (i) block GM-CSF production or synthesis, e.g., by tumor cells; (ii) neutralize the activity of GM-CSF; (iii) prevent (or inhibit) the binding of GM-CSF to its receptor; (iv) inhibit the signal transduction pathway that is activated by the binding of GM-CSF to its receptor on macrophages or microglia or (v) or inhibit GM-CSF receptor production or synthesis, e.g., in macrophages or microglia. The GM-CSF inhibitor may be protein or peptide based. The GM-CSF inhibitor may also be an agent that inhibits the expression of the GM-CSF, e.g., an inhibitory nucleic acid, e.g., an siRNA, shRNA, antisense molecule, a ribozyme or an aptamer. An "agent" as used herein refers to any type of molecule or complex of molecules, such as macromolecules or small molecules.

The GM-CSF inhibitor may inhibit a biological activity of GM-CSF by at least 10%, 20%, 30%, 40%, 50%, 60%, 70%, 80%, 90%, 95%, 99% or 100%. For example, a GM-CSF inhibitor may reduce the interaction between GM-CSF and its receptor by a factor of at least 10%, 20%, 30%, 40%, 50%, 60%, 70%, 80%, 90%, 95%, 99% or 100%. The GM-CSF inhibitor may also be an agent that blocks the expression of the GM-CSF protein or GM-CSF receptor (e.g., a chain) and may, e.g., reduce its expression by a factor of at least 10%, 20%, 30%, 40%, 50%, 60%, 70%, 80%, 90%, 95%, 99% or 100%.

Inhibitory Peptides and Proteins

A) Integrin Ligand Inhibitory Peptides

According to some embodiments, an inhibitor of an integrin ligand, e.g., OPN, is an inhibitory peptide. An integrin ligand inhibitory peptide may be a peptide that inhibits the interaction between the integrin ligand and an integrin, e.g., integrin αVβ3 or αVβ5. In an exemplary embodiment, an integrin ligand inhibitor comprises an RGD (Arg-Gly-Asp) motif (SEQ ID NO: 17). An integrin ligand inhibitor may be a peptide or a protein comprising the RGD (Arg-Gly-Asp) motif, without the peptide or protein inducing signal transduction through the integrin.

An inhibitory peptide may comprise at most 100, 75, 50, 40, 30, 20, 15, 10, 9, 8, 7, 6, 5, 4 or 3 amino acids, e.g., of one of SEQ ID NOs: 9-16. An inhibitory peptide may also comprise from 3 to 20 amino acids; from 3 to 15 amino acids; from 5 to 15 amino acids; from 5 to 10 amino acids; from 6 to 8 amino acids, e.g., of one of SEQ ID NOs: 9-16. According to some embodiments, an inhibitory peptide comprises or consists of 3, 4, 5, 6, 7, 8, 9 or 10 amino acids, e.g., of one of SEQ ID NOs: 9-16. According to some embodiments, an inhibitory peptide comprises or consists of 7-20 amino acids, e.g., of one of SEQ ID NOs: 9-16. According to some embodiments, an inhibitory peptide comprises or consists of 7-15 amino acids, e.g., of one of SEQ ID NOs: 9-16.

According to some embodiments, an inhibitory peptide may preferably comprise an RGD motif. The RGD motif may be located centrally in the inhibitory peptide, or alternatively closer to one end of the peptide than to the other.

An exemplary rat lactadherin inhibitory peptide consists of the amino acid sequence TQRGDIF (SEQ ID NO: 18). An exemplary human OPN RGD inhibitory peptide that may be used comprises or consists of the amino acid sequence set forth in SEQ ID NO: 7—DGRGDSV. Any other human OPN RGD inhibitory peptide may be used, provided that it comprises the RGD motif. For example, a human OPN RGD inhibitory peptide may comprise from 5 to 20 amino acids of the amino acid sequence of a human OPN as set forth in SEQ ID NOs: 9-13, encompassing the RGD motif.

An exemplary human lactadherin RGD peptide that may be used in the method of the present invention, comprises, consists of, or consists essentially of the amino acid sequence set forth in SEQ ID NO: 8—EVRGDVF. Any other human lactadherin RGD inhibitory peptide may be used, provided that it comprises the RGD motif. For example, a human lactadherin RGD inhibitory peptide may comprise from 5 to 20 amino acids of the amino acid sequence of a human lactadherin, as set forth in SEQ ID NOs: 14-15, encompassing the RGD motif.

B) GM-CSF Inhibitory Peptides

According to some embodiments, an inhibitor of GM-CSF is an inhibitory peptide. The GM-CSF inhibitory peptide may be a peptide that inhibits the interaction between GM-CSF and its receptor. According to some embodiments, a GM-CSF inhibitor comprises an amino acid sequence that is identical or similar to that of a portion of GM-CSF that interacts with the GM-CSF receptor, but does not induce signal transduction through the GM-CSF receptor. As further described below, it has been shown that residues 54-61 (B helix) and 77-83 (C helix) of GM-CSF are involved in the interaction with its receptor; thus peptides comprising an amino acid sequence that is identical or similar to amino acids 54-61 or 77-83 may be used as GM-CSF inhibitors.

According to some embodiments, a "GM-CSF inhibitory agent" may also be a peptide or protein comprising an amino acid sequence that (i) is identical or similar to that of a portion of a chain of the GM-CSF receptor and (ii) interacts with GM-CSF to thereby prevent the binding of GM-CSF to its receptor.

It is to be understood that a first amino acid sequence is similar to a second amino acid if, e.g., the first amino acid is at least 70%, 80%, 90%, 95%, 97%, 98% or 99% identical to the second amino acid sequence. For example, the first amino acid sequence may differ from the second amino acid sequence in at most 1, 2, 3, 4, 5, 10 or more amino acids, e.g., amino acid substitutions, deletions or additions.

According to some embodiments, an inhibitory peptide may comprise at most 100, 75, 50, 40, 30, 20, 15, 10, 9, 8, 7, 6, 5, 4 or 3 amino acids, e.g., of SEQ ID NOs: 16. An inhibitory peptide may also comprise from 3 to 20 amino acids; from 3 to 15 amino acids; from 5 to 15 amino acids; from 5 to 10 amino acids; from 6 to 8 amino acids, e.g., of SEQ ID NO: 16. According to some embodiments, an inhibitory peptide comprises or consists of 3, 4, 5, 6, 7, 8, 9 or 10 amino acids, e.g., of SEQ ID NO: 16. According to some embodiments, an inhibitory peptide comprises or consists of 7-20 amino acids, e.g., of one of SEQ ID NO: 16. According to some embodiments, an inhibitory peptide comprises or consists of 7-15 amino acids, e.g., of one of SEQ ID NO: 16. An inhibitory peptide preferably comprises an amino acid sequence of human GM-CSF that interacts with its receptor (or a sequence similar thereto), or an amino acid sequence of the α or βc chain of the receptor (or a sequence similar thereto) that interacts with GM-CSF. The specific sequence may be located centrally in the inhibitory peptide, or alternatively closer to one end of the peptide than to the other.

According to some embodiments, exemplary human GM-CSF inhibitory peptides comprise the amino acid sequence set forth in SEQ ID NO: 1—CGKASATKGKGEATGGC or the amino acid sequence set forth in SEQ ID NO: 2—CG-TAEGKGGKGTASAKGGC together with glycines, alanines, and cysteines introduced for peptide cyclization. Additional inhibitory peptides, which are linear peptide analogs of GM-CSF, include, but are not limited to, the peptides set forth in VonFeldt et al. (Peptide Res. 8:20, 1995, which is incorporated on its entirety herein by reference). These peptides consist of amino acids 17-31 (the A helix) of GM-CSF, which inhibits high affinity receptor binding and a peptide consisting of amino acids 54-78 (B and C helices), which inhibits low affinity receptor binding (VonFeldt et al., ibid).

Further included in the scope of the present invention are short peptides that are inhibitors of GM-CSF, target GM-CSF or its receptor or the receptor complex. For example, an inhibitor may comprise, consist essentially of or consist of the following amino acid sequences of human GM-CSF:

QPWEHVNAIQEARRLLNLSR (SEQ ID NO: 3); and
KDFLLVIPFDCWEPVQE (SEQ ID NO: 4).

An inhibitor of GM-CSF activity may comprise, consist essentially of or consist of the following amino acid sequences of human GM-CSF receptor alpha:

FQYQLDVHRKN; (SEQ ID NO: 5)
and

ADVRILN. (SEQ ID NO: 6)

Also provided are GM-CSF inhibitors that are polypeptides or proteins. For example, decoy receptor can be used to inhibit binding of GM-CSF to the GM-CSF receptor. In other embodiments, decoy GM-CSF may be used. Decoy GM-CSF are GM-CSF molecules that bind to the receptor, but do not activate the receptor, and prevent naturally occurring GM-CSF from binding to the receptors. Decoy GM-CSF molecules may be mutated GM-CSF molecules.

It has been shown that residues on the first (A) helix of GM-CSF (amino acids 11-23 of the mature human GM-CSF) are involved in the binding to the high affinity receptor (GM-CSFRα.βc complex) but not to low affinity receptor (GM-CSFRα alone) (as indicated, e.g., in VonFeldt et al., supra). This has been confirmed by showing that a GM-CSF analogue with the single E21R mutation is an antagonist of the high affinity receptor. Thus, it is expected that GM-CSF inhibitors may comprise GM-CSF sequences that are mutated in the A helix.

The present invention further provides a method of inhibiting an integrin ligand and/or inhibiting GM-CSF in a cell or tissue, e.g., in a human subject, comprising exposing the cell or tissue to a therapeutically effective amount of an inhibitory peptide thereby inhibiting or decreasing the activity of the integrin ligand and/or the activity of GM-CSF.

According to some embodiments, an inhibitory peptide may be a peptide comprising a sequence having at least 60%, 70%, 75%, 80%, 85%, 90%, 95%, 96%, 97%, 98%, 99% or 100% identity to the sequence of an integrin ligand encompassing the RGD motif. An inhibitory peptide may be a peptide comprising a sequence having at least 60%, 70%, 75%, 80%, 85%, 90%, 95%, 96%, 97%, 98%, 99% or 100% identity to the sequence of a human GM-CSF or to the sequence of a chain of the human GM-CSF receptor. Generally, some modifications and changes can be made in the structure of a polypeptide without substantially altering the biological activity of that peptide, to obtain a functionally equivalent polypeptide. Thus, the present invention extends to biologically equivalent polypeptides that differ from a portion of the amino acid sequence of the integrin ligand, e.g., OPN or lactadherin, and biologically active fragments thereof by conservative amino acid substitutions. Likewise, the present invention extends to biologically equivalent polypeptides that differ from a portion of the amino acid sequence of human GM-CSF or human GM-CSF receptor chain, and biologically active fragments thereof by conservative amino acid substitutions.

As used herein, the term "conservative amino acid substitution" refers to the substitution of one amino acid for another at a given location in the peptide, where the substitution can be made without substantial loss of the relevant function. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, and 2,3-diaminobutyric acid.

An inhibitory peptide may be incorporated into a larger fusion protein in order to increase the stability of the protein and to assist in delivery to a target cell. The fusion protein may be designed to incorporate a specific protease cleavage site for recognition by a protease expressed in the target cell so that the peptide modulator is released from the fusion protein upon entry into the target cell. An inhibitory peptide may also be linked to a peptide that favors transport through the blood brain barrier (BBB). For example, an RGD peptide may be fused to ArmaGen Technologies' molecular Trojan horse (MTH). The MTH part of the fusion protein triggers transport across the BBB via an endogenous receptor-mediated transport system.

An inhibitory peptide can be synthesized using standard protein synthesis techniques as are known in the art, for example using chemical peptide ligation methods, including solid phase peptide synthesis, to synthesize the peptide in the C-terminal to N-terminal direction, including using an automated peptide synthesizer. Alternatively, molecular biology techniques may be used to design an expression cassette that will encode the peptide modulator, using standard molecular biology techniques known in the art. The expression cassette can be used in a suitable expression system. For example, the cassette may be contained in a bacterial plasmid and may be expressed in a bacterial cell, from which the peptide modulator can be isolated and purified. The expression cassette will contain an open reading frame encoding the inhibitory peptide, optionally as a complete peptide or as part of a chimeric or fusion peptide or protein, from which the peptide may be released, for example by protease digestion. The expression cassette will also contain suitable regulatory regions operably linked to the open reading frame, for example a promoter region, which may be an inducible promoter region.

Alternatively, the inhibitory peptide may be included in a biomaterial which increases or induces uptake of the inhibitory peptide by the cell, for example, by encapsulating the inhibitory peptide in a liposome preparation. Liposome delivery of peptides and proteins to cells is known, and is described for example in U.S. Pat. No. 6,372,720 and US 20030108597 incorporated herein by reference.

C) Integrin Ligand Inhibitory Antibodies

According to some embodiments, the activity of an integrin ligand, such as OPN or lactadherin, is inhibited with the use of antibodies, such as monoclonal antibodies, or antigen binding fragments or derivatives thereof, that specifically bind to the integrin ligand and thereby inhibit its interaction with an integrin and inhibits the signal transduction pathway initiated from the interaction of the integrin ligand and the integrin.

D) Antibodies that Inhibit GM-CSF or GM-CSF Receptor

According to some embodiments, the activity of GM-CSF is inhibited with the use of antibodies, such as monoclonal antibodies, or antigen binding fragments or derivatives thereof, which specifically bind to GM-CSF and thereby, e.g., inhibit its interaction with the GM-CSF receptor and inhibit the signal transduction pathway initiated from the interaction of GM-CSF with its receptor. An antibody may also induce conformational changes to GM-CSF or GM-CSF receptor, thereby preventing its interaction with the GM-CSF receptor or GM-CSF, respectively. According to some embodiments, the activity of GM-CSF is inhibited with the use of antibodies or an antigen binding fragment or derivatives thereof that specifically bind to the GM-CSF receptor and thereby inhibit signal transduction through the receptor.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). Each VH and VL is composed of three CDR's and four FRs, arranged from amino-terminus to carboxy-terminus in the following order: FR1, CDR1, FR2, CDR2, FR3, CDR3, FR4.

An antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "antigen-binding fragment" of an antibody (or simply "antibody portion," or "fragment"), as used herein, refers to one or more fragments of a full-length antibody that retain the ability to specifically bind to an antigen, e.g., OPN, lactadherin or GM-CSF. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) an isolated complementarity determining region (CDR), and (vii) nanobodies. Furthermore, although the two domains of the Fv fragment, VL and VH, are coded for by separate nucleic acids, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

An exemplary antibody that may be used for inhibiting the activity of lactadherin is Angiolix (HuMc3), a humanized (HuMc3) monoclonal antibody which binds lactadherin, manufactured by Access Pharmaceuticals INC. Angliolix has been reported to bind $\alpha V\beta 3$ integrins on endothelial cells, thereby inhibiting a VEGF-independent integrin signaling.

An exemplary antibody that may be used is the fully human anti-human GM-CSF monoclonal antibody MOR103 that is being produced by MorphoSys. Another exemplary antibody that may be used for inhibiting the activity of human GM-CSF by binding to human GM-CSF is the BVD2-21C11 monoclonal, neutralizing antibody (BD Pharmingen) or monoclonal neutralizing mouse MAB215, IgG1 Clone #3209 (R&D Systems). The neutralization dose (ND50) is typically 0.30.5 µg/mL in the presence of 0.5 ng/mL recombinant human GM-CSF. An exemplary antibody that may be used for inhibiting the activity of human GM-CSF by binding to human GM-CSF receptor is monoclonal neutralizing anti-MGM-CSF receptor, clone K12B7.17A (Millipore) or MAB1037 (Chemicon) that binds to the alpha chain of human GM-CSF receptor and neutralizes native and recombinant GM-CSFR.

Another antibody that may be used in the methods described herein is Mavrilimumab, formerly known as CAM-3001, which a human monoclonal antibody targeting GM-CSF receptor-α.

Inhibitory Nucleic Acids

According to some embodiments, inhibitory nucleic acids that reduce expression of an integrin ligand, such as OPN, are used. According to some embodiments, inhibitory nucleic acids that reduce expression of GM-CSF or GM-CSF receptor are used. For example, small interfering RNAs (siRNAs), antisense, morpholino oligos, and ribozymes can all be used. Useful inhibitory nucleic acids include those that reduce the expression of an integrin ligand by at least 10%, 20%, 30%, 40%, 50%, 60%, 70%, 80%, 90%, 95% or 99% in a cell or tissue compared to a cell or tissue that has not been exposed to the inhibitory nucleic acid.

Accordingly, provided herein are methods comprising administering to a subject in need thereof one or more inhibitory nucleic acid molecules that are targeted to an integrin ligand or GM-CSF/GM-CSF receptor, e.g., siRNA, antisense, ribozymes, peptide nucleic acids, and aptamers, to thereby reduce the level of the integrin ligand protein or GM-CSF protein in the subject.

A) Integrin Ligand, GM-CSF and GM-CSF Inhibitory Nucleic Acid Molecules for RNAi RNAi is a process whereby double-stranded RNA (dsRNA, also referred to herein as siRNAs or ds siRNAs, for double-stranded small interfering RNAs) induces the sequence-specific degradation of homologous mRNA in animals and plant cells. In mammalian cells, RNAi can be triggered by 21-nucleotide (nt) duplexes of small interfering RNA (sRNA), or by micro-RNAs (miRNA), functional small-hairpin RNA (shRNA), or other dsRNAs which are expressed in vivo using DNA templates with RNA polymerase III promoters.

The nucleic acid molecules or constructs can include dsRNA molecules comprising 16-30, e.g., 16, 17, 18, 19, 20, 21, 22, 23, 24, 25, 26, 27, 28, 29, or nucleotides in each strand, wherein one of the strands is substantially identical, e.g., at least 80% (or more, e.g., 85%, 90%, 95%, 99% or 100%) identical, e.g., having 3, 2, 1, or 0 mismatched nucleotide(s), to a target region in the mRNA, and the other strand is complementary to the first strand. The dsRNA molecules can be chemically synthesized, or can transcribed in vitro from a DNA template, or in vivo from, e.g., shRNA. The dsRNA molecules can be designed using any method known in the art; a number of algorithms are known, and are commercially available. Gene walk methods can be used to optimize the inhibitory activity of the sRNA.

According to some embodiments, an OPN RNAi nucleic acid inhibits the expression of all five OPN isoforms. According to some embodiments, an OPN RNAi nucleic acid selectively inhibits 1, 2, 3 or 4 OPN isoforms. According to some embodiments, an OPN RNAi nucleic acid selectively inhibits OPNc.

An exemplary target sequence of rat OPN mRNA is: 5'-CAAGCTAGTCCTAGACCCTAA-3' (SEQ ID NO: 19). An exemplary target sequence of rat lactadherin mRNA is: 5'-CAGGATGAAAGCGGAACCGGA-3' (SEQ ID NO: 20). The corresponding sequences in the human genes may be used as target sequences for inhibiting the expression of the human proteins.

According to some embodiments, an inhibitory nucleic acid targeting the GM-CSF receptor inhibits the expression of the α chain, so as not to affect the expression of the receptor to IL-3 and IL-5. According to some embodiments, an inhibitory nucleic acid targeting GM-CSF receptor inhibits the expression of the βc chain, such as to also block expression of the IL-3 and IL-5 receptors.

Exemplary oligonucleotides forming a shRNA for inhibiting the expression of GM-CSF is provided in the Examples.

Several tools for choosing target sequences for constructing RNAi nucleic acids, e.g., siRNAs, for a particular human gene are available on the world wide web. The web sites also provide tools for designing other RNA based inhibitor molecules. Such tools may take into consideration the percentage of G/C, the siRNA size, the thermodynamic properties of siRNAs, the starting nucleotide, and any homology with genome or RNA sequences.

Exemplary hairpin inserts for each of the above OPN and lactadherin siRNA target sequences are as follows:

```
RAT OPN siRNA:
sense:
                                     (SEQ ID NO: 35)
5'-r(AGC UAG UCC UAG ACC CUA A)dTdT-3' antisense:
                                     (SEQ ID NO: 36)
5'-r(UUA GGG UCU AGG ACU AGC U)dTdG-3'

RAT lactadherin siRNA:
sense
                                     (SEQ ID NO: 37)
5'-r(GGA UGA AAG CGG AAC CGG A)dTdT antisense
                                     (SEQ ID NO: 38)
5'-r(UCC GGU UCC GCU UUC AUC C)dTdG
```

Exemplary methods comprise inhibiting the expression of an integrin ligand, e.g., OPN, in a cell or tissue, e.g., in a human subject, comprising exposing or contacting (or administering into) the cell or tissue an effective amount of an inhibitory nucleic acid, such as an siRNA, comprising a nucleotide sequence that is complementary to a nucleotide sequence encoding the integrin ligand.

Exemplary hairpin inserts for inhibiting human GM-CSF are as follows:

```
Sense:
                                     (SEQ ID NO: 39)
5'GATCCAAAGAGAACCTGAAGGACTTTTCAAGAGAAAGTCCTTCAGGTT
CTCTTTGTTTTTTGGAAA'3.

Antisense:
                                     (SEQ ID NO: 40)
5'AGCTTTTCCAAAAAACAAAGAGAACCTGAAGGACTTTCTCTTGAAAAG
TCCTTCAGGTTCTCTTTG'3
```

Exemplary hairpin inserts for inhibiting human GM-CSF receptor are as follows:

```
Sense:
                                     (SEQ ID NO: 41)
5'GATCCCCGGACAGCCCTGTGGCTATATTCAAGAGATATAGCCACAGGG
CTGTCCTTTTTTGGAAG'3
```

-continued

Antisense:
(SEQ ID NO: 42)
5'TCGACTTCCAAAAAAGGACAGCCCTGTGGCTATATCTCTTGAATATAG
CCACAGGGCTGTCCGGG'3

Disclosed in Scherr M et al. Oligonucleotides; 13(5):353-63; 2003).

Exemplary methods comprise inhibiting the expression of GM-CSF or GM-CSF receptor in a cell or tissue (e.g., in a tumor for GM-CSF and in a macrophage or microglia for GM-CSF receptor), e.g., in a human subject, comprising exposing or contacting (or administering into) the cell or tissue an effective amount of an inhibitory nucleic acid, such as an siRNA, comprising a nucleotide sequence that is complementary to a nucleotide sequence encoding GM-CSF or GM-CSF receptor.

Nucleic acid compositions may include both siRNA and modified siRNA derivatives, e.g., siRNAs modified to alter a property such as the pharmacokinetics of the composition, for example, to increase half-life in the body, increase nuclease resistance, as well as engineered RNAi precursors. Various siRNA modifications are described in U.S. 20050176667, incorporated herein by reference.

RNAi nucleic acids, e.g., siRNAs, can be delivered into cells by methods known in the art, e.g., cationic liposome transfection and electroporation. siRNA duplexes can be expressed within cells from engineered RNAi precursors, e.g., recombinant DNA constructs using mammalian Pol III promoter systems (e.g., H1 or U6/snRNA promoter systems capable of expressing functional double-stranded siRNAs. The siRNA is complementary to the sequence of the target gene in 5'-3' and 3'-5' orientations, and the two strands of the siRNA can be expressed in the same construct or in separate constructs. Constructs containing siRNA sequence under the control of T7 promoter also make functional siRNAs when co-transfected into the cells with a vector expressing T7 RNA polymerase.

B) Integrin Ligand, GM-CSF and GM-CSF Receptor Antisense Molecules

According to some embodiments, an integrin ligand, e.g., OPN, is inhibited by one or more integrin ligand antisense molecules.

According to some embodiments, GM-CSF or GM-CSF receptor is inhibited by one or more GM-CSF or GM-CSF receptor antisense molecules, respectively.

An "antisense" nucleic acid can include a nucleotide sequence that is complementary to a "sense" nucleic acid encoding a protein, e.g., complementary to the coding strand of a double-stranded cDNA molecule or complementary to an integrin ligand mRNA sequence. The antisense nucleic acid can be complementary to an entire coding strand of a target sequence, e.g., an mRNA, or to only a portion thereof. According to some embodiments, the antisense nucleic acid molecule is antisense to a "noncoding region" of the coding strand of a nucleotide sequence (e.g., the 5' and 3' untranslated regions). For example, the antisense oligonucleotide can be complementary to the region surrounding the translation start site of the target mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation.

Based upon the sequences disclosed herein, one of skill in the art can choose and synthesize any of a number of appropriate antisense molecules for use in accordance with the present invention. For example, a "gene walk" comprising a series of oligonucleotides of 15-30 nucleotides spanning the length of a target nucleic acid can be prepared, followed by testing for inhibition of target gene expression. Optionally, gaps of 5-10 nucleotides can be left between the oligonucleotides to reduce the number of oligonucleotides synthesized and tested.

Similarly to RNAi nucleic acids, a person of skill in the art would be able to design antisense molecules that target all or only a subset of the OPN isoforms.

According to some embodiments, the antisense nucleic acid molecule is an α-anomeric nucleic acid molecule. An α-anomeric nucleic acid molecule forms specific double-stranded hybrids with complementary RNA in which, contrary to the usual β-units, the strands run parallel to each other. The antisense nucleic acid molecule can also comprise a 2'-o-methylribonucleotide or a chimeric RNA-DNA analogue.

According to some embodiments, the antisense nucleic acid is a morpholino oligonucleotide.

Target gene expression can also be inhibited by targeting nucleotide sequences complementary to a regulatory region (e.g., promoters and/or enhancers) to form triple helical structures that prevent transcription of the Spt5 gene in target cells. The potential sequences that can be targeted for triple helix formation can be increased by creating a so called "switchback" nucleic acid molecule. Switchback molecules are synthesized in an alternating 5'-3',3'-5' manner, such that they base pair with a first strand of a duplex and then the other, eliminating the necessity for a sizeable stretch of either purines or pyrimidines to be present on one strand of a duplex.

C) Integrin Ligand, GM-CSF and GM-CSF Receptor Ribozymes

According to some embodiments, an integrin ligand, e.g., OPN, is inhibited by one or more integrin ligand ribozyme.

According to some embodiments, GM-CSF or GM-CSF receptor is inhibited by one or more GM-CSF or GM-CSF receptor ribozyme, respectively.

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for an integrin ligand nucleic acid can include one or more sequences complementary to the nucleotide sequence of an integrin ligand nucleic acid, such as an integrin ligand gene, and a sequence having known catalytic sequence responsible for mRNA cleavage. A ribozyme having specificity for a GM-CSF nucleic acid can include one or more sequences complementary to the nucleotide sequence of a GM-CSF nucleic acid, such as a GM-CSF gene and a sequence having known catalytic sequence responsible for mRNA cleavage.

Similarly to RNAi and antisense nucleic acids, a person of skill in the art would be able to design ribozymes that target all or only a subset of the OPN isoforms.

D) Integrin Ligand, GM-CSF and GM-CSF Receptor Aptamers

Aptamers are short oligonucleotide sequences which can specifically bind specific proteins. It has been demonstrated that different aptameric sequences can bind specifically to different proteins. Methods for selection and preparation of such RNA aptamers are known in the art.

E) DNA Enzyme Targeting Integrin Ligands, GM-CSF or GM-CSF Receptor

According to some embodiments, the expression of a nucleic acid encoding an integrin ligand, is inhibited or reduced by a DNA enzyme that targets the transcript of the integrin ligand gene.

According to some embodiments, the expression of a nucleic acid encoding a GM-CSF or GM-CSF receptor, is inhibited or reduced by a DNA enzyme that targets the transcript of the GM-CSF or GM-CSF receptor gene, respectively.

A DNA enzyme is a magnesium-dependent catalytic nucleic acid composed of DNA that can selectively bind to an RNA substrate by Watson-Crick base-pairing and potentially cleave a phosphodiester bond of the backbone of the RNA substrate at any purine-pyrimidine junction. A DNA enzyme is composed of two distinct functional domains: a 15-nucleotide catalytic core that carries out phosphodiester bond cleavage, and two hybridization arms flanking the catalytic core; the sequence identity of the arms can be tailored to achieve complementary base-pairing with target RNA substrates.

The DNA enzyme will therefore have complementary regions that can anneal with regions on the transcript of an integrin gene, a GM-CSF or GM-CSF receptor gene flanking a purine-pyrimidine junction such that the catalytic core of the DNA enzyme is able to cleave the transcript at the junction, rendering the transcript unable to be translated to produce a functional integrin ligand protein/GM-CSF or GM-CSF protein.

The DNA enzyme may be synthesized using standard techniques known in the art, for example, standard phosphoramidite chemical ligation methods may be used to synthesize the DNA molecule in the 3' to 5' direction on a solid support, including using an automated nucleic acid synthesizer. Alternatively, the DNA enzyme may be synthesized by transcribing a nucleic acid molecule encoding the DNA enzyme. The nucleic acid molecule may be contained within a DNA or RNA vector, for delivery into a cellular expression system, for example, a viral vector. Suitable viral vectors include vaccinia viral vectors and adenoviral vectors.

Accordingly, an integrin ligand or GM-CSF/GM-CSF receptor may be inhibited in a cell or tissue by a method comprising exposing the cell or tissue to the DNA enzyme so that the DNA enzyme is taken up by the cell, and is able to target and cleave an integrin ligand or GM-CSF/GM-CSF receptor transcript in the cell, resulting in decreased or no expression of functional integrin ligand protein in the cell or tissue. Exposure may include exposing the cell to the naked DNA enzyme, as cells may take up naked DNA in vivo. Alternatively, if the DNA enzyme is included in a nucleic acid vector, such as a viral vector, the cell may be infected with the viral vector.

Small Molecule Integrin Ligand, GM-CSF and GM-CSF Receptor Inhibitors

According to some embodiments, the therapeutics for treating tumors having infiltrating macrophages with pro-tumor activity are small molecules or "inhibitory small molecular chemical compounds." The small molecule therapeutic may inhibit or reduce the expression or activity of an integrin ligand or of GM-CSF. The small molecule therapeutic may inhibit or reduce the interaction between an integrin ligand and an integrin, or reduce the interaction between GM-CSF and GM-CSF receptor. The small molecule therapeutic may also inhibit or reduce the signal transduction pathway that is activated by the binding of the integrin ligand to the integrin on the macrophage or microglia, or reduce the signal transduction pathway that is activated by the binding of GM-CSF to the GM-CSF receptor on the macrophage or microglia. For example, known inhibitors of FAK, JAK2 and Akt may be used for treating tumors with infiltrating macrophages with pro-tumor activity.

Small molecule therapeutics may also be identified using screening assays, e.g., as further described herein. Small molecule therapeutics may be any type of molecule, e.g., those described in the section on screening assays.

Therapeutic Administration and Pharmaceutical Compositions

Provided herein are methods for treating subjects having tumors that are infiltrated with brain resident (microglia) and peripheral macrophages, having pro-tumoral activity. The term "macrophages" is used herein to encompass brain resident (microglia) and peripheral macrophages. The method may comprise administering to a subject in need thereof a therapeutically effective amount of an integrin ligand inhibitor, to thereby reduce the pro-tumoral activity of the macrophages in the tumor of the subject. According to some embodiments, an integrin ligand inhibitor is administered locally, e.g., in a tumor, or systemically. The methods may maintain or stabilize the tumor size, or reduce the tumor size by at least 10%, 20%, 30%, 40%, 50%, 60%, 70%, 80%, 90% or more.

The term "treating" refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of spread or development of the disease or condition, delay or slowing of disease progression, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently.

The subject in need of treatment or prevention may be a human. The subject may be a subject who has a tumor, such as a subject who has cancer. Tumors that can be treated according to the methods described herein include tumors that are infiltrated by macrophages having pro-tumoral activity. "Pro-tumoral" activity of macrophages refers to the ability of certain macrophages to contribute to the development of a tumor by, e.g., participation in matrix remodeling, invasion, angiogenesis and suppression of adaptive immunity, rather than initiating anti-tumor responses. Macrophages having pro-tumoral activity are sometimes referred to as having an "M2-like phenotype." Exemplary tumors that contain infiltrating macrophages with pro-tumor activity are brain tumors, such as malignant gliomas. The glioma may be an ependymoma, an astrocytoma (e.g., glioblastoma multiforme), an oligodendroglioma or an oligoastrocytoma. The glioma may be a low-grade glioma or a high grade glioma. The glioma may also be a supratentorial glioma, an infratentorial glioma or a pontine glioma.

According to some embodiments, the methods described herein include determining whether a subject has a tumor, such as a malignant tumor. According to some embodiments, the methods described herein include determining whether a subject has a tumor that is infiltrated by macrophages that have pro-tumor activity. According to some embodiments, the method comprises first determining whether a subject has glioma. Once such a determination has been made, the present methods may include administration of an integrin ligand inhibitor, such as an OPN or lactadherin inhibitor, to the subject in an amount that is therapeutically effective to treat the subject by, e.g., stabilizing the tumor or reducing its size.

According to some embodiments, the methods described herein include determining whether a subject has a tumor that secretes abnormally high levels of GM-CSF. This may include determining whether the tumor or surrounding environment of the tumor contains more GM-CSF than is found in the same or similar tissue of a healthy subject. The method may comprise determining whether the subject has a level of serum GM-CSF that is at least 40 pg/ml, at least 50 pg/ml, at least 70 pg/ml, at least 100 pg/ml, at least 200 pg/ml, at least 300 pg/ml, at least 400 pg/ml or at least 500 pg/ml. According to some embodiments, the method comprises first determining whether a subject has glioma. The method may also include determining whether a subject has a glioma that secretes high levels of GM-CSF. Once one or more of the above determinations have been made, the present methods may include administration of a GM-CSF inhibitor to the subject in an amount that is therapeutically effective to treat the subject by, e.g., stabilizing the tumor or reducing its size.

The inhibitory nucleic acid molecules described herein can be administered to a subject (e.g., by direct injection at a tissue site), or generated in situ such that they hybridize with or bind to cellular mRNA and/or genomic DNA encoding a target protein, e.g., OPN, lactadherin or GM-CSF/GM-CSF receptor, to thereby inhibit expression of the protein, e.g., by inhibiting transcription and/or translation. Alternatively, inhibitory nucleic acid molecules can be modified to target selected cells and then administered systemically. For systemic administration, inhibitory nucleic acid molecules can be modified such that they specifically bind to receptors or antigens expressed on a selected cell surface, e.g., by linking the inhibitory nucleic acid nucleic acid molecules, or a delivery vehicle, such as a liposome, encompassing these, to a peptide or antibody that binds to a cell surface receptor or antigen. The inhibitory nucleic acid molecules can also be delivered to cells using the vectors. To achieve sufficient intracellular concentrations of the inhibitory nucleic acid molecules, vector constructs in which the inhibitory nucleic acid nucleic acid molecule is placed under the control of a strong promoter can be used. Carriers such as liposomes and others that induce internalization may also be used.

A therapeutic, e.g., an integrin ligand inhibitor or a GM-CSF inhibitor, may be administered to a patient using standard techniques known in the art. The therapeutic may be administered systemically, or may be administered directly at the site at which a target cell is located, e.g., the brain. Delivery to the site includes topical administration, injection to the site, or surgical implantation, for example in white adipose tissue.

The concentration and amount of the therapeutic to be administered will vary, depending on the disorder to be treated, the type of therapeutic that is administered, the mode of administration, and the age and health of the patient. However, a person of skill in the art will be able to determine the proper amount.

To aid in administration, the therapeutic may be formulated as an ingredient in a pharmaceutical composition. Therefore, in a further embodiment, there is provided a pharmaceutical composition comprising a therapeutic, and a pharmaceutically acceptable diluent. Therefore, also provided herein are pharmaceutical compositions for use in treating a disorder, such as cancer. The compositions may routinely contain pharmaceutically acceptable concentrations of salt, buffering agents, preservatives and various compatible carriers. For all forms of delivery, the therapeutic may be formulated in a physiological salt solution. Therapeutics may be incorporated in a liposome or other biomaterial useful for protecting and/or preserving the therapeutic until it is delivered to the target cell. The liposome may also help target a therapeutic to a desired location, e.g., a tumor.

The pharmaceutical composition may additionally contain other therapeutic agents useful for treating a disorder, such as other agents for treating cancer. According to some embodiments, one or more other agents that inhibit or reduce the pro-tumoral activity of infiltrating macrophages with pro-tumor activity are administered. Such agents include inhibitors of hepatocyte growth factor (HGF); inhibitors of monocyte chemotactic protein (MCP1); inhibitors of MCP3 and inhibitors of CXCRL1-CXCR1.

According to some embodiments, the present invention relates to administration of a pharmaceutically acceptable formulation of an inhibitor of an integrin ligand. According to some embodiments, the present invention relates to the administration of a pharmaceutically acceptable formulation of an inhibitor of GM-CSF or GM-CSF receptor. A "pharmaceutically acceptable formulation" is one that is suitable for administering the integrin ligand inhibitor in a manner that gives the desired results and does not also produce adverse side effects sufficient to convince a physician that the potential harm to a patient is greater than the potential benefit to that patient.

According to some embodiments, the method described herein comprises administering an integrin ligand inhibitor together with a GM-CSF inhibitor. According to some embodiments, a method comprises administering to a subject having a glioma or likely to develop a glioma, a therapeutically effective amount of an integrin ligand inhibitor, such as osteopontin inhibitor or a lactadherin inhibitor and a GM-CSF inhibitor and. According to some embodiments, a method a method comprises administering to a subject having a glioma or likely to develop a glioma, a therapeutically effective amount of an osteopontin inhibitor and a lactadherin inhibitor together with a GM-CSF inhibitor. The method may first comprise determining the level of GM-CSF, osteopontin and/or lactadherin in a sample of a subject having a glioma, and if the level of GM-CSF, osteopontin and/or lactadherin is above a level that is associated with a glioma, such as an aggressive form of a glioma, then administering a GM-CSF inhibitor in combination with an integrin ligand inhibitor, such as an osteopontin inhibitor and/or a lactadherin inhibitor.

The pharmaceutical composition of the present invention may be prepared by known methods for the preparation of pharmaceutically acceptable compositions suitable for administration to patients, such that an effective quantity of the therapeutic, and any additional active substance or substances, is combined in a mixture with a pharmaceutically acceptable vehicle. On this basis, the pharmaceutical compositions include, albeit not exclusively, solutions of the therapeutic in association with one or more pharmaceutically acceptable vehicles or diluents, and contained in buffer solutions with a suitable pH and iso-osmotic with physiological fluids.

The proportion and identity of a pharmaceutically acceptable diluent used with a therapeutic is determined by the chosen route of administration, compatibility with live cells, and standard pharmaceutical practice. Generally, a pharmaceutical composition will be formulated with components that will not kill or significantly impair the biological properties of the therapeutic.

The pharmaceutical composition of the present invention may be administered to a patient in a variety of forms depending on the selected route of administration, as will be understood by those skilled in the art. For example, a composition may be administered topically, surgically or by injection to the desired site. According to some embodiments, a therapeutic is administered topically or by injection (subcutaneously, intravenously, intramuscularly, etc.) directly at the desired site where the target cells, e.g., white adipose cells, are located in the patient.

Exemplary Diagnostics and Biomarker Applications

Also provided herein are diagnostic, prognostic and biomarker based methods and compositions. Methods may be based on determining the level of an integrin ligand, e.g., OPN or lactadherin and/or determining the level of GM-CSF. The level of an integrin ligand and/or GM-CSF in a sample, may be determined by a variety of methods, such as ELISAs or Western Blots, using, e.g., an antibody that bind specifically to the integrin ligand. The method may also rely on determining the level, or number, of tumor infiltrating macrophages or microglia cells that have pro-tumor activity. Macrophages or microglia may be isolated and identified based on the cell surface markers that are present on macrophages or microglia with pro-tumor activity, but not on those that do not have pro-tumor activity. Exemplary markers are further described herein.

Assays may also be based on determining the level of mRNA of integrin ligands and/or GM-CSF, e.g., in the tumor cells, instead of, or in addition to, determining the level of the respective proteins.

Methods may include obtaining a tissue sample from a subject. A tissue sample may be a tumor sample, a brain or central nervous system (CNS) sample, e.g., a sample obtained from a glioma tumor. The sample may also be a sample of blood or serum or other bodily fluid.

The present invention provides a method for determining whether a subject having a glioma tumor is responsive to a therapeutic for treating the glioma tumor comprising providing a sample of a glioma tumor of the subject and determining the level or activity of OPN or lactadherin in a glioma tumor of the subject, wherein
  (i) a lower level or activity of OPN or lactadherin in the sample relative to the level or activity of OPN or lactadherin in the glioma at an earlier time of the treatment with the therapeutic, or before the beginning of the treatment with the therapeutic indicates that the treatment has a positive outcome; and
  (ii) a higher level or activity of OPN or lactadherin in the sample relative to the level or activity of OPN or lactadherin in the glioma at an earlier time of the treatment with the therapeutic, or before the beginning of the treatment with the therapeutic indicates that the treatment does not have a positive outcome.

The present invention further provides a method for determining whether a subject having a glioma tumor is responsive to a therapeutic for treating the glioma tumor comprising providing a sample of a glioma tumor of the subject and determining the level or activity of a molecule in the signaling pathway that is activated in a macrophage or microglia by the binding of OPN or lactadherin to a receptor on the macrophage or microglia, wherein
  (i) a lower level or activity of the molecule in the sample relative to the level or activity of molecule in the glioma at an earlier time of the treatment with the therapeutic, or before the beginning of the treatment with the therapeutic indicates that the treatment has a positive outcome; and
  (ii) a higher level or activity of the molecule in the sample relative to the level or activity of the molecule in the glioma at an earlier time of the treatment with the therapeutic, or before the beginning of the treatment with the therapeutic indicates that the treatment does not have a positive outcome.

The present invention further provides a method for determining whether a subject having a glioma tumor is responsive to a therapeutic for treating the glioma tumor comprising providing a sample of a glioma tumor of the subject and determining the level of macrophages or microglia that have pro-tumor activity in the sample, wherein
  (i) a lower level of macrophages or microglia that have pro-tumor activity in the sample relative to the level of macrophages or microglia that have pro-tumor activity in the glioma at an earlier time of the treatment with the therapeutic, or before the beginning of the treatment with the therapeutic indicates that the treatment has a positive outcome; and
  (ii) a higher level of macrophages or microglia that have pro-tumor activity in the sample relative to the level of macrophages or microglia that have pro-tumor activity in the glioma at an earlier time of the treatment with the therapeutic, or before the beginning of the treatment with the therapeutic indicates that the treatment has a negative outcome.

A therapeutic may be an integrin ligand inhibitor, such as an OPN or lactadherin inhibitor, e.g., as further described herein.

The present invention further provides a method for determining the prognosis of a subject having a glioma tumor comprising providing a sample of a glioma tumor of the subject and determining the level or activity of OPN or lactadherin in a glioma tumor of the subject, wherein
  (i) a lower level or activity of OPN or lactadherin in the sample relative to the level or activity of OPN or lactadherin in the glioma at an earlier time indicates that the prognosis is favorable; and
  (ii) a higher level or activity of OPN or lactadherin in the sample relative to the level or activity of OPN or lactadherin in the glioma at an earlier time indicates that the prognosis is not favorable.

The present invention further provides a method for determining prognosis of a subject having a glioma tumor comprising providing a sample of a glioma tumor of the subject and determining the level or activity of a molecule in the signaling pathway that is activated in a macrophage or microglia by the binding of OPN or lactadherin to a receptor on the macrophage or microglia, wherein (i) a lower level or activity of the molecule in the sample relative to the level or activity of molecule in the glioma at an earlier time indicates that the prognosis is favorable; and
(ii) a higher level or activity of the molecule in the sample relative to the level or activity of the molecule in the glioma at an earlier time indicates that the prognosis is not favorable.

The present invention further provides a method for determining the prognosis of a subject having a glioma tumor comprising providing a sample of a glioma tumor of the subject and determining the level of macrophages or microglia that have pro-tumor activity in the sample, wherein
(i) a lower level of macrophages or microglia that have pro-tumor activity in the sample relative to the level of macrophages or microglia that have pro-tumor activity in the glioma at an earlier time indicates that the treatment has a positive outcome; and
(ii) a higher level of macrophages or microglia that have pro-tumor activity in the sample relative to the level of macrophages or microglia that have pro-tumor activity in the glioma at an earlier time indicates that the prognosis is not favorable.

The present invention further provides a method for determining the prognostic of a subject having a glioma tumor comprising providing a sample of a glioma tumor of the subject; and determining the level or activity of OPN or lactadherin in the sample, wherein a level or activity of OPN or lactadherin that is lower than a control value (e.g., ≤20 ng/mL) indicates that the prognostic of the subject is favorable, whereas a level or activity of OPN or lactadherin that is higher (e.g., >20 ng/mL) than a control value indicates that the prognosis is not favorable.

The present invention further provides a method for determining the prognostic of a subject having a glioma tumor comprising providing a sample of a glioma tumor of the subject; and determining the level or activity of a molecule in the signaling pathway that is activated in a macrophage or microglia by the binding of OPN or lactadherin to an integrin on the macrophage or microglia in the sample, wherein a level or activity of the molecule that is lower than a control value indicates that the prognostic of the subject is favorable, whereas a level or activity of the molecule that is higher than a control value indicates that the prognostic of the subject is not favorable.

The present invention further provides a method for determining the prognostic of a subject having a glioma tumor comprising providing a sample of a glioma tumor of the subject; and determining the level of macrophages or microglia that have pro-tumor activity in the sample, wherein a level of macrophages or microglia that have pro-tumor activity in the sample that is lower than a control value indicates that the prognostic of the subject is favorable, whereas a level of macrophages or microglia that have pro-tumor activity in the sample that is higher than a control value indicates that the prognosis is not favorable.

A control value may be a value that is the average (e.g., statistically significant) of the level of macrophages or microglia that have pro-tumor activity in subject who were found to have a good prognostic, e.g., a glioma that has stabilized, regressed or is progressing only slowly relative to other gliomas. the control value for OPN and lactadherin levels may be 20 ng/mL.

Also provided are methods for identifying tumors that are associated with infiltrating macrophages, e.g., having pro-tumor activity. The method may comprise providing a tumor sample, e.g., a glioma sample, and determining the level or activity (e.g., state of phosphorylation) of one or more signal transduction pathway molecules whose level or activity is modulated by the binding of an integrin ligand, e.g., OPN or lactadherin, to a receptor, e.g., an integrin. An elevated level of such a marker indicates the presence of tumor infiltrating macrophages or microglia with pro-tumor activity.

Further provided are diagnostic methods for determining the presence of a tumor having infiltrating macrophages with pro-tumor activity. The method may comprising providing a tissue sample of a subject, such as a brain sample or a tumor sample, and determining the level of integrin ligand, e.g., OPN or lactadherin. The presence of the integrin ligand indicates the presence of a tumor and a poor prognosis and may also indicate the presence of infiltrating macrophages or microglia with pro-tumor activity. According to some embodiments, the presence of OPN or lactadherin in a sample indicates that the tissue, e.g., tumor, comprises macrophages or microglia having pro-tumor (or pro-invasive) rather than anti-inflammatory activity.

The presence of OPN or lactadherin in a tissue sample of a subject, such as a brain sample, may also indicate the presence in the subject of a brain tumor, e.g., a glioma. In one embodiment, a method comprises providing a brain tissue sample of a subject and determining the level of OPN or lactadherin in the brain tissue sample, wherein a statistically significantly higher level of OPN or lactadherin in the brain tissue sample of the subject relative to a control subject who does not have glioma indicates that the subject has or is likely to develop a glioma.

The present invention further provides a method for determining the prognosis of a subject having a tumor, e.g., a glioma, comprising providing a sample of the subject having the tumor, and determining the level of GM-CSF in the sample, wherein
(i) a higher level of GM-CSF in the sample of the subject having a tumor relative to the level in a subject that does not have a tumor indicates that the subject has a poor prognosis; and
(ii) a lower or similar level of GM-CSF in the sample of the subject having a tumor relative to the level in a subject that does not have a tumor indicates that the subject has a good prognosis.

The sample may be a brain sample, a tumor sample a sample of tissue or fluid in the vicinity of the tumor (e.g., intracranial fluid), or blood or serum sample. The tumor may be a glioma, e.g., glioma multiforme. The method may comprise determining the level of GM-CSF protein or the level of GM-CSF nucleic acid, e.g., RNA, such as mRNA. The level of GM-CSF protein is undetectable in healthy subjects; and a level of GM-CSF equal to or above 40 pg/ml indicates an abnormal condition, e.g., the presence of a tumor, asthma, worm infection or neurorepair. Thus, the level of GM-CSF in a subject that does not have a tumor is <40 pg/ml. GM-CSF in GBMs (1.23±0.37 pg/ml; p<0.0001) compared with the healthy control group (0.09±0.11 pg/ml (Afat et al. J Neurosurg. 2010, 112(1):43-9).

As described herein, the level of GM-CSF is up-regulated 3-5 fold in low grade gliomas and more than 200 fold in high grade gliomas. Accordingly, also provided herein is a method for determining the prognosis (or severity of disease) of a subject having a tumor, e.g., a glioma, comprising providing a sample of the subject having the tumor, and determining the level of GM-CSF in the sample, wherein
(i) a level of GM-CSF in the sample of the subject having a tumor that is at least 100 fold, 150 fold, or 200 fold higher relative to the level in a subject that does not have a tumor indicates that the subject has a poor prognosis; and (ii) a level of GM-CSF in the sample of the subject having a tumor that is similar to or lower than the level in a subject that does not have a tumor indicates that the subject has a good prognosis.

The present invention further provides a method for determining the prognosis of a subject having a tumor, e.g., a glioma, comprising providing a serum sample of the subject having the tumor, and determining the level of GM-CSF in the sample, wherein (i) a level of GM-CSF in the serum sample of the subject having a tumor that is higher than 100 pg/ml, 150 pg/ml, 200 pg/ml, 300 pg/ml, 400 pg/ml, or 500 pg/ml indicates that the subject has a poor prognosis; and (ii) a level of GM-CSF in the serum sample of the subject having a tumor that is lower than 100 pg/ml, 70 pg/ml, 50 pg/ml, or 40 pg/ml indicates that the subject has a good prognosis.

Also provided herein are methods for determining the severity (or aggressiveness) of a tumor in a subject, comprising providing a serum sample of the subject having the tumor, and determining the level of GM-CSF in the sample, wherein (i) a level of GM-CSF in the serum sample of the subject having a tumor that is higher than 100 pg/ml, 150 pg/ml, 200 pg/ml, 300 pg/ml, 400 pg/ml, or 500 pg/ml indicates that the subject has an aggressive tumor, e.g., a high grade glioma; and (ii) a level of GM-CSF in the serum sample of the subject having a tumor that is lower than 100 pg/ml, 70 pg/ml, 50 pg/ml, or 40 pg/ml indicates that the subject does not have an aggressive tumor and may have, e.g., only a low grade glioma.

The methods of the invention may also comprise determining the level of signal transduction through the GM-CSF level as a manner of measuring the level of GM-CSF. The method may also comprise determining the level of a signal transduction molecule that is activated by the binding of GM-CSF to its receptor, as a measure for determining the level of GM-CSF. A molecule may be JAK2, such as activated JAK2. An exemplary method is as follows:

The present invention further provides a method for determining the prognosis (or severity of disease) of a subject having a tumor, e.g., a glioma, comprising providing a sample of the subject having the tumor, and determining the level of activated GM-CSF signal transduction molecule (e.g., activated or phosphorylated JAK2) in the sample, wherein (i) a higher level of activated GM-CSF signal transduction molecule in the sample of the subject having a tumor relative to the level in a subject that does not have a tumor indicates that the subject has a poor prognosis; and (ii) a lower or similar level of activated GM-CSF signal transduction molecule in the sample of the subject having a tumor relative to the level in a subject that does not have a tumor indicates that the subject has a good prognosis.

The present invention further provides a method for determining the prognosis of a subject having a glioma tumor comprising providing a sample of a glioma tumor of the subject; and determining the level of GM-CSF in the sample, wherein a level of GM-CSF that is lower than a control value indicates that the prognosis of the subject is favorable, whereas a level of GM-CSF that is higher than a control value indicates that the prognosis is not favorable. The control value may be a value that is the average (e.g., statistically significant) of the level in subject who were found to have a good prognosis, e.g., a glioma that has stabilized, regressed or is progressing only slowly relative to other gliomas. The control value for GM-CSF levels may be 50 pg/ml, 40 pg/ml, or 15 pg/mL.

The present invention further provides a method for determining whether a subject having a tumor, e.g., a glioma, is responsive to a therapeutic for treating the tumor comprising providing a sample of a the subject and determining the level or activity of GM-CSF in the sample of the subject, wherein (iii) a lower level or activity of GM-CSF in the sample relative to the level or activity of GM-CSF in a sample at an earlier time of the treatment with the therapeutic, or before the beginning of the treatment with the therapeutic indicates that the treatment has a positive outcome; and (iv) a higher level or activity of GM-CSF in the sample relative to the level or activity of GM-CSF in a sample at an earlier time of the treatment with the therapeutic, or before the beginning of the treatment with the therapeutic indicates that the treatment does not have a positive outcome.

The present invention further provides a method for determining whether a subject having a tumor, e.g., a glioma, is responsive to a therapeutic for treating the tumor comprising providing a sample of a tumor of the subject and determining the level or activity of a molecule in the signaling pathway that is activated in a macrophage or microglia by the binding of GM-CSF to the GM-CSF receptor on the macrophage or microglia, wherein (iii) a lower level or activity of the molecule in the sample relative to the level or activity of molecule in the tumor or in the vicinity of the tumor at an earlier time of the treatment with the therapeutic, or before the beginning of the treatment with the therapeutic indicates that the treatment has a positive outcome; and (iv) a higher level or activity of the molecule in the sample relative to the level or activity of the molecule in the tumor or the vicinity of the tumor at an earlier time of the treatment with the therapeutic, or before the beginning of the treatment with the therapeutic indicates that the treatment does not have a positive outcome.

The molecule may be JAK2, such as activated or phosphorylated JAK2.

Also provided are methods for identifying a subject who may be treated as described herein, e.g., by administration of a GM-CSF inhibitor. Methods for identifying such subjects may include obtaining a sample from the subject, e.g., a brain sample, such as a brain tumor sample or sample of intracranial fluid, or a blood or serum sample, and determining the level of GM-CSF protein or activity (e.g., activity can be determined) in the sample, wherein the presence of a level or activity of GM-CSF in the sample that is higher than a control value indicates that the subject can be treated by the administration of a GM-CSF inhibitor, whereas a level or activity of GM-CSF in the sample that is lower than a control value indicates that the subject will not likely be responsive to a treatment with a GM-CSF inhibitor. The control value may be the median or average (statistically significant) level or activity of GM-CSF in subjects who do not have a brain tumor, e.g., subjects who do not have glioma. For example, a control value, e.g., in a serum sample, may be 40 pg/ml or 100 pg/ml. Thus, e.g., a subject having a blood or serum level of GM-CSF that is higher than 40 pg/ml, 100 pg/ml, 250 pg/ml, 300 pg/ml, 400 pg/ml or 500 pg/ml can be treated by the administration of a GM-CSF inhibitor, whereas a subject having a blood or serum level of GM-CSF that is lower than 100 pg/ml or 40 pg/ml may not be responsive to a treatment with a GM-CSF inhibitor.

According to some embodiments, a method comprises determining whether a subject has a glioma, and if the subject has a glioma, then determining the level or activity of GM-CSF in a sample of the subject, e.g., a tumor sample, brain sample, or serum sample, wherein a higher level or activity of GM-CSF in the subject relative to a subject who does not have glioma or relative to a control value (e.g., 40 pg/ml, 100 pg/ml, 250 pg/ml, 300 pg/ml, 400 pg/ml or 500 pg/ml serum GM-CSF), indicates that the subject will likely respond to a treatment with a GM-CSF inhibitor, whereas a level or activity of GM-CSF in the subject that is similar to or lower that in a subject who does not have glioma or which is lower than a control value (e.g. 100 pg/ml or 40 pg/ml serum GM-CSF), indicates that the subject is not likely to respond to a treatment with a GM-CSF inhibitor.

The method for determining whether a subject is likely to respond to a treatment with a GM-CSF inhibitor may also comprise administering to the subject (e.g., a single dose of) a GM-CSF inhibitor; obtaining a sample from the subject and determining the level of GM-CSF, wherein a lower level of GM-CSF in the sample of the subject relative to its level prior to the administration of the GM-CSF inhibitor indicates that the subject is likely to respond to a treatment with a GM-CSF inhibitor, whereas a similar or higher level of GM-CSF in the sample of the subject relative to its level prior to the administration of the GM-CSF inhibitor indicates that the subject is not likely to respond to a treatment with a GM-CSF inhibitor. The method may comprise obtaining a tumor sample prior to administration of the GM-CSF inhibitor.

The method for determining whether a subject is likely to respond to a treatment with a GM-CSF inhibitor may also comprise administering to the subject (e.g., a single dose of) a GM-CSF inhibitor; obtaining a tumor sample from the subject and determining the level of invading macrophages/microglia, wherein a lower level of invading macrophages/microglia in the tumor sample of the subject relative to the level of invading macrophages/microglia in the tumor prior to the administration of the GM-CSF inhibitor indicates that the subject is likely to respond to a treatment with a GM-CSF inhibitor, whereas a similar or higher level of invading macrophages/microglia in the tumor sample of the subject relative to the level of invading macrophages/microglia in the tumor prior to the administration of the GM-CSF inhibitor indicates that the subject is not likely to respond to a treatment with a GM-CSF inhibitor. A method may comprise obtaining a tumor sample prior to administration of the GM-CSF inhibitor.

Further provided are diagnostic methods for determining the presence of a tumor producing GM-CSF, such as an aggressive glioma. The method may comprise providing a sample of a subject, such as a brain sample or a tumor sample or serum sample, and determining the level or activity of GM-CSF. The presence or activity of GM-CSF that is at least 100 fold, 150 fold, 200 fold, 250 fold, 300 fold, 400 fold or 500 fold higher than that in a subject who does not have glioma, indicates the presence of a tumor and a poor prognosis.

It is also possible to measure levels of GM-CSF within the body of a subject, using, e.g., imaging technologies that detect GM-CSF. In such instances, it is not necessary to obtain a sample from a subject.

The present invention further provides screening assays for identifying inhibitor that can inhibit the pro-tumor activity of macrophages. Screening assays include: assays based on the analysis of GCM induced actin cytoskeleton changes and fluorescent beads phagocytosis; assays based on testing the invasiveness of glioma cells in the presence or absence of microglia cells, e.g., in the Matrigel matrix invasion assay followed by DAPI staining and quantification with iCys™ Research Imaging Cytometer; expression of specific M2 type genes: Arg1, mt1-mmp, CXCL4, c-Myc, SMAD7. Those are genes selectively induced by GCM and the integrin ligands.

An exemplary screening assay may comprise contacting a macrophage or microglia that has pro-tumor activity with an integrin ligand, such as OPN (e.g., human OPN) or lactadherin (e.g., human lactadherin) or a biologically active fragment or variant thereof (e.g., comprising the RGD motif), in the presence of a test compound, and determining whether the presence of the test agent reverses at least some part of the pro-tumor activity of the macrophage or microglia. This can be determined, e.g., by measuring markers that are specific to macrophages or microglia that have pro-tumor activity and are not present (or present at a different level) in macrophages or microglia that do not have pro-tumor activity. The macrophages or microglia for use in this assay may be purified populations of cells (e.g., isolated cells or populations of cells), or they may be in a composition together with other cells, e.g., tumor cells. For example, the population of cells may comprise less or more than 10%, 20%, 30%, 40%, 50%, 60%, 70%, 80%, 90% or 95% of macrophages or microglia with pro-tumor activity. The macrophages or microglia may also be cell lines.

Therapeutic compounds may also be identified by their ability to prevent an integrin ligand, e.g. OPN or lactadherin, to mediate or contribute to changing a macrophage or microglia with anti-tumor activity into a macrophage or microglia, respectively, with pro-tumor activity. An exemplary method may comprise contacting a population of macrophages or microglia having anti-tumor activity with an integrin ligand, e.g., OPN or lactadherin, in the presence or absence of a test compound and determining whether the presence of the test compound inhibits or prevents the macrophage or microglia with anti-tumor activity to lose its anti-tumor activity and gain pro-tumor activity.

The macrophages or microglia for use in this assay may be purified populations of cells (e.g., isolated cells or populations of cells), or they may be in a composition together with other cells, e.g., tumor cells. For example, the population of cells may comprise less or more than 10%, 20%, 30%, 40%, 50%, 60%, 70%, 80%, 90% or 95% of macrophages or microglia with anti-tumor activity. The macrophages or microglia may also be cell lines.

The screening method may also comprise contacting OPN or lactadherin or a biologically active fragment or variant thereof (e.g., comprising the RGD motif) with an integrin, e.g., $\alpha V\beta 3$, in the presence or absence of a test compound, and determining whether the test compound inhibits or reduces the interaction between OPN or lactadherin, or fragment or variant thereof, and the integrin, wherein a test compound that reduces the interaction by at least 10%, 20%, 30%, 40%, 50%, 60%, 70%, 80%, 90% or 95% is an integrin ligand inhibitor that can be used in the methods described herein.

Provided herein are also screening assays useful for identifying agents that can prevent tumor progression induced by GM-CSF, angiogenesis or the recruitment of macrophages or microglia to a tumor site.

The method may comprise contacting tumor cells producing GM-CSF, e.g., glioma cells, with a test compound that inhibits at least one GM-CSF biological activity, and determining whether macrophages or microglia are recruited to the site of the tumor cells or determining whether tumor progression is slowed down. In one embodiment, an assay uses an organotypical brain slice culture, and the assay comprises adding a test compound, e.g., a test compound that inhibits at least one GM-CSF biological activity, to the culture. A reduced amount of migration of the macrophages/microglia towards the tumor cells relative to a culture in which no test compound was added indicates that the test compound is a GM-CSF inhibitor, which can be used for treating tumors secreting GM-CSF.

The method for identifying a GM-CSF inhibitor for use in the methods described herein may comprise contacting a tumor cell, e.g., a glioma cell that produces GM-CSF, with a test compound, and determining whether the production of GM-CSF by the tumor cell is slowed down. A test compound that slows down the production of GM-CSF by the tumor cell is a compound that can be used in the methods described herein for treating subjects having tumors that secrete GM-CSF, and optionally tumor invading macrophages or microglia. The tumor cells, e.g., glioma cells, for use in an assay may be purified populations of cells (e.g., isolated cells or populations of cells), or they may be in a composition together with other cells, e.g., infiltrating macrophages or microglia. For example, the population of tumor cells may comprise less or more than 10%, 20%, 30%, or 40% of macrophages or microglia. The tumor cells may also be cells of cell lines, e.g., those described in the Examples.

The screening method may also comprise contacting GM-CSF (e.g., human GM-CSF) or a biologically active fragment or variant thereof with GM-CSF receptor (soluble, or an a cell membrane), in the presence or absence of a test compound, and determining whether the test compound inhibits or reduces the interaction between GM-CSF, or fragment or variant thereof, and GM-CSF receptor, wherein a test compound that reduces the interaction by at least 10%, 20%, 30%, 40%, 50%, 60%, 70%, 80%, 90% or 95% is a GM-CSF inhibitor that can be used in the methods described herein.

The method may further include testing the identified test compound in a cell based assay or in vivo assay, such as an assay for determining whether the test compound reverses the pro-tumor activity of macrophages or prevents macrophages with anti-tumor activity to become macrophages with pro-tumor activity.

According to some embodiments, the test compounds are initially members of a library, e.g., an inorganic or organic chemical library, peptide library, oligonucleotide library, or mixed-molecule library. According to some embodiments, the methods include screening small molecules, e.g., natural products or members of a combinatorial chemistry library.

A given library can comprise a set of structurally related or unrelated test compounds. Preferably, a set of diverse molecules should be used to cover a variety of functions such as charge, aromaticity, hydrogen bonding, flexibility, size, length of side chain, hydrophobicity, and rigidity. Combinatorial techniques suitable for creating libraries are known in the art. In addition, a number of libraries, including small molecule libraries, are commercially available.

According to some embodiments, the test compounds are peptide or peptidomimetic molecules, e.g., peptide analogs including peptides comprising non-naturally occurring amino acids or having non-peptide linkages; peptidomimetics (e.g., peptoid oligomers, e.g., peptoid amide or ester analogues, .beta.-peptides, D-peptides, L-peptides, oligourea or oligocarbamate); small peptides (e.g., pentapeptides, hexapeptides, heptapeptides, octapeptides, nonapeptides, decapeptides, or larger, e.g., 20-mers or more); cyclic peptides; other non-natural or unnatural peptide-like structures; and inorganic molecules (e.g., heterocyclic ring molecules). According to some embodiments, the test compounds are nucleic acids, e.g., DNA or RNA oligonucleotides.

According to some embodiments, test compounds and libraries thereof can be obtained by systematically altering the structure of a first test compound. For example, in one embodiment, a general library of small molecules is screened, e.g., using the methods described herein, to select a fist test small molecule. Using methods known in the art, the structure of that small molecule is identified if necessary and correlated to a resulting biological activity, e.g., by a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds.

According to some embodiments, test compounds identified as "hits" (e.g., test compounds that inhibit the conversion of anti-tumor macrophages to pro-tumor macrophages or which are able to revert the pro-tumor activity of macrophages to anti-tumor activity) in a first screen are selected and optimized by being systematically altered, e.g., using rational design, to optimize binding affinity, avidity, specificity, or other parameter. Such potentially optimized structures can also be screened using the methods described herein. Thus, in one embodiment, the invention includes screening a first library of test compounds using a method described herein, identifying one or more hits in that library, subjecting those hits to systematic structural alteration to create one or more second generation compounds structurally related to the hit, and screening the second generation compound. Additional rounds of optimization can be used to identify a test compound with a desirable therapeutic profile.

Test compounds identified as hits can be considered candidate therapeutic compounds, useful in the methods of treating and preventing disorders described herein. Thus, the invention also includes compounds identified as "hits" by a method described herein, and methods for their administration and use in the treatment, prevention, or delay of development or progression of a disease described herein.

Also provided herein are kits for treating; kits for diagnostic, prognostic or biomarker uses, and kits for screening assays. The kits may comprise at least one or more of the elements used in the methods of treatment, diagnosis, prognosis, biomarker assays or screening assays.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Materials and Methods

Cell culture and treatment. Primary cultures of rat microglia were prepared from 1-day-old Wistar rat pups as described previously (Zawadzka and Kaminska 2003). Briefly, cells were isolated from cerebral cortices by trypsination, mechanically dissociated and plated at the density of $3\times10^5$ cells/cm$^2$ in Dulbecco's modified Eagle medium (with Glutamax and high-glucose formula 4.5 g/L, Gibco) supplemented with heat-inactivated 10% fetal bovine serum (Gibco), 100 U/mL penicillin, and 0.1 mg/mL streptomycin on poly-L-lysine coated culture 75 cm$^2$ flasks. Murine pEGFP-GL261 glioma cells were cultured in DMEM with 10% FBS and antibiotics (50 U/ml penicillin, 50 µg/ml streptomycin). Primary cultures of astrocytes were prepared from cerebral cortex of 2-day-old C57BL/6 newborn mice. Astrocytes were cultured in DMEM media with high glucose supplemented with 10% FBS, 100 U/ml penicillin and 100 µg/ml streptomycin. Culture medium was changed after 3 days and then twice a week. Cell cultures were maintained at 37° C. in humidified 5% $CO_2$/95% air incubator (Heraeus, Hanau, Germany). After 2 weeks the loosely adherent microglia cells were recovered from confluent glial cultures by a mild shaking and centrifugation (300 g for 5 min). In some experiments microglia cultures were treated with a 7-aminoacid synthetic peptide containing RGD motif or a control, scrambled peptide.

Immunocytochemistry.

Cells were washed with a phosphate buffer saline (PBS) and fixed with 2% paraformaldehyde at indicated time periods. Fixed cells were incubated with phalloidin tetramethylrhodamine B isothiocyanate for 30 min at room temperature. Subsequently, cells were washed with PBS and cell nuclei were visualized by DAPI staining (4,6-diamidino-2-phenylindole, Sigma-Aldrich, Saint Louis, Mo., USA, 10 µg/mL) for 10 min followed by washing 3 times with PBS. Morphological alterations were monitored by fluorescent microscopy with excitation 450-490 nm, recorded with 20× objective.

Proliferation Assay.

BrdU incorporation test was used to determine a rate of microglia proliferation. Briefly, $5\times10^4$ microglia cells were seeded onto 96-wells plate, cultured for 48 hours and then stimulated with LPS or GCM. BrdU (10 µM) was added after 24 h to the culture medium and cells were left for next 6 h. Subsequently, cells were fixed and BrdU incorporation was determined according to the manufacturer's protocol (Roche, Mannheim, Germany).

Cell Motility and Invasion Assays.

Microglia were platted on a 35 mm Petri dish at the density of $1.5\times10^6$ cells and after 48 hours the cultures were gently scratched using a pipette tip and microglia cells were cultured under various experimental conditions (control, 100 ng/mL LPS or G-CM). Motility of microglia cells was determined 3 hours after treatment. Migrating cells were visualized by phase-contrast microscopy.

The invasion assay was performed as described (Wesolowska et al. 2008, Kwiatkowska et al. 2011). Briefly, 24-well tissue culture inserts (12 µm pore size Transwell, Corning, N.Y., USA) were coated with the Growth Factor Reduced Matrigel™ Matrix (BD Biosciences, San Diego. Calif., USA). 100 µl of the Matrigel™ Matrix (1 mg/ml) diluted in distilled water, was dried under sterile conditions (37° C.) for 5-6 hours and reconstituted for 30 minutes in 200 µl of culture medium. C6 glioma cells ($1.5\times10^4$/insert) were seeded on Matrigel-coated membrane in the serum-reduced medium (2% FBS) and exposed to microglia or left untreated. After 48 h cells were fixed and cell nuclei stained with DAPI. The membranes from Transwell® inserts were cut out and the total number of cells that migrated through the Matrigel was determined using Laser Scanning Cytometry (LSC, CompuCyte). All experiments were performed in triplicate. The data from three independent experiments were pooled and expressed as the average number of cells±S.D.

Integrin Silencing.

Microglia cells ($1\times10^5$) were seeded on 24-wells plates and after 24 hours cells were transfected with 25 nM control non-targeting siRNA, and siRNA to αv or β3, or two siRNA together (ON-TARGET siRNA, Dharmacon) using 0.25 µl of DharmaFECT 3 transfection reagent in 0.5 ml culture medium. After 48 h the transfection medium was replaced by G-CM and phagocytic properties of microglia were determined as described. To estimate the silencing efficiency cells were removed from the culture plates by trypsynization and suspended in MACS buffer (PBS, 2 mM EDTA, 0.5% BSA) at final concentration $1\times10^5$ cells/100 µl. Cell surface expression of the integrins was analysed using primary antibodies to αv or β3 (BD Biosciences) and anti-mouse-Alexa Fluor 647 secondary antibody (Invitrogen). The fluorescent intensity of the labelled cells was analysed with FACSCalibur (Beckton Dickinson). The mean fluorescent intensity was compared with the control siRNA and expressed as the relative change to the control condition for each experimental siRNA.

Phagocytosis.

Phagocytic properties of microglia were determined by incubation of cells with 2 µm fluorescent latex beads (Sigma-Aldrich, Saint Louis, Mo., USA) for 90 min. Microglia were platted on a 35 mm Petri dish at the density of $1\times10^6$ cells, silenced for 48 hours, then exposed for 24 hours to different experimental conditions (control, G-CM, G-CM with 500 µM RGD-peptide or a scrambled peptide). The cells were washed twice with PBS, fixed with 2% paraformaldehyde and stained with FITC-conjugated isolectin B4. The percentage of cells with none/low (<2 beads per cell), medium (≥2<10) or high (≥10 beads per cell) phagocytic activity was counted. Alternatively, the cells were seeded on 24-wells plates at the density of $1.5\times10^5$ cells and after incubation with the beads, followed by intensive washing and fixation, the total fluorescence was measured using a microplate reader (Tecan).

Protein Isolation, Electrophoresis and Detection.

Whole cell lysates were prepared by scraping the cells into the buffer containing phosphatase and protease inhibitors (20 mM Tris HCl, pH6.8, 137 mM sodium chloride, 25 mM β-glycerophosphate, 2 mM sodium pyrophosphate, 2 mM EDTA, 1 mM sodium orthovanadate, 1% Triton X-100, 10% glycerol, 5 µg/ml leupeptin, 5 µg/ml aprotinin, 2 mM benzamidine, 0.5 mM DTT, 1 mM PMSF). The protein concentration was determined with the Bradford assay (Sigma-Aldrich, Saint Louis, Mo., USA). Protein extracts were separated on SDS-PAGE before electrophoretic transfer onto a nitrocellulose membrane (Amersham Biosciences, Germany) as described (Ellert-Miklaszewska et al. 2005; Sliwa et al. 2007). After blocking with 5% non-fat milk in TBS-T (Tris-buffered saline pH 7.6/0.15% Tween 20) the membranes were incubated with primary antibodies diluted in a blocking buffer overnight and then with relevant secondary antibodies for one hour. Antibodies recognizing phosphorylated and total forms of p38, ERK1/2, JNK, STAT1, STAT3, STAT5, AKT, FAK and IκB as well as Cox-2 (all diluted 1:1000) and horseradish peroxidase-conjugated anti-rabbit IgG (diluted 1:2000) were purchased from Cell Signaling Technology (Beverly, Mass., USA); iNOS (diluted 1:2000) from BD Biosciences (Bedford, Mass., USA). Immunocomplexes were visualized by using ECL (Amersham). To verify equal amounts of protein loading, the membranes were stripped and re-probed with horseradish peroxidase-conjugated anti-β-Actin antibody (diluted 1:10000, from Sigma-Aldrich, Saint Louis, Mo., USA). The molecular weight of proteins was estimated with pre-stained protein markers (Sigma-Aldrich, Saint Louis, Mo., USA).

Microarray Gene Expression Profiling.

Microglia isolated from four to six independently derived primary glial cultures were incubated for 48 h to silence cells. Cultures were left untreated (control cells) or were stimulated with 100 ng/ml lipopolysaccharide (LPS) or G-CM for six hours. Total RNA was extracted from the samples using RNeasy Total RNA kit (Qiagen, Germany) according to the manufacturer's recommendations, followed by DNase treatment. The amount and quality of the RNA were determined by capillary electrophoresis with the Bioanalyser 2100 and RNA 6000 LabChip kit from Agilent Technologies.

The microarray experiments were carried out in the Affymetrix reference facility of Maria Sklodowska-Curie Memorial Cancer Center-Gliwice Branch (Gliwice, Poland) using 5 μg of total RNA as a template. Biotin-labeled cRNAs were synthesized with the Affymetrix IVT labeling kit. Fragmented cRNA was hybridized first to a control microarray and then, after sample quality evaluation, to the Rat Genome 230-2.0 Gene Chips (31,042 probe sets including 28,000 rat genes).

Microarray data were pre-processed with the MAS 5.0 algorithm, as implemented in the "affy" R Bioconductor package (Irizarry et al. 2002). Only the probesets detected (call: Present) in at least three hybridizations were used. Such probesets were mapped to Ensembl 56 gene identifiers, log 2-transformed and then averaged for each gene. We used Student's t-test, with Welch's approximation to identify genes with significantly changed expression. The statistical analysis and data visualization were performed in Mathematica (Wolfram Research). For the false-discovery rate (FDR) analysis, the lists of p-values were imported into R statistical environment (http://www.R-project.org), and the q-values (Storey and Tibshirani, 2003) were calculated using the R "q-value" package.

To identify functional Gene Ontology categories associated with the observed changes in expression, the lists of genes with significantly changed expression (t-test p-value<0.001) were ranked on the difference in log 2 expression and the ranked lists were analyzed using Rank GOstat (Beissbarth and Speed, 2004) with the default options (Wilcoxon Signed Rank test, Benjamini False Discovery Rate correction for multiple testing). Rank Gostat output was parsed, edited by human and visualized using custom scripts.

HPLC Fractionation, Detection of Activating Fractions, Mass Spectrometry and Protein Identification.

Glioma-conditioned medium was dialyzed overnight against TRIS-HCl buffer. After salt and low molecular DMEM components removal, medium was lyophilized. Obtained preparation was subjected to HPLC using anion exchanger Q (Shodex IEC QA-825 PHM gel). After HPLC fractionation, 90 fractions were collected. Each fraction (diluted 1:10 in culture medium) was tested for an ability to induce morphological transformation of microglia 24 hours after treatment. Morphological alterations were evaluated and scored in a scale of 1 to 6 by two independent researchers.

Peptides from HPLC fraction were analysed by NanoSpray liquid chromatography tandem mass spectrometry (MS/MS) technology. Unprocessed data files containing MS/MS spectra were submitted to the Mascot search engine (MatrixScience Ltd., London, United Kingdom) for database searching using the Mascot daemon. The sequence of each peptide was compared against the reference rat and bovine protein sequence databases (IPI, International Protein Index), using the WU-Blast 2.0 software package (licensed from the Washington University) run with these options: -matrix blosum80-E 1-B 1-topcomboN 1-W 2-Q 12-R 12-mformat 2.

For all peptides with hits in the databases, the log ratio of the bovine e-value to the rat e-value was calculated. For identification of the proteins that can be reliably traced to the rat origin, the proteins with the following features were chosen: 1) identified by blast hits to two or more unique peptides, each of whose probability scores met or exceeded the threshold (P<0.05) for statistical significance; 2) with positive log ratios for all these sequences, indicating their rat (C6 cells) rather than bovine (culture medium) origin.

Generation of shRNA Expressing Vectors and Stably Transfected C6 Glioma Clones.

Two complementary oligonucleotides encoding spp1 shRNA and mfge8 shRNA with BamH1 and HindIII overhangs were designed to interfere with the expression of rat spp1 shRNA and mfge8 mRNA. The two oligonucleotides used were:

```
Spp1: forward
                                        (SEQ ID NO: 21)
5'-GATCCAGCTAGTCCTAGACCCTAATTCAAGAGATTAGGGTCTAGGAC
TAGCTTGTTTTTTGGAAA-3'
and reverse
                                        (SEQ ID NO: 22)
5'-AGCTTTTCCAAAAAACAAGCTAGTCCTAGACCCTAATCTCTTGAATT
AGGGTCTAGGACTAGCTG-3'.

Mfge8: forward
                                        (SEQ ID NO: 25)
5'-GATCCGGATGAAAGCGGAACCGGATTCAAGAGATCCGGTTCCGCTTT
CATCCTGTTTTTTGGAAA-3'
and reverse
                                        (SEQ ID NO: 26)
5'-AGCTTTTCCAAAAAACAGGATGAAAGCGGAACCGGATCTCTTGAATC
CGGTTCCGCTTTCATCCG-3'
```

Two complementary oligonucleotides encoding GM-CSF shRNA with BamH1 and HindIII overhangs were designed to interfere with the expression of mouse GM-CSF mRNA. The two oligonucleotides used were:

```
Sense:
                                        (SEQ ID NO: 23)
5'-GATCCCGGAAACGGACTGTGAAACATTCAAGAGATGTTTCACAGTCC
GTTTCCGGTTTTTGGAAA-3';
and Antisense:
                                        (SEQ ID NO: 24)
5'-AGCTTTTCCAAAAAA CCGGAAACGGACTGTGAAACA TCTCTTGAA
TGTTTCACAGTCCGTTTCCGG-3'..
```

Forward and reverse oligonucleotides were incubated in 0.1 M NaCl for 3 min at 94° C., followed by slow cooling to 37° C. for 1 h. The annealed DNA was ligated with pSilencer 2.0-U6 (Ambion, Germany) at BamHI and HindIII sites. After transformation into *E. coli*, plasmids were amplified, isolated and the sequences were verified by sequencing. The pSilencer-spp1, pSilencer-mfge8 pSilencer-GM-CSF and pSilencer 2.0-U6 Negative Control (Ambion) vectors were purified with Qiagen Plasmid Maxi Kit and 1.6 μg of each DNA was transfected into cells using 2 µl Lipofectamine-2000 (Invitrogen, UK). One day after transfection, hygromycin B (200 µg/ml) was added. Resistant clones were picked after 2 weeks and analysed for expression of appropriate mRNA by qRT-PCR.

RNA Isolation and Quantification of Gene Expression.

RNA was isolated with RNeasy Mini Kit (Qiagen). First-strand cDNA was synthesized from 2 µg of total RNA (DNase-treated) in a 20 µl reverse transcriptase reaction mixture. 18s rRNA was used as an internal reference gene. The expression of Osteopontin, and lactadherin in C6 rat glioma cells and primary astrocytes was evaluated using qPCR. The expression of GM-CSF in GL261 glioma cells and primary astrocytes was evaluated using qPCR. For example, for evaluating the expression of GM-CSF the following primers were used:

```
                            (SEQ ID NO: 27)
forward:    5'TGCCTGTCACGTTGAATGAAGAGGT'3, (SEQ ID NO: 28)
reversed:   5'GCCCCGTAGACCCTGCTCGA'3;
```

For 18s RNA the following primers were used:

```
                            (SEQ ID NO: 29)
forward:    5'CGGACATCTAAGGGCATCAACA'3;

(SEQ ID NO: 30)
reversed:   5'AACGAACGAGACTCTGGCATG'3.
```

Reaction volume (20 µl) consisted of cDNA equivalent to 50 ng RNA, 1×SYBR Green PCR master mix (Applied Biosystems) and 0.9 µM of each primer. The thermal cycling conditions were as follows: 50° C. for 2 min, 95° C. for 10 min, followed by 40 cycles of 15 s at 95° C. for denaturation and 1 min. at 60° C. for annealing and extension. Relative quantification of gene expression was determined using the comparative CT method.

Plasmid Construction, Transfection and Recombinant Protein Production.

The coding sequence of spp1a and spp1c was amplified on cDNA template from rat glioma C6 cells with primers: 5'-ATCAAAGCTTCATATGAGACTGGCAGTG-GTTTGC-3' (SEQ ID NO: 31) and 5'-ATCGCGGCCGCT-TAATTGACCTCAGAAGATGAACTC-3' (SEQ ID NO: 32) using Taq DNA polymerase (Applied Biosystems). The coding sequence of mfge8 was amplified on cDNA from rat glioma C6 with primers:

```
                            (SEQ ID NO: 33)
5'-ATCAAAGCTTCATATGCAGTTCTCCCGTGTGCTGGC-3'
and (SEQ ID NO: 34)
5'-ATCGCGGCCGCTAACAGCCCAGCAGCTCCAGGC-3'.
```

Amplified sequences of spp1a, spp1c and mfge8 were subcloned into HindIII, NotI site of the pEGFP-N1 plasmid. The resulting plasmids (called pSpp1a, pSpp1c and pMFG8) were verified by sequencing.

Recombinant osteopontin and lactadherin proteins were produced in murine fibroblasts by overexpression of pSpp1a, pSpp1c and pMFG8 plasmids. Fibroblasts NIH 3T3 (from ATTC) were plated into 24-well plates at a density of 1.7×10$^5$/well and after 24 h cells were transfected using Amaxa program U-30 and Kit R for NIH/3T3 cells (Amaxa, Germany) with pSpp1a, pSpp1c and pMfge8 plasmids using 1.6 µg of DNA, then incubated for 24 h to recover. Protein production was determined with ELISA (R&D, Germany).

Real Time PCR.

Total RNA (2 µg) isolated from microglia cultures untreated or treated for 6 h with LPS or G-CM was used as a template to generate cDNA. As endogenous control 18S (Hs99999901_s1) rRNA was applied. Gene expression quantification was performed using the Applied Biosystem TaqMan® The real time amplifications were performed in duplicates in a 20 µl reaction volume containing 2×SYBR PCR MasterMix and a set of primers designed using PRIMER EXPRESS software for the following genes: iNOS, COX-2, Il1beta, TNF alpha, MMP-2, MMP-9, MMP-14, Arg1, Id1 and c-Myc. The amount of target mRNA was first normalized to the 18S RNA expression level and then to a control. Data were analysed by the Relative Quantification ($^{\Delta\Delta}$Ct) method using 7500 System SDS software (Applied Biosystems). The expression of each product was normalized to 18S rRNA and is shown as the ratio of the target gene to 18S gene expression, calculated by $2^{-\Delta\Delta Ct}$.

Intracranial Glioma Implantation and Quantification of Tumor Size.

This study was conducted under the protocol 857/2008, which was approved by the Local Ethics Committee for Animal Experimentation.

Adult C57BL/6 mice (12-16 wk) were anesthetized with an i.p. injection of ketamine (75 mg/kg) and medetomidine (1 mg/kg). EGFP-GL261 glioma cells, shGM-CSF glioma cells or shNeg glioma cells (8×10$^4$ cells in 1 µl of DMEM) were inoculated in a right striatum using 1-µl syringe with a 26-gauge needle in a stereotactic apparatus according to the coordinates (+1.5 mm AP, −1.5 mL). Mice were resuscitated using i.p. administration of atipamazole and anesthetized with Tolfedine 4% (4 mg/kg s.c.). At day 15th after glioma implantation, the animals were anesthetized, sacrificed and perfused with PBS or PBS and 4% paraformaldehyde in PBS. The brains were removed and minced or post-fixed for 24 h in the same fixative solution and placed in 30% sucrose in PBS at 4° C. Next, brains were frozen with dry $CO_2$ and serial 20-µm-thick coronal sections were collected using a cryostat. Images were acquired using a Leica DM4000B microscope.

Tumor areas in coronal sections were measured using Image Pro-Plus software in an every second brain slice and tumor volumes were calculated according to the Cavalieri principle.

Osteopetrotic Mice and Genotyping for Detection of the Csf1$^{op}$ Mutation.

Breeding pairs of B6C3Fe a/a-Csf1$^{op}$/J mice were obtained from the Jackson Laboratory (Bar Harbor, Me.) and were maintained, and bred in a barrier facility under controlled conditions of light (12L:12D) and temperature. Homozygous mutants were distinguished from wild-type and heterozygous mice at 10-11 days of age by the absence of incisors and with a Real-Time PCR-based genotyping method. The op/op mutant mice were weaned at postnatal day (P)-21 and fed with powdered rodent diet. The Csf1$^{op}$ mutation was detected by PCR analysis of genomic DNA using the TaqMan Allelic Discrimination Method and ABI PRISM 7700 (Applied Biosystem). The DNA samples were prepared from the tail tip between 4 and 10 days of age.

Induction of Focal Demyelination in the Spinal Cord and Quantification of Microglia Density.

Osteopetrotic and wild type mice aged 2 months were used. Animals were anesthetized through continuous inhalation of isoflurane and oxygen. The position of T4 was identified and the epaxial musculature was cleared. The space between T4 and 5 was exposed and cleared with the use of microscope. The central vein was identified, and the dura was perforated with a dental needle. The demyelination lesions were induced by stereotaxic injection of 1 µl of 1% Lα-lysophosphatidylcholine (Sigma) into the dorsal funiculus over a period of 2 min using Hamilton needle with a fine glass tip attached to three-way manipulator. Injection of the toxin resulted in demyelination of axons which was followed by microglia recruitment to the lesion site. Ten days after the lesion induction mice were anesthetized with isoflurane and aortic-perfused with 4% paraformaldehyde in phosphate-buffered saline (pH 7.4). The part of the spinal cord containing the lesion was dissected, post-fixed in 4% PFA at 4° C. overnight, cryoprotected in 30% sucrose over 48 hr at 4° C., mounted in OCT embedding compound, frozen on dry ice and cut on a cryostat at 12 µm. Cross-sections were mounted on poly-L-lysine-coated glass slides (Thermo Scientific). Iba1 staining and visualization with DAB was performed. Images of the spinal cord lesions were taken with Leica DM 4000B microscope with a digital camera. Two representative pictures of lesion from each animal were taken and the total number of Iba-1-labelled microglia cells in the lesion was counted with the use of Image J software (NIH).

Immunohistochemistry.

Staining with anti-Iba1 and anti-vWF antibodies was performed to detect microglia/macrophages and blood vessels, respectively. Sections were incubated with 0.5% $H_2O_2$ in PBS for 30 min at RT, permeabilized and blocked with 10% donkey serum with the addition of 0.3% Triton X-100 in PBS, and then incubated with the primary antibodies: anti-Iba-1 (rabbit, polyclonal, WAKO, 1:1000) or anti-vWF (rabbit, polyclonal, Abcam, 1:1000) for 24 h at 4° C. and with the secondary goat anti-rabbit biotinylated IgG for 2 hr at RT. The primary and secondary antibodies were diluted in PBS containing 0.1% Triton X-100 and 3% donkey serum. The sections were exposed to extravidin-peroxidase complex (1:200) for 1 h at RT and peroxidase activity was visualized with 0.02% 3.3'-diaminobenzidine (DAB) and 0.01% $H_2O_2$ in Tris buffer (pH 7.6). Sections were dehydrated and mounted with Histofluid (Sigma, Germany).

Isolation of CD11b-Positive Cells and Flow Cytometry.

Tumor hemispheres were isolated, brain tissues were cut into small pieces and minced to receive single-cell suspension. Cells were stained with CD11b-PE and C45-PerCP antibody to determine percentages of microglia and macrophages (BD Pharmingen). Stained cells were assessed by flow cytometry (FACSCalibur). Data were acquired and analyzed using CellQuest software.

Tumor Invasion in Organotypical Brain Slice Cultures.

The organotypical brain slice cultures were obtained from 16-day-old male C57/BL6 mice (animal breeding facility, Schonwalde, Germany). The brain slices cut into 250 µm sections were transferred to a Transwell insert in a 6-well plate (Becton Dickinson, Lincoln Park, N.J., USA) and were incubated in 1 ml of DMEM (Gibco, Gaithersburg, Md., USA) supplemented with 10% FCS (Atlanta Biological, USA), 0.2 mM glutamine and antibiotics. After overnight equilibration, medium was exchanged for the cultivation medium containing 25% FCS, 50 mM sodium bicarbonate, 2% glutamine, 25% Hanks balanced salt solution, 1 µg/ml insulin (all from Gibco, Gaithersburg, Md., USA), 2.46 mg/ml glucose (Braun Melsungen AG, Germany), 0.8 µg/ml vitamin C (Sigma-Aldrich, Germany), 5 mM Tris and antibiotics. Slices were injected with 10,000 GFP-GL261 glioblastoma cells (in 0.5 µl) using a syringe mounted to a micromanipulator. For preparation of microglia depleted slices, organotypical brain slices were treated for 24 h with liposomes filled with clodronate.

Quantitative Analysis of CSF-1(M-CSF) and CSF-2 (GM-CSF) Expression in Human Glioma Biopsies and the Reference Normal Brain.

The glioma biopsies were obtained from the Brain Tumor Tissue Bank (London Health Sciences Centre, London, Ontario, CA) and The Children's Memorial Health Institute, Warsaw, Poland. The study includes 24 GBM and 20 pilocytic astrocytomas (WHO grade 1). The reference brain RNA is a mixture of RNA from 5 normal brains (Ambion). Total RNA was prepared as described (Tyburczy et al. 2010) by Tri-Reagent (Sigma-Aldrich, Munich, Germany) extraction from snap-frozen tissues. RNA was cleaned up using RNeasy Mini Kit (Qiagen, Hilden, Germany). The quality and quantity of total RNA were verified using the Agilent bioanalyzer (Agilent Technologies, Santa Clara, Calif.). Real time PCR amplifications were performed in triplicate on cDNA equivalent to 25 ng RNA with the primer sets: for CSF-1—Hs 00174164_m1; fro CSF-2—Hs 00929373_1; GAPDH—Hs 02753991_g1 (Applied Biosystem) GAPDH was used as an internal standard reference. The relative quantification of gene expression was determined with ABI PRISM 7700 Sequence Detection System using the comparative CT method. The values were compared to the expression of a given gene in the reference normal brain.

Kaplan-Meier Survival Plot.

All human data was publicly available on the Rembrandt website (https://caintegrator.nci.nih.gov/rembrandt/). Both the microarray gene expression data and the clinical data were obtained from the NCI Repository for Molecular Brain Neoplasia Data (REMBRANDT) database using data available on Oct. 1, 2011. At the time of access, 343 glioma patient samples with both gene expression data and corresponding survival times were available on the Rembrandt database. The graphs were created using Rembrandt microarray data for the probes from the Affymetrix U133 Plus 2.0 GeneChip and associated survival data. CSF1 and CSF2 up- or down-regulation was defined as a 2-fold (or greater) difference from the mean expression level within a given data set.

Statistical Analysis.

The results were expressed as means±standard deviation (s.d). Statistical significance was determined by U-Mann-Whitney test and Student's t-test using Statistica software (ver. 7.1 StatSoft. Inc, OK, USA).

Example 2

Characterization of Microglia Behaviour and Intracellular Signalling Induced by Glioma-Derived Factors Primary microglia cultures isolated from postnatal rat brains were used for all experiments. Purity of microglia cultures was always >95% as determined by FITC-lectin B4 staining. Cultures were left for 48 hours before each experiment to silence microglia. Microglia cultures were exposed to glioma- or astrocyte-conditioned medium, in the absence of other exogenous stimuli or stimulated with 100 ng/mL lipopolysacharide (LPS) which reflects classical inflammatory activation. Only medium from glioma cells (GCM), but not astrocytic cultures, was able to induce morphological transformation of microglia cells into amoeboid cells (FIG. 1A), as evidenced by light contrast microscopy (upper panel) and staining of F-actin with FITC-phalloidin (lower panel). Photographs of cultures were taken 24 hours after addition of the stimulus. Similar morphological transformation was observed after treatment with a classical inflammation inducer—lipopolysacharide (LPS, 100 ng/mL). While LPS induced growth arrest and reduced the levels of cyclin D1 and phospho-Rb; GCM stimulated microglia cells proliferated normally and the levels of cyclin D1 and phospho-Rb were unaffected (FIG. 1B).

However, the presence of GCM strongly increased motility of microglia cells into cell-free areas in a scratch assay (FIG. 1C). Phagocytosis was evaluated by adding red fluorescent beads for 6 h to control or GCM-treated cultures and quantifying the percentage of cells that phagocytosed two or more beads by fluorescence microscopy. The number of microglia cells phagocyting multiple beads increased by 60±9% (mean±s.d.) after exposure to GCM as compared to control cells (FIG. 1D). Data are presented as mean±s.d. from 3 experiments on independently derived microglia cultures; ***p<0.005.

Figure 2B:
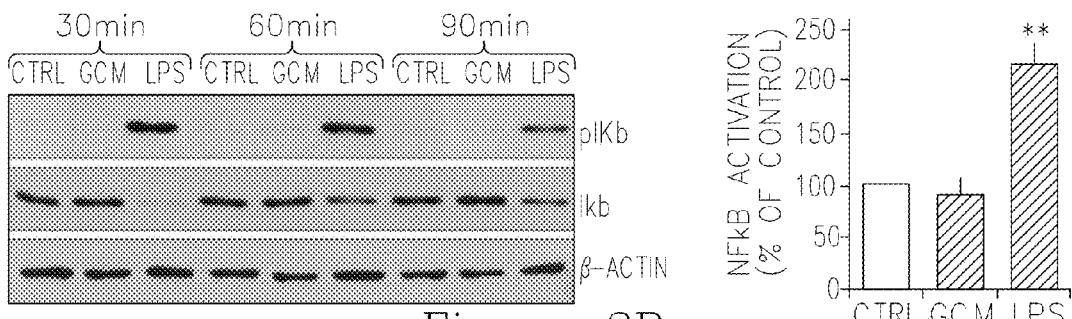
Figure 2C:
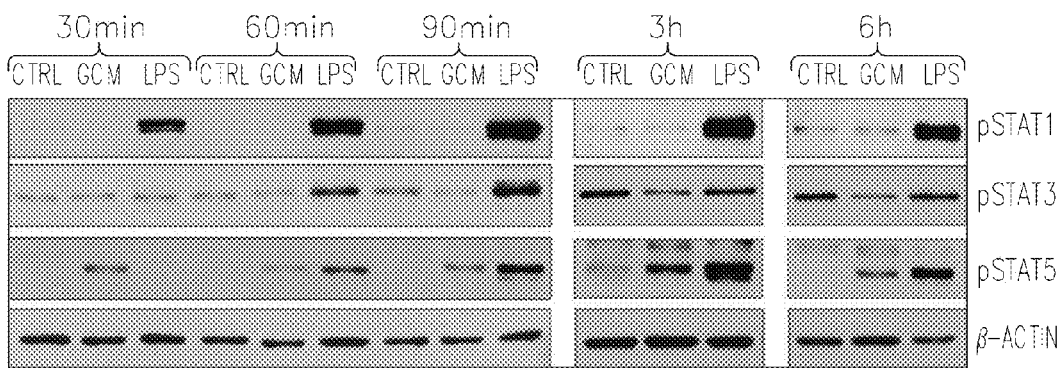
Figure 2D:
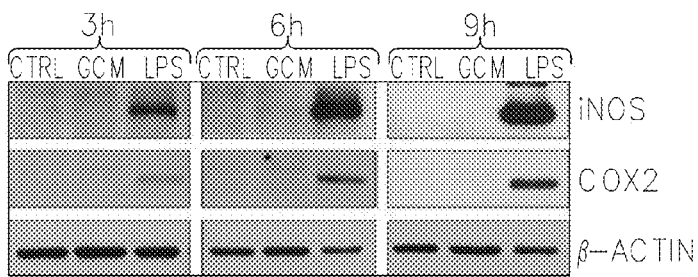

Inflammatory stimuli (e.g. LPS) activates common signalling pathways crucial for initiation of inflammation and involves MAP kinases and transcription factors such as NFκB, STAT1, 3 and 5 in microglia cells. The levels of phosphorylated MAPK, p-IκB and phospho-STATs increased 30 min after LPS treatment and remained elevated for 6 h (FIG. 2A). Notably, there were some differences in GCM-treated microglia cells: JNK was not activated and activation of p38 MAPK was weaker and more transient than after LPS (FIG. 2A). Phosphorylation of IκB and its degradation were not detected in GCM-treated microglia resulting in lack of NFκB activation (FIG. 2B left panel). This was further confirmed by measurements of NFκB DNA binding activity by ELISA (FIG. 2B—right panel). Increased phosphorylation of STAT1 and STAT3 occurred only in LPS-treated microglia cells, while elevation of phosphorylated STAT5 occurred under both conditions (FIG. 2C). Defects in activating signalling pathways critical for inflammation resulted in lack of expression inflammation mediators such as an inducible nitric oxide synthase (iNOS) and cyclooxygenese 2 (FIG. 2D). All data are consistent with induction of the non-inflammatory, M2-like activation of microglia cells by GCM.

Example 3

Analysis of Transcriptional Changes Induced by GCM

Figure 3A:
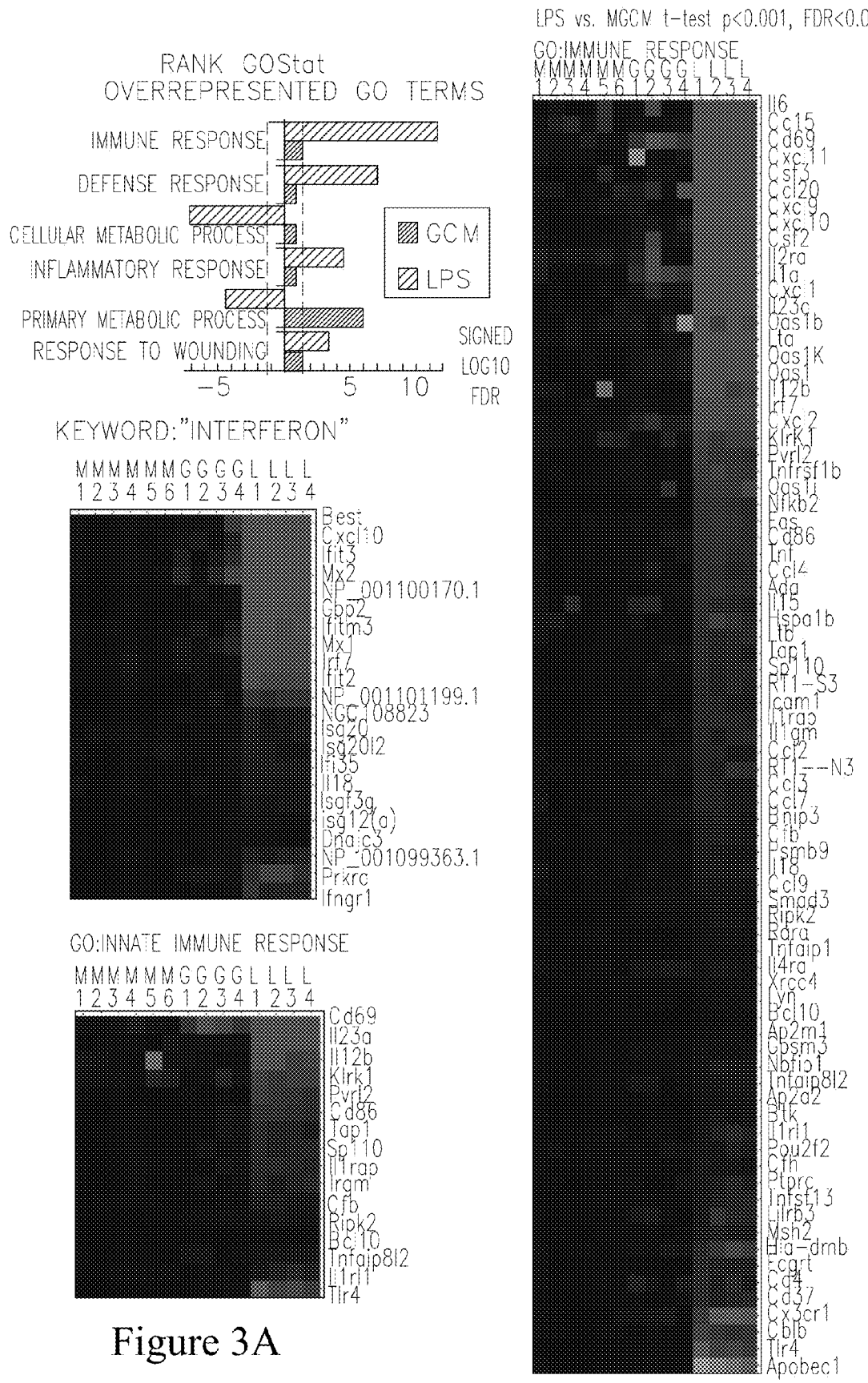
FIGS. 3A-3B show a comparison of transcriptional changes induced in microglia cells as a result of GCM and LPS stimulation.
Figure 3B:
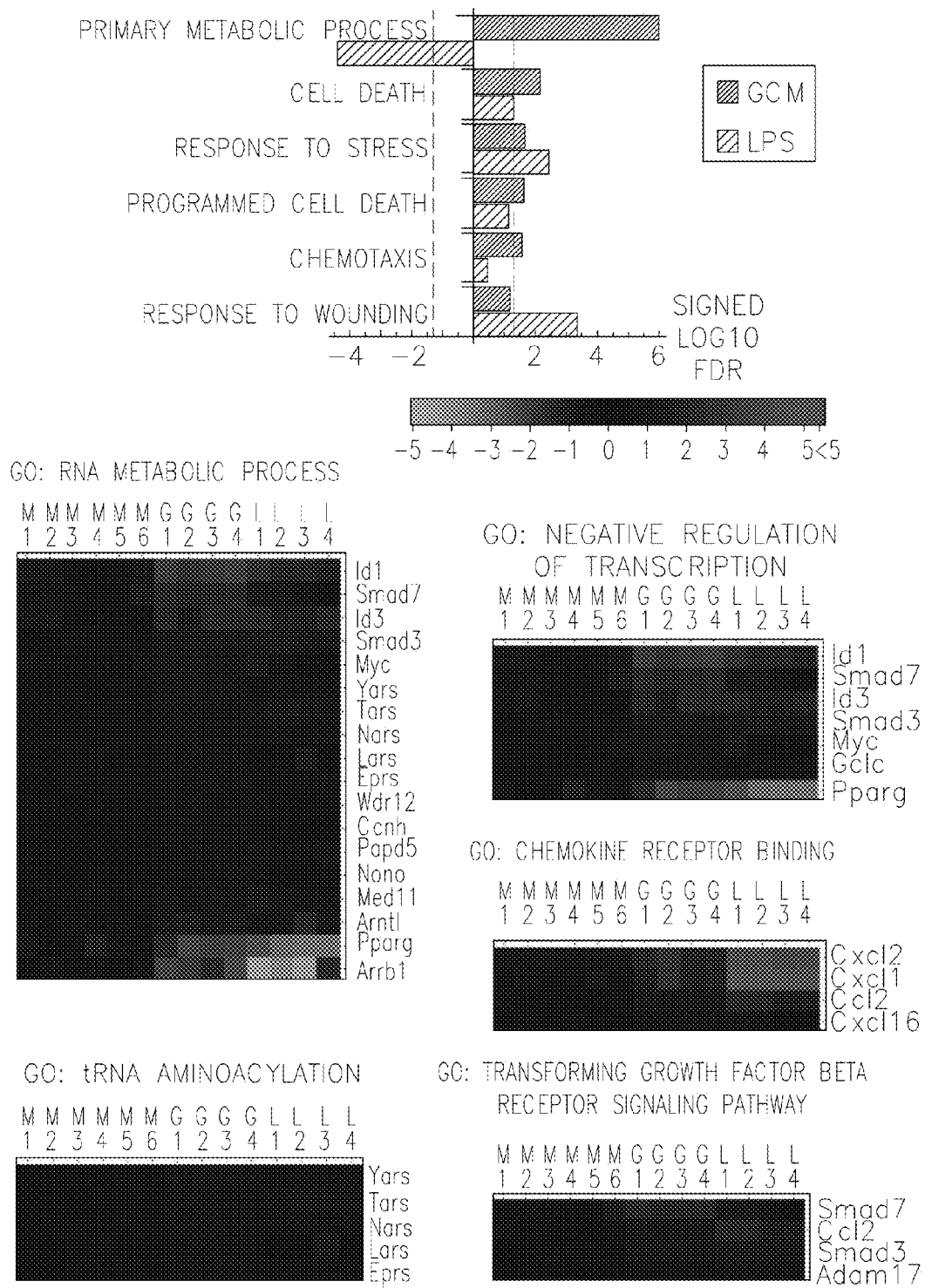

As shown in FIG. 3, GCM induces distinct changes in the expression profile of microglia cells.

To obtain a comprehensive view of genomic responses in GCM stimulated microglia cultures, global gene expression profiling and Gene Ontology analysis was performed in differentially stimulated microglia cells. Global gene expression was probed with Affymetrix oligonucleotide microarrays 6 h after treatments with either GCM or LPS. Separate statistical analysis (t-test) were carried out for the comparison between the GCM (n=4) and the control (MGCM, n=6), and between the LPS (n=4) and the same control. A uniform alpha level of t-test p<0.001 was chosen to identify genes affected by either treatment. This choice corresponds to FDR<0.002 for the more robust changes induced by LPS, and FDR<0.04 for the relatively smaller changes induced by GCM. Changes in expression of genes regulated by GCM (G) and/or LPS (L), as compared to control MGCM (M), and plotted against each other on a Log 2 scale. Each gene is represented by a dot, with its X, Y coordinates indicating the change in its expressions caused by LPS and GCM, respectively. Large grey dots mark genes significantly regulated by LPS (L vs. M t-test p<0.001). Small blue dots mark genes significantly regulated by GCM (G vs. M t-test p<0.001). The dots representing genes significantly regulated by both treatments, but in the opposite directions (and additionally SMAD 3 and 7) are annotated with their gene symbols, and their expression profiles over individual microglia cultures (numbered) are shown.

At the chosen alpha level, 174 genes changed expression following GCM treatment, 1794 genes—following LPS treatment (grey dots), and 63—following both treatments. Of the last group, 9 genes (8 known genes) were oppositely regulated in the two treatments in.

Analysis of the functional content of the 1794 genes significantly regulated by LPS, with the program Rank GOStat revealed GO terms: immune/defense/inflammatory response as the categories significantly associated with gene up-regulation following LPS treatment (upper left panel). Notably, none of those categories were significantly affected by GCM treatment. This lack of up-regulation of immune response and inflammation genes was confirmed by heatmap visualization. Moreover, the interferon-related genes most strongly up-regulated by LPS (Best5, Cxcl10, Ifit3, Mx2) were preferably down-regulated by the GCM treatment.

Analysis of the functional content of 174 genes significantly regulated by GCM with Rank GOStat identified the GO category "primary metabolic process" as the highest ranking category associated with gene up-regulation by GCM. Interestingly these genes were down-regulated after LPS.

A few genes such as c-Myc, SMAD7, klhl6, hla-dmb and CX3CR1 were strongly induced in GCM-treated microglia but down-regulated in LPS-treated cells. The c-Myc encodes a multifunctional transcription factor that directs the expression of genes required for transcription, ribosome biogenesis, cell-cycle progression, differentiation, apoptosis, and cell motility. Interestingly, GCM up-regulated genes implicated in regulation of transcription and translation, including Gar1, Gtpbp4, Nol8, Ddx5, Polr1e, Polr1b, Eif4ebp1, Eif3s9, Nob1, Tsen2, Ndel1, Hnrnpr, Nip7, Nup93, and several aminoacid-tRNA synthetases. Additional genes induced by GCM include CD69, a member of the C-type lectin R family, the co-stimulatory molecule CD86 implicated in dendritic cell maturation, and chemokines implicated in macrophage recruitment into tissue such as: RANTES (ccl5), MCP-1 (ccl2), and CXCL (cxcl1, 2, 7).

Figure 4:
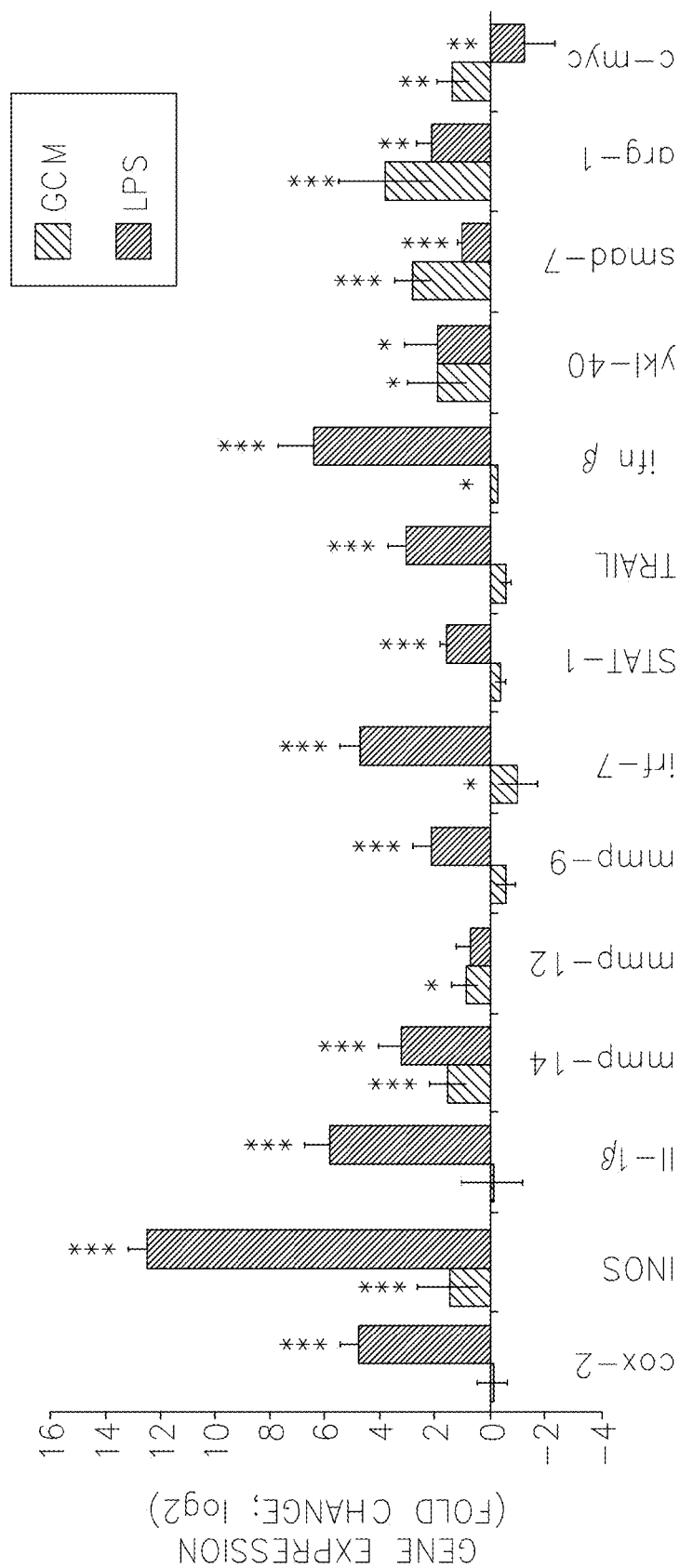
FIG. 4 shows Real Time PCR of selected genes in microglia cultures stimulated with either GCM or LPS.

The expression of 14 genes was verified by quantitative PCR on 4 independent microglia cultures. Q-PCR data confirmed absence or weak expression of inflammation and interferon signalling related genes (COX-2, IL1β, iNOS, MMP-9, Irf7, STAT1, TRAIL, IFNβ) in GCM-stimulated microglia, and up-regulation of c-Myc, SMAD7, Arg-1, MMP-14 expression (FIG. 4). We conclude that, the changes induced by GCM functional different and partially opposite (for the interferon-related genes) from the changes accompanying the "classical" microglia/macrophage activation by LPS.

Example 4

Figures 5A, 5B:
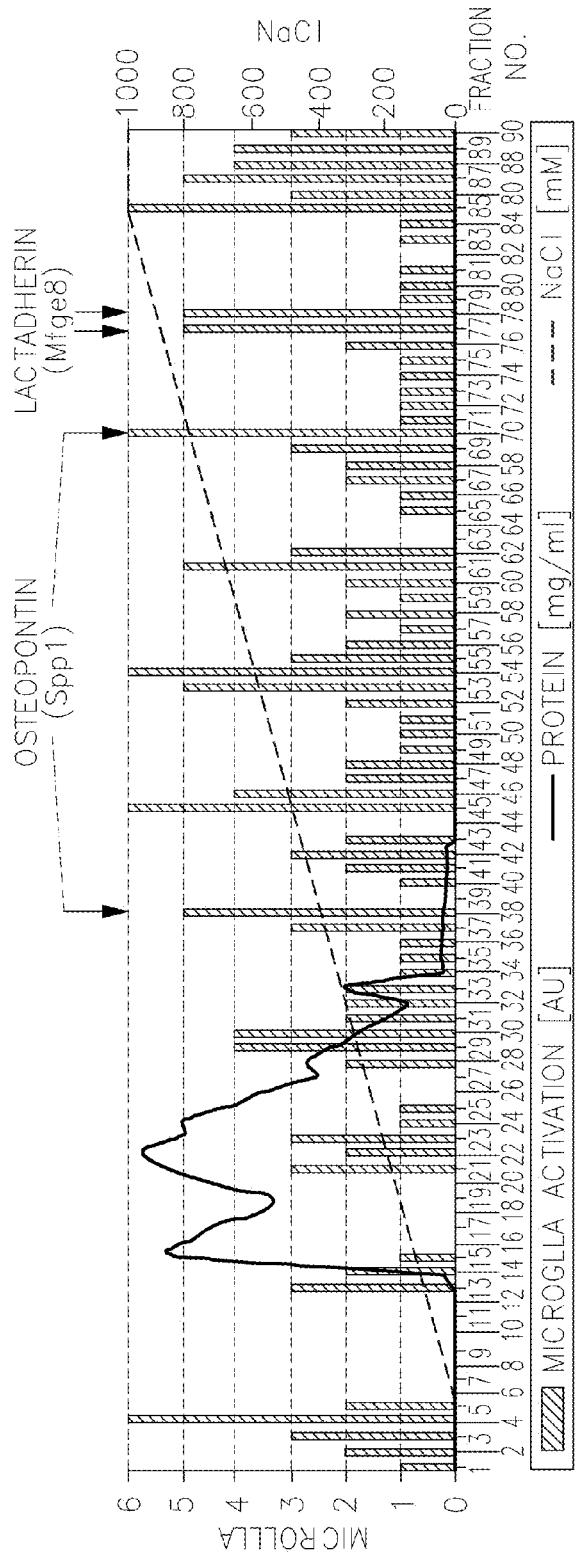
FIGS. 5A-5D show the glioma derived proteins, osteopontin and lactadherin, in microglia-activating fractions; and rat C6 glioma cells over-expressing osteopontin and lactadherin: (A) Fractionation of GCM culture medium and scoring of ability to transform microglia cells into amoeboid cells; (B) MS/MS analysis of the activating fractions identifying the peptide sequences set forth in SEQ ID 44-SEQ ID 53 of osteopontin and lactadherin; (C) Phagocytosis assay of activating fractions; (D) Real time PCR of osteopontin isoforms (spp1a and spp1c) and lactadherin in C6 glioma cells as compared to non-transformed cortical astrocytes; and ELISA assay of osteopontin secretion by C6 glioma cells.
Figure 5C:
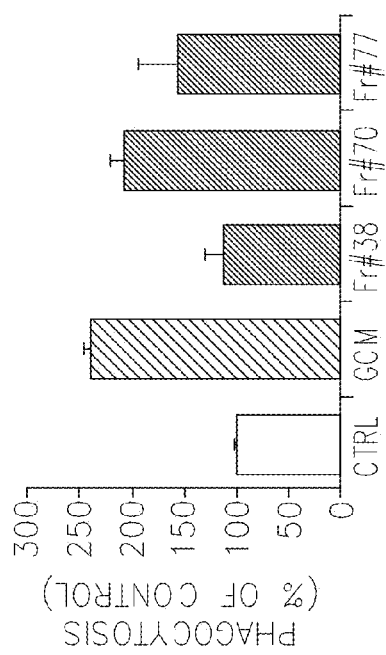
Figure 5D:
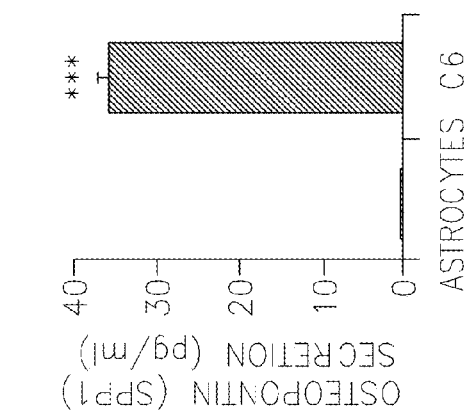
Figure 5D:
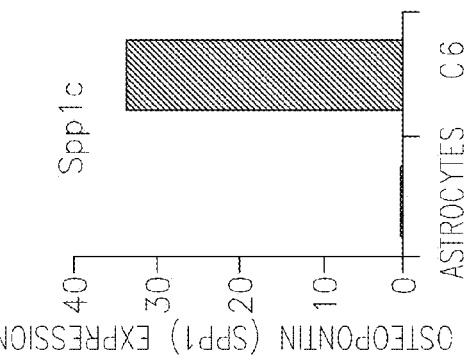
Figure 5D:
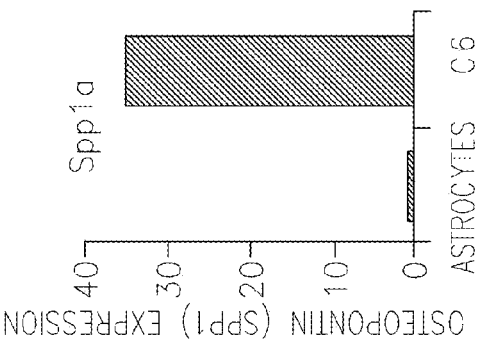
Figure 5D:
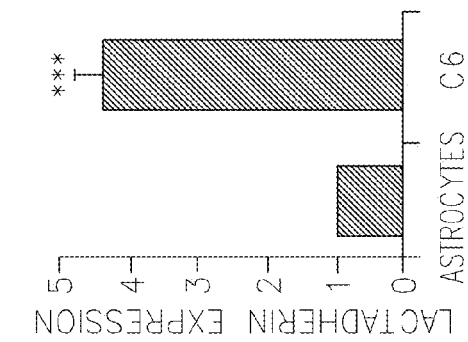

Identification of Osteopontin and Lactadherin as Microglia-Activating Activities of Tumour-Conditioned Medium A proteomic approach was employed to identify components of glioma-conditioned medium that activate microglia cells. GCM was fractionated by HPLC using anion exchanger Q (Shodex IEC QA-825 PHM gel) and 90 fractions containing GCM-derived proteins were collected. Each fraction (diluted 1:10 in culture medium) was evaluated for the ability to activate microglia cultures. Microglia transformation into amoeboid cells was scored at a range of 1 to 6 by two researchers 24 h after treatment. Sixteen fractions with stimulatory activity (scored 4-6) vs. control (scored 3) and several fractions inhibiting microglia (scored 1-2) were obtained (FIG. 5A). Protein preparations, which stimulated microglia cells, were subjected to MS/MS analysis using ESI-FTICR. Individual fractions were tested for their ability to stimulate microglia to phagocytosis (FIG. 5C). Unprocessed data files containing MS/MS spectra were submitted to the Mascot search engine for database searching. The protein sequence was identified by mass spectrometry analysis of two or more unique peptides, each with a probability score of at least ($p<0.05$) to ensure a low false discovery rate. This process resulted in the identification of osteopontin and lactadherin (FIG. 5B). Osteopontin production by glioma cells and astrocytes was confirmed by ELISA (FIG. 5D—right panel) and the levels of osteopontin (spp1) and lactadherin mRNA were determined by quantitative PCR in the rat C6 glioma cells and presented as fold changes vs. rat cortical astrocytes. It was found that glioma cells highly overexpress two forms of osteopontin: spp1a mRNA was higher 35-fold and spp1c mRNA 600-fold in comparison to non-transformed astrocytes (FIG. 5D—left panels). Data are mean±s.d. of at least 3 independent experiments.

Example 5

Figures 6A, 6B:
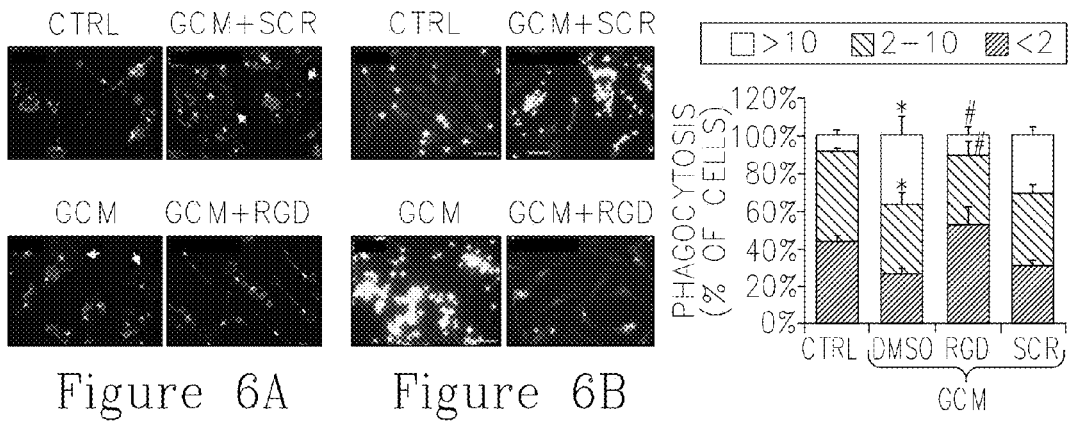
FIGS. 6A-6F show interference with integrin binding by treating with a RGD-containing peptide and blocking of glioma-induced actin cytoskeleton changes, phagocytosis and cell motility. (A) Immunofluorescence microscopy of F-actin in microglia cells pre-incubated with GCM culture media supplemented with the RGD inhibitor; (B) Phagocytosis assay of microglia cells pre-incubated with GCM culture media supplemented with the RGD inhibitor; (C) Scratch assay of microglia cells pre-incubated with GCM culture media supplemented with the RGD inhibitor; (D) Phagocytosis assay of cells treated with siRNA against αv, β3 (or both) integrin subunits; (E) Immunoblotting of phosphorylated FAK in microglia cells pre-incubated with GCM culture media supplemented with the RGD inhibitor; (F) Model of the proposed link between integrin ligands, intracellular pathways and cell transformation into fast moving, amoeboid macrophages.
Figures 6C, 6D:
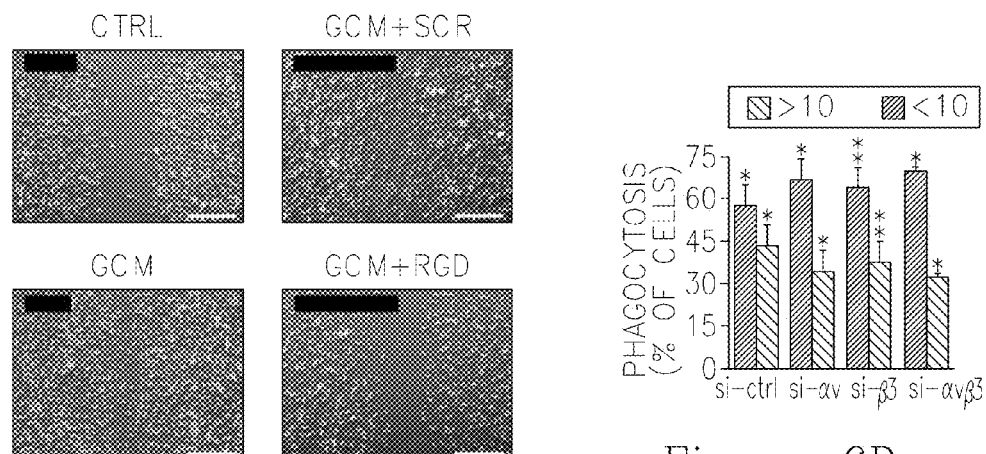
Figure 6E:
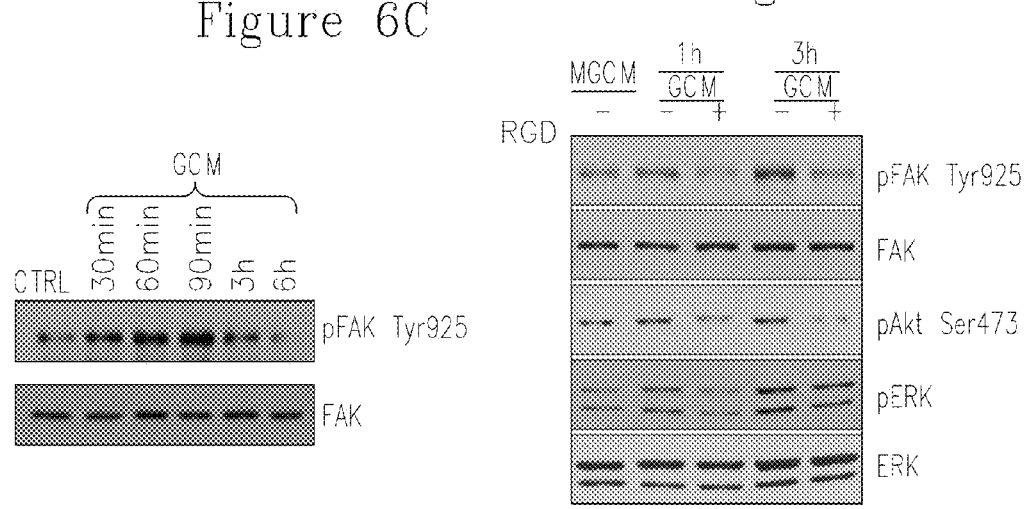
Figure 6F:
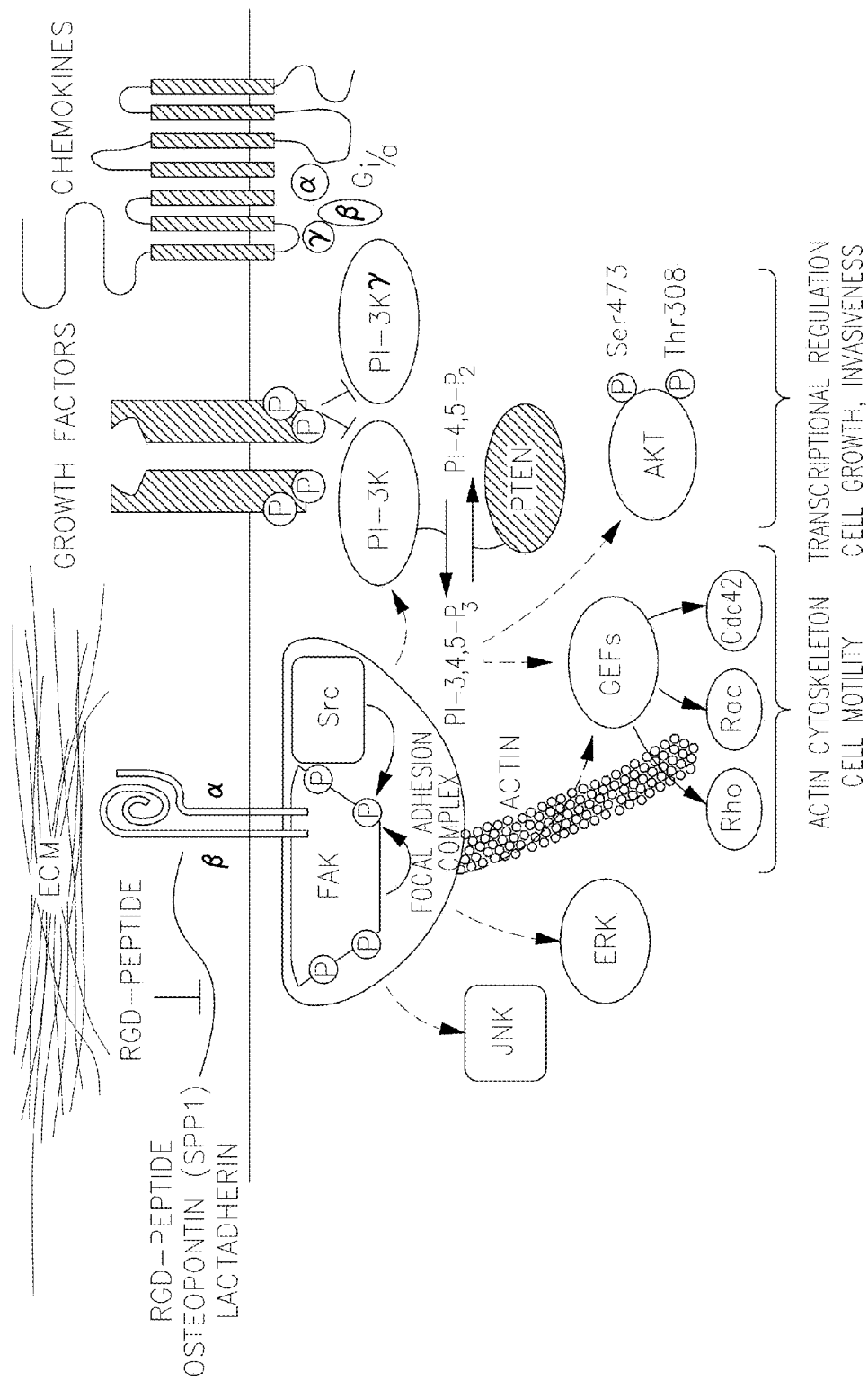

Interference with Osteopontin and Lactadherin Binding to Integrins Abolished Morphological Transformation, Migration and Phagocytosis Induced by Glioma-Derived Factors Using the rat lactadherin amino acid sequence, a 7-aa RGD-containing peptide (RGD) was designed as a competitive inhibitor (set forth in SEQ ID NO: 18). A scrambled sequence peptide was used as a control (SCR). Pre-incubation with the chemically synthesized 500 μM RGD peptide, but not with the SCR peptide, prevented transformation of microglia into amoeboid cells following GCM induction (amoeboid cells indicated with arrows) (FIG. 6A). The RGD peptide completely blocked GCM-induced phagocytosis (FIG. 6B) and microglia migration in a scratch assay (FIG. 6C). GCM-induced increase of phagocytosis was considerably reduced in microglia cells after silencing of integrin subunits αv or β3 or both with specific siRNAs (FIG. 6D). Consistently with a putative mode of action via integrins, GCM treatment increased phosphorylation of focal adhesion kinase (FAK), a common mediator of integrin signalling (FIG. 6E). GCM increased the levels of phosphorylated FAK and other kinases Akt and ERK in microglia cells and pre-treatment with a RGD peptide abolished activation of all studied kinases (FIG. 6E). A non-binding model of the proposed link between integrin ligands, intracellular pathways and cell transformation into fast moving, amoeboid macrophages is proposed in FIG. 6F.

Example 6

Figure 7A:
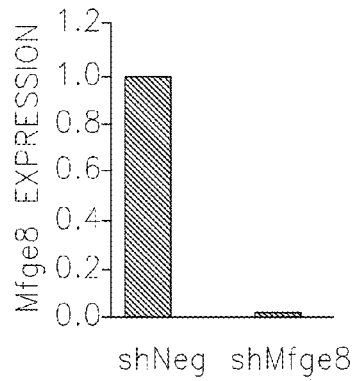
FIG. 7A-7E show distinct effects of lactadherin and osteopontin silencing on GCM induced gene expression and microglia-dependent glioma invasiveness: (A) Quantitative PCR of lactadherin (mfge8) in C6 glioma cells stably expressing control (shNeg), or lactadherin shRNA; (B) Quantitative PCR of selected genes in lactadherin depleted GCM-treated glioma cells; (C) Quantitative PCR of osteopontin (spp1) in C6 glioma cells stably expressing control (shNeg) or osteopontin shRNA; (D) Quantitative PCR of selected genes in osteopontin depleted GCM-treated glioma cells; (E) Matrigel matrix invasion assay of glioma cells in the presence or absence of osteopontin and lactadherin depleted microglia cells.
Figure 7B:
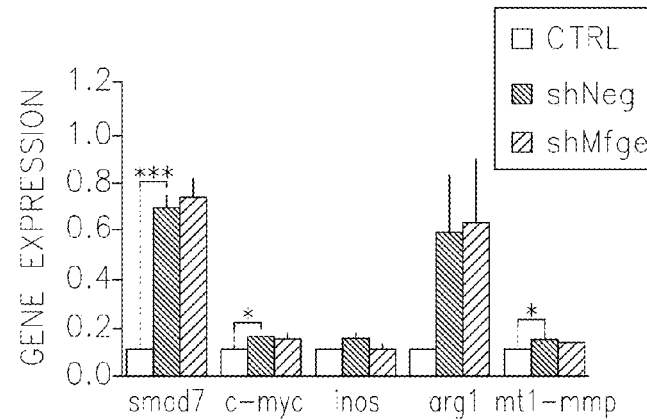
Figure 7C:
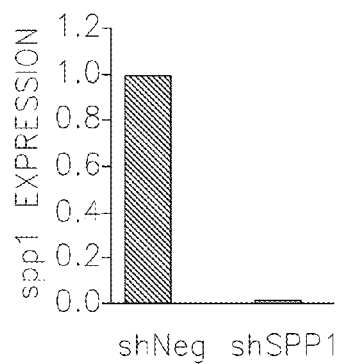
Figure 7D:
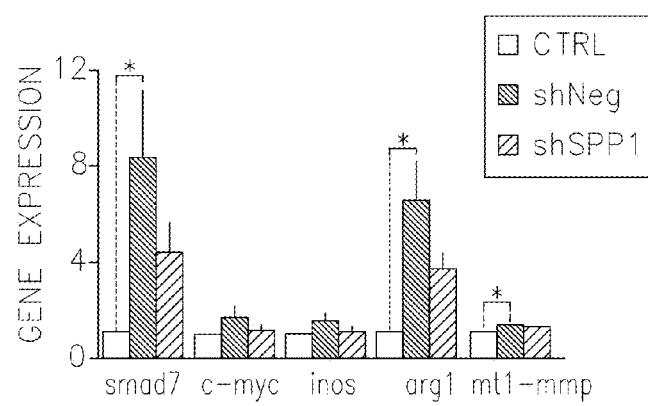
Figure 7E:
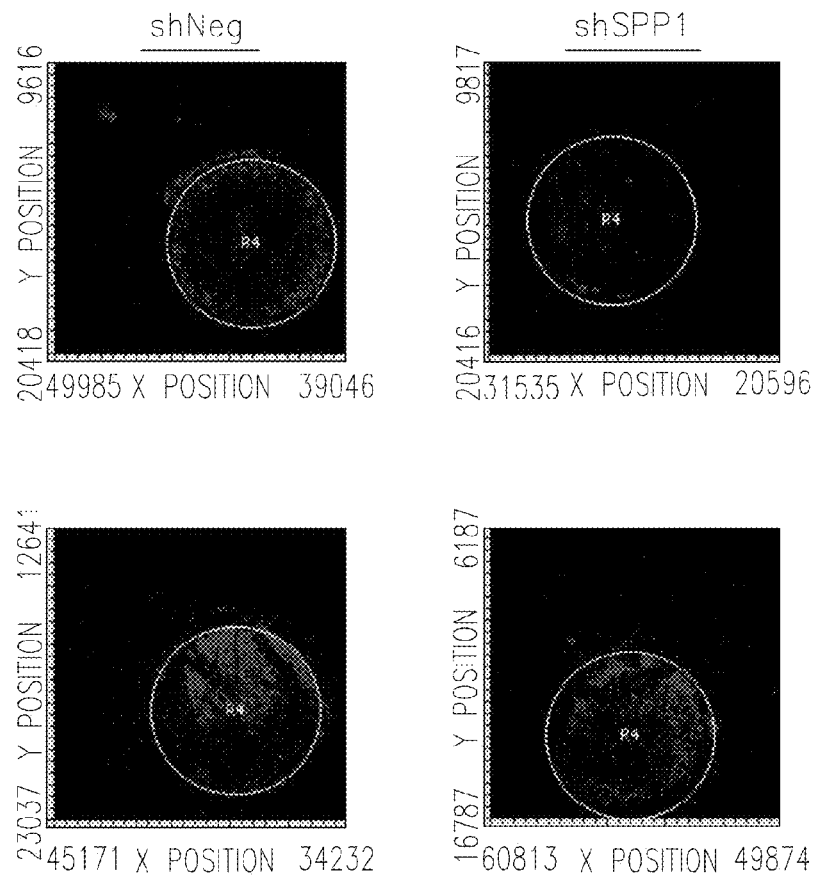
Figure 7E:
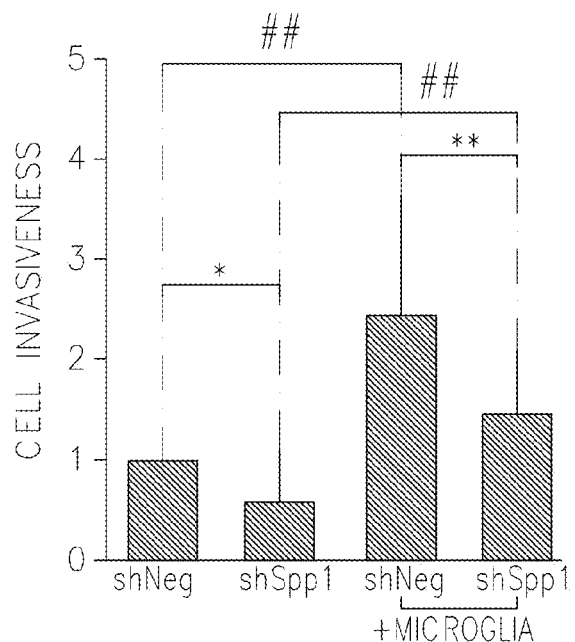

Silencing of Osteopontin in Microglia Cells Affects Acquisition of Alternative Phenotype and Impairs its Pro-Invasive Activity To investigate the role of identified proteins in GCM-induced activation of microglia cells, stable C6 glioma cell lines expressing shRNAs specific to osteopontin (shSPP1), or a control, negative shRNA (shNeg) were generated. Silencing efficiency was approximately 98.5% (FIGS. 7A and C). Silencing of lactadherin inhibited GCM-induced expression c-Myc and smad7 in microglia cells (FIG. 7B). Silencing of osteopontin inhibited GCM-induced expression arg-1 and smad7 in microglia cells (FIG. 7D). Furthermore, the number of glioma cells migrating through Matrigel filled inserts, as estimated by laser scanning cytometry, demonstrated that silencing of osteopontin in glioma cells strongly reduces microglia-dependent invasion (FIG. 7E).

Example 7

Osteopontin and Lactadherin Play Distinctive and Cooperative Roles in GCM Induced Activation of Microglia To determine if recombinant proteins could mimic action of glioma-conditioned medium on microglia cells, DNAs encoding two forms of osteopontin and lactadherin, were cloned and expressed in murine NIH3T3 fibroblasts. The expression of lactadherin and/or osteopontin in Amaxa-transfected fibroblasts was verified by qPCR (FIG. 8A). Efficacy of conditioned media (CM) from fibroblasts producing recombinant rat proteins to induce phagocytosis (FIG. 8B) or morphological transformation of microglia cells (FIG. 8C) was determined. CM from fibroblasts expressing osteopontin, but not control (GFP), stimulated microglia phagocytosis. CM from fibroblasts expressing osteopontin was also effective in inducing the amoeboid transformation of microglia cells.

Figure 9B:
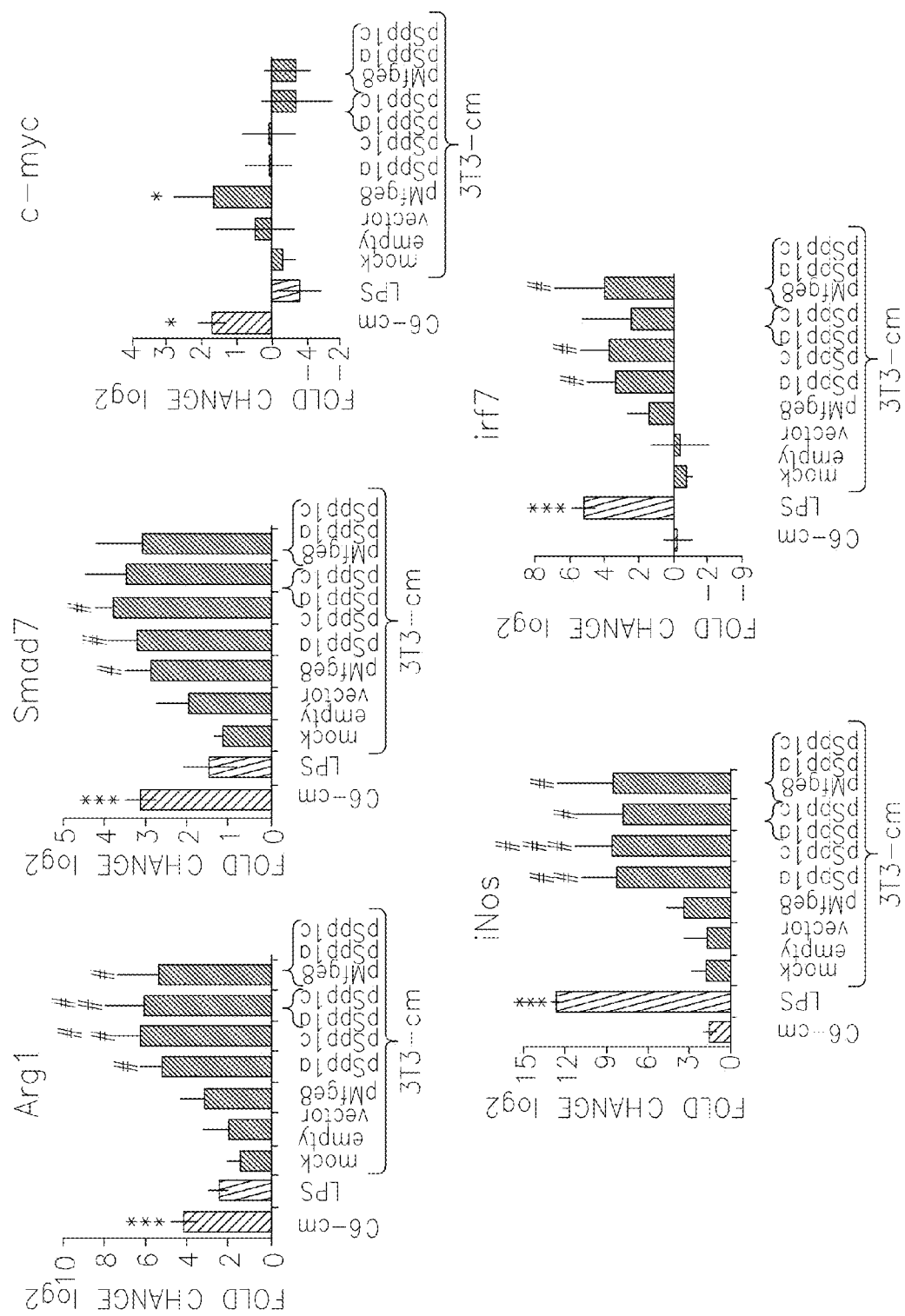

To evaluate whether recombinant proteins could mimic action of GCM on signalling and expression of selected genes characteristic for M2 or M1 phenotype in microglia cells, effects of conditioned media from fibroblasts producing recombinant rat proteins on microglia were tested; LPS and GCM were used as controls (FIG. 9). In contrast to GCM, CM from fibroblasts expressing both isoforms of osteopontin increased phosphorylation of IκB, STAT1, 3 and 5 to similar extent as LPS (FIG. 9A). CM from osteopontin producing fibroblasts increased the expression of arg-1 and smad7, but also inos and irf7, while lactadherin induced smad7 and c-myc expression (FIG. 9B).

Example 8

Figure 10A:
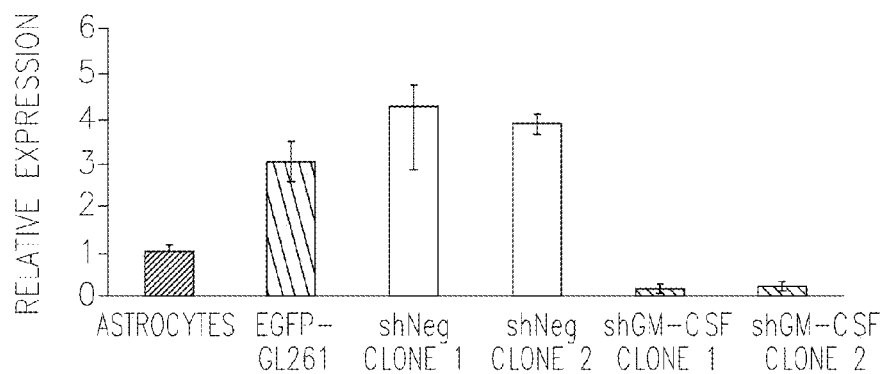
FIGS. 10A-10D show GM-CSF silencing in GL261 glioma cells and cell survival or proliferation: (A) Real time PCR of GM-CSF in glioma cells stably expressing GM-CSF specific shRNA as compared to non-transformed astrocytes; (B) Quantification of GM-CSF protein levels in glioma cells stably expressing GM-CSF specific shRNA as compared to non-transformed astrocytes; (C) BrdU incorporation assay of glioma cells stably expressing shGM-CSF; (D) MTT survival assay of glioma cells stably expressing shGM-CSF.
Figure 10B:
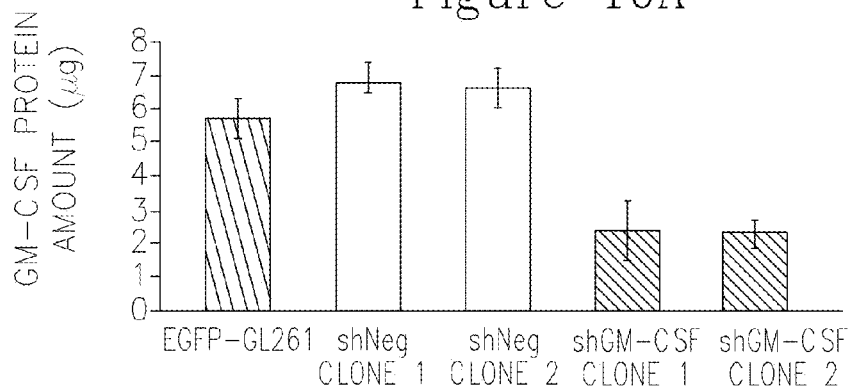
Figure 10C:
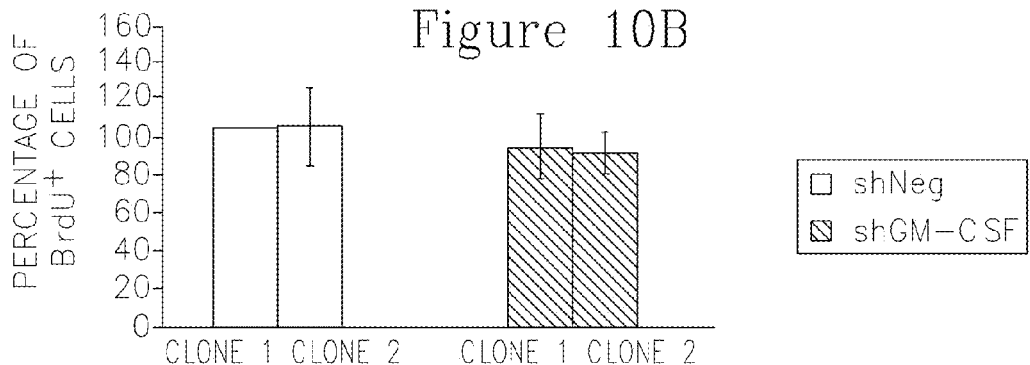
Figure 10D:
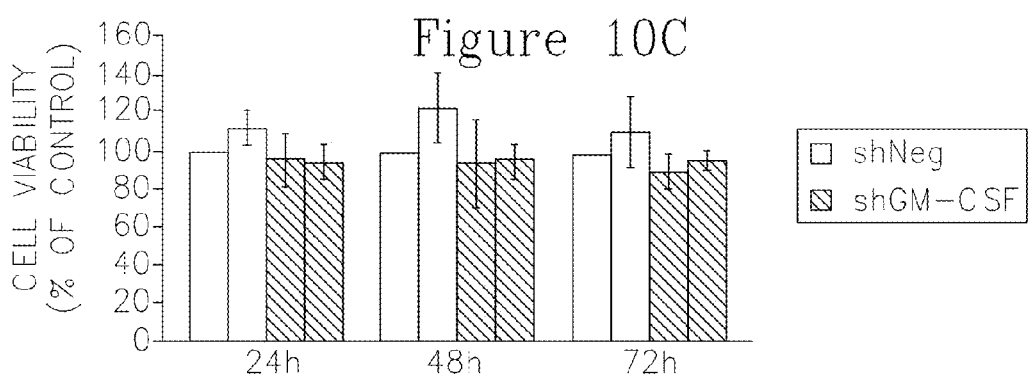

Glioma-Derived GM-CSF is Responsible for Recruitment of Microglia/Macrophages to Gliomas and Tumor Progression To check if glioma-derived GM-CSF is responsible for recruitment of microglia/macrophages to gliomas and for tumor growth, EGFP-GL261 glioma cells stably depleted of GM-CSF were generated by over-expressing plasmids encoding specific shRNA. Silencing of GM-CSF expression at the mRNA level (FIG. 10A) and at the protein level (FIG. 10B) in two independently derived clones was confirmed by qPCR and ELISA. Two clones derived in parallel and expressing negative shRNA served as controls. Silencing of GM-CSF expression in glioma cells did not affect their proliferation and survival, as demonstrated by BrdU incorporation and by MTT metabolism tests, respectively (FIGS. 10C and D).

Figure 11A:
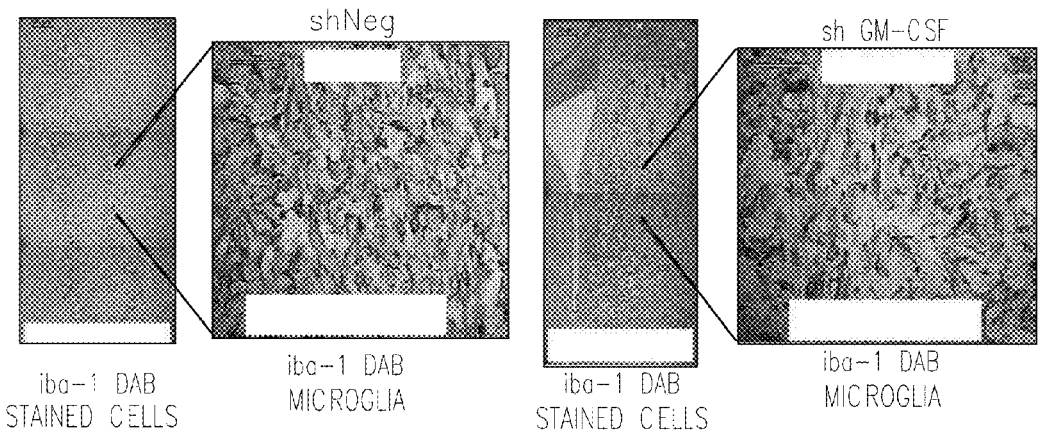
FIGS. 11A-11E show impaired recruitment of brain macrophages and reduced tumor size in GM-CSF depleted gliomas: (A) Microscopy analysis of anti-Iba-1 staining in microglia cells extracted from mice brains implanted with glioma cells stably expressing either shNeg or shGM-CSF, (B) Quantification of (A); (C) Staining of blood vessels with anti-vWF antibody mice implanted with GM-CSF depleted glioma cells as compared to controls. Tumor size analysis in GM-CSF depleted EGFP-GL261 glioma cells; (D) Quantification of tumor volume in mice implanted with GM-CSF depleted glioma cells; (E) Representative images of gliomas in mice implanted with control (shNeg) or GM-CSF depleted EGFP-GL261 glioma cells.
Figure 11B:
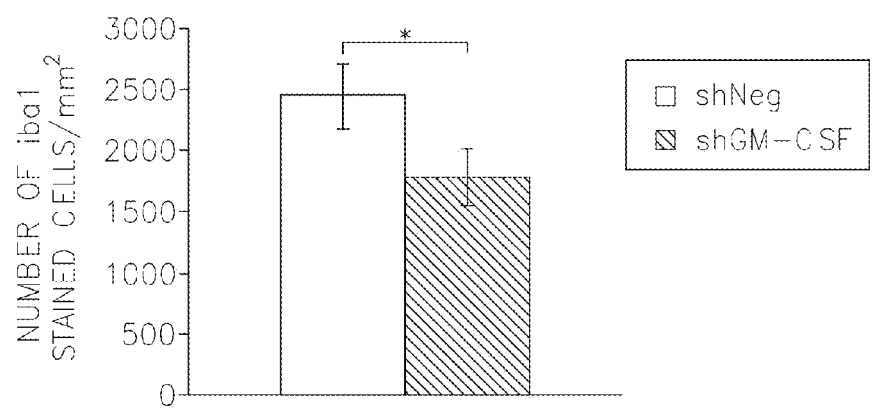
Figure 11C:
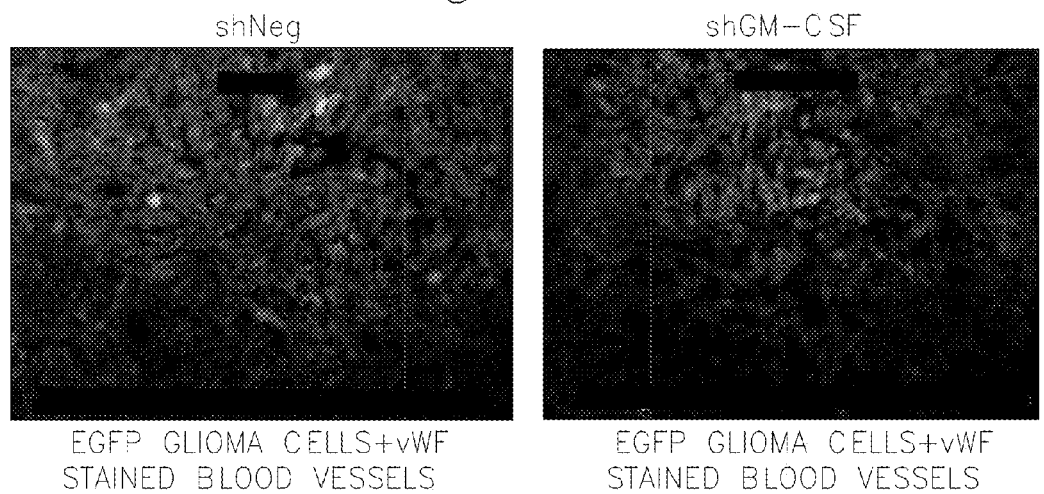
Figure 11D:
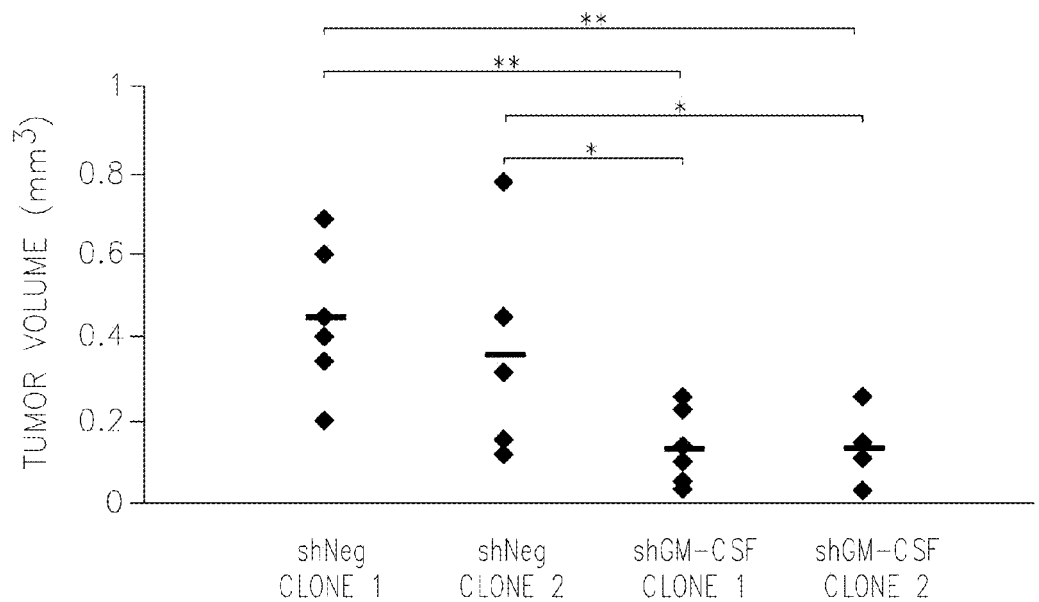
Figure 11E:
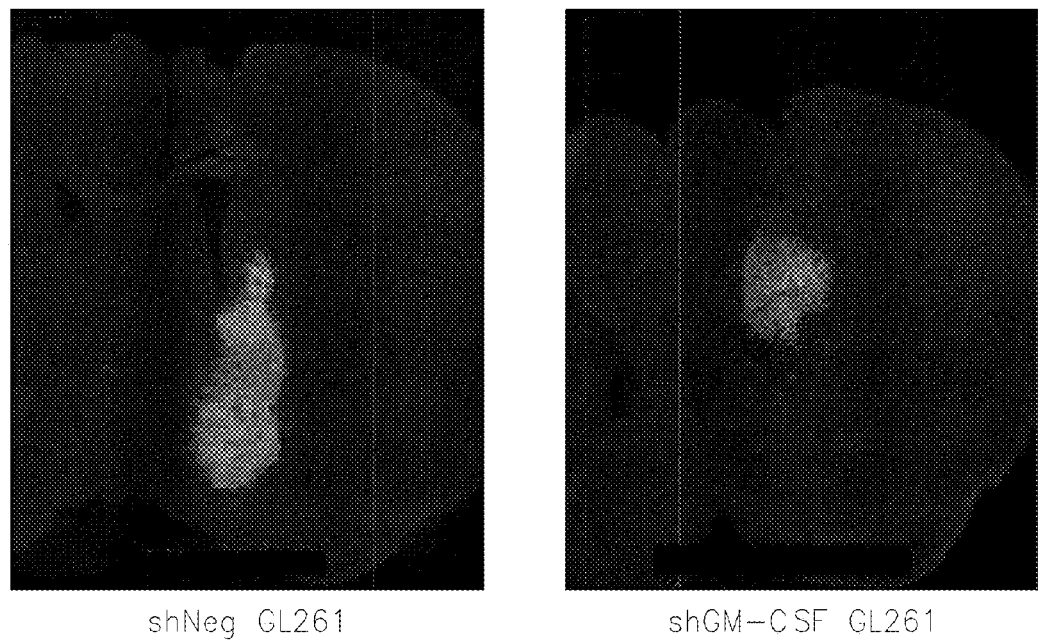

Two clones of EGFP-GL261 glioma cells expressing shNeg or shGM-CSF were implanted into the striatum of C57BL/6 mice. Staining with anti-Iba-1 antibody revealed a reduced number of microglia/macrophages in mice implanted with glioma cells depleted of GM-CSF as compared to control gliomas (shNeg) (FIGS. 11A and B). Staining of blood vessels with anti-vWF antibody revealed reduced formation of tumor vessels in mice implanted with GM-CSF depleted gliomas as compared to controls (FIG. 11C). Furthermore, a considerable reduction of tumor size (65%) was observed in brains of mice implanted with GM-CSF-depleted glioma cells as compared to mice implanted with shNeg glioma cells (FIG. 11D-E). Each dot represents an individual animal, the bold line represents the median of 6 mice in particular group; *p<0.05, **p<0.01.

These results demonstrate that GM-CSF is a major factor responsible for microglia/macrophage accumulation in gliomas as well as increased glioma invasion, and angiogenesis.

Example 9

Figure 12A:
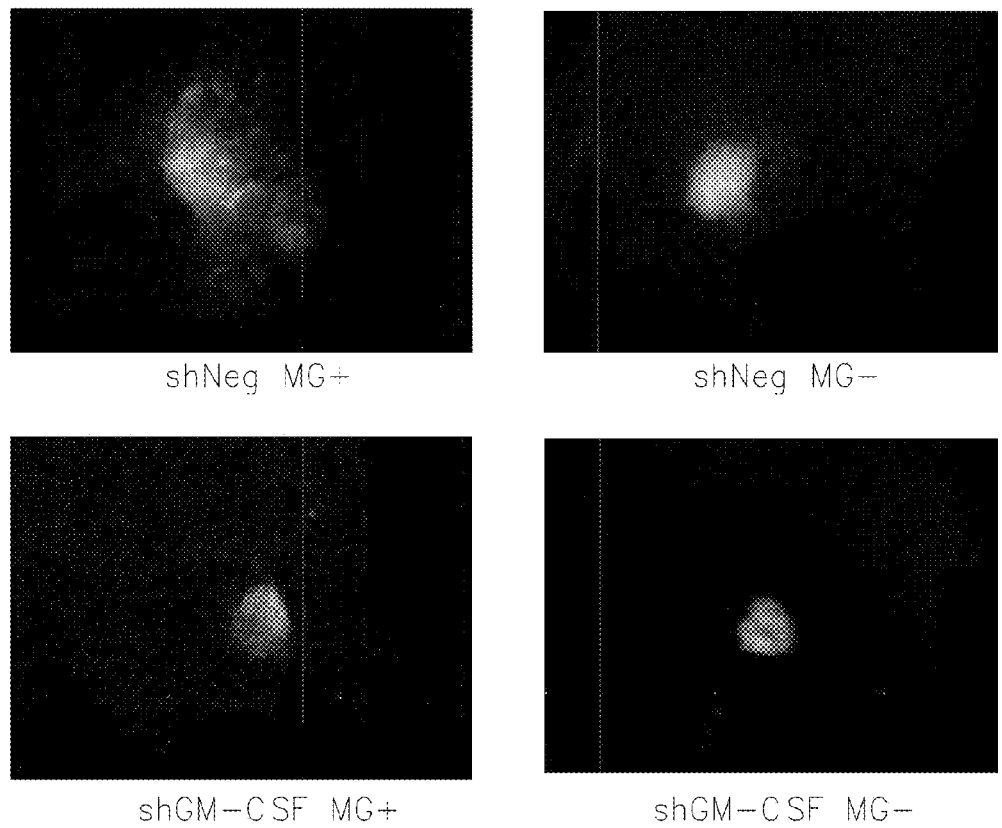
FIGS. 12A-12B show reduced invasiveness of GM-CSF depleted glioma cells in presence of microglia cells: (A) Invasion assay measuring tumor size by fluorescent area covered by EGFP-glioma cells in murine brain slice cultures injected with control or GM-CSF depleted EGFP-GL261 glioma cells in presence/absence of microglia cells; (B) Quantification of A.
Figure 12B:
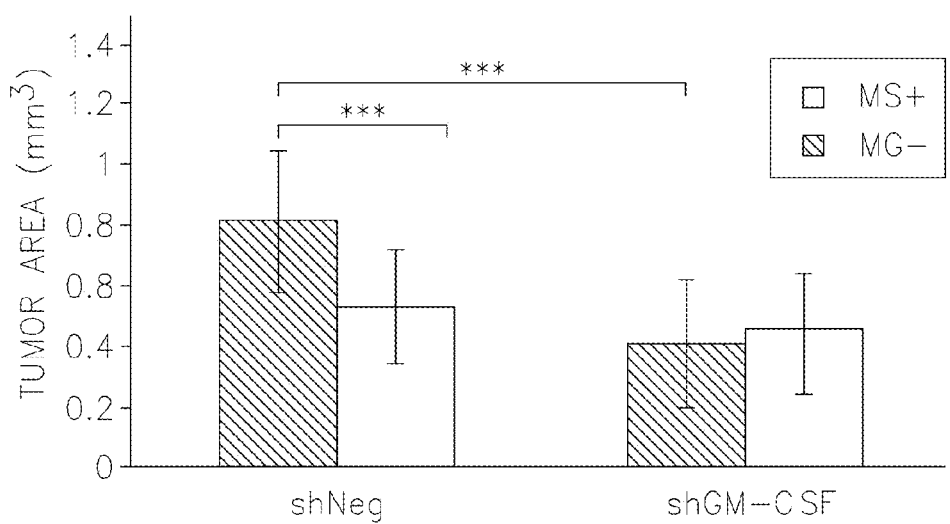

GM-CSF-Depleted Glioma Cells have Impaired Microglia-Dependent Glioma Invasion in Brain Organotypic Slice Cultures To investigate whether GM-CSF expression influences microglia dependent invasion or directly affects glioma invasion, an organotypic brain slice culture was used as a model. Control or GM-CSF-depleted EGFP-GL261 glioma cells were injected into murine brain slices and resulting tumor size was quantified 5d after injection by measuring the projected fluorescent area covered by the EGFP-glioma cells within the slice. The average tumor size was 58% (***p<0.001) smaller in brain slice cultures injected with GM-CSF-depleted EGFP-glioma cells as compared to controls (FIGS. 12A and B). In addition, depletion of microglia by pre-incubation with clodronate-filled liposomes led to reduced invasion of shNeg expressing glioma cells, but not of GM-CSF-depleted glioma cells (FIGS. 12A and B). Notably, microglia-dependent, long distance invasion of glioma cells into the brain parenchyma was strongly reduced in the absence of glioma-derived GM-CSF. This confirms that GM-CSF is responsible for microglia-dependent glioma invasion.

Example 10

Figure 13A:
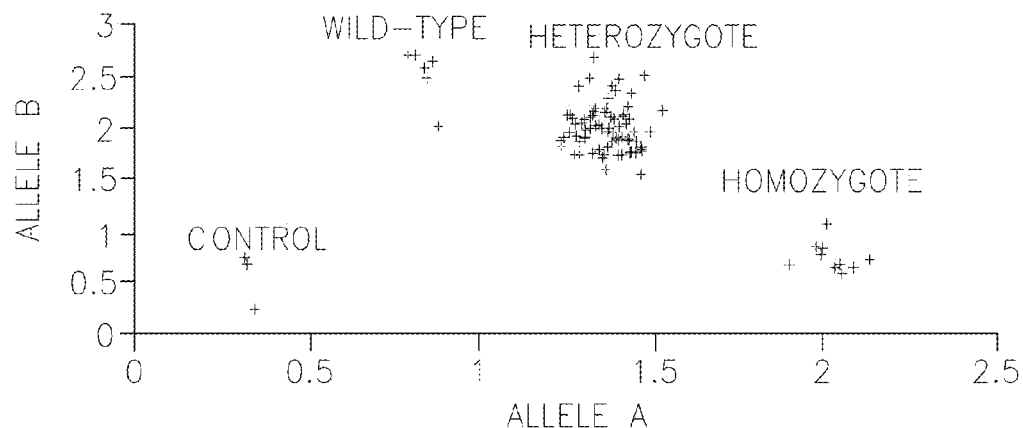
FIGS. 13A-13H show lack of accumulation of microglia/macrophage, lack of angiogenesis and tumor growth in M-CSF deficient, op/op mice: (A) Genotyping of B6C3Fe a/a-Csf1op/J mice by TaqMan Allelic Discrimination Method; (B) Flow cytometry analysis quantifying the percentage of microglia cells, macrophages and lymphocytes in brains of osteopetrotic op/op and wild-type (WT); (C) Flow cytometry analysis quantifying the percentage of monocytes, lymphocytes and granulocytes in the blood of op/op and WT mice; (D) Flow cytometry analysis quantifying the percentage of microglia cells, macrophages and lymphocytes in the brain of op/op and WT mice intracerebrally inoculated with GFP-expressing GL261 glioma cells; (E) Flow cytometry analysis quantifying the percentage of monocytes, lymphocytes and granulocytes in the blood of op/op and WT mice intracerebrally inoculated with GFP-expressing GL261 glioma cells; (F) Microscopy analysis of microglia cells of osteopetrotic and WT mice inoculated with EGFP-GL261 glioma cells; stained with anti-Iba-1 antibody and visualized with DAB; (G) Quantification of (F); (H) Tumor volume in osteopetrotic and WT mice inoculated with EGFP-GL261 glioma cells.
Figure 13B:
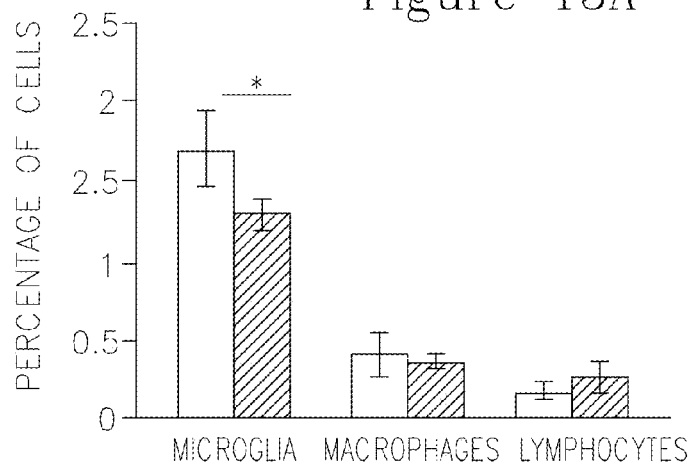
Figure 13C:
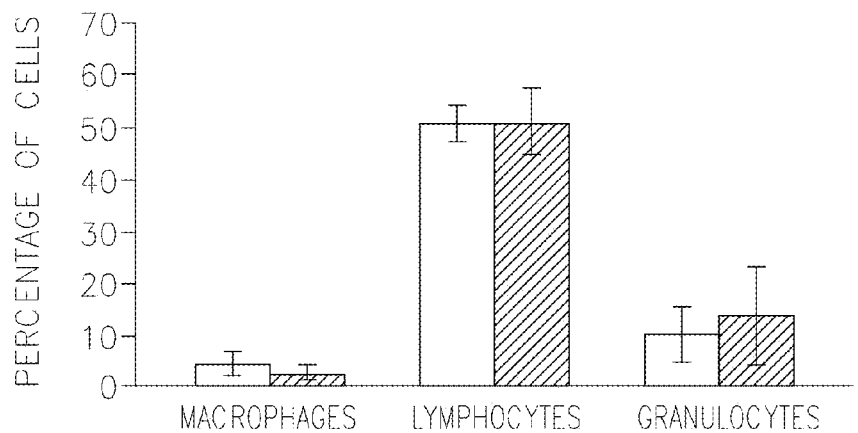

Macrophage Recruitment and Glioma Growth are not Affected in Osteopetrotic Op/Op Mice Osteopetrotic op/op mice have a recessive null mutation in the m-csf/csf1 gene resulting in deficiency of M-CSF production and monocytes/macrophages deficits. The homozygote mutant op/op, heterozygote and wild-type (WT) mice were identified by genotyping with the TaqMan Allelic Discrimination Method (FIG. 13A). Immunomagnetic separation of CD11b+ cells from tumor tissues followed by flow cytometry permitted distinction of the two populations: microglia (CD11b$^+$/CD45$^{low}$) and blood-derived macrophages (CD11b$^+$/CD45$^{high}$). Reduction in the number of CD11b$^+$ microglia and macrophages in the brain of op/op (Grey bars) as opposed to WT mice (white bars) was confirmed (FIG. 13B), whereas the number of monocytes in the blood of op/op mice (grey bars) was unchanged (FIG. 13C).

Figure 13D:
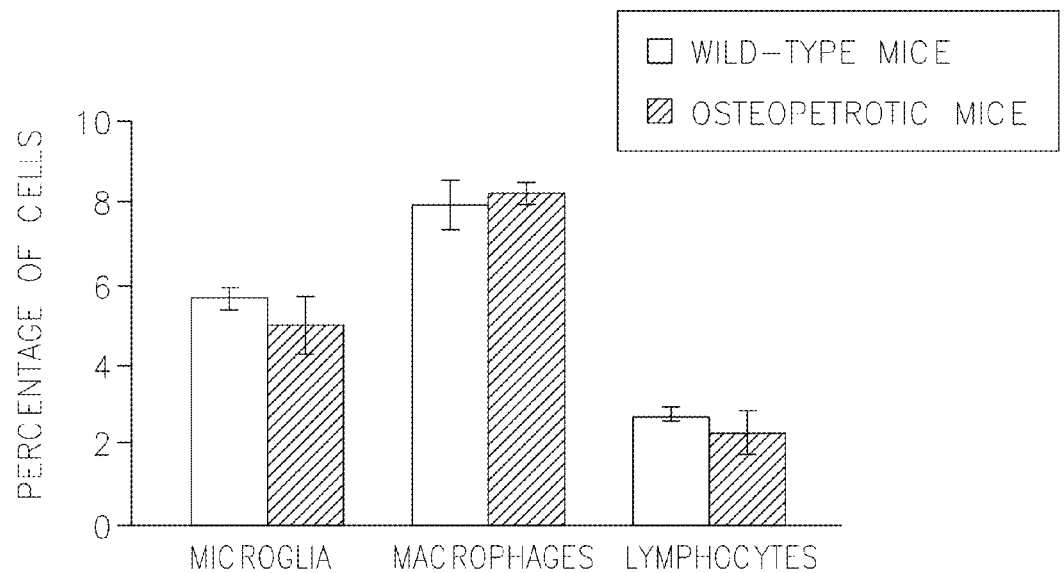
Figure 13E:
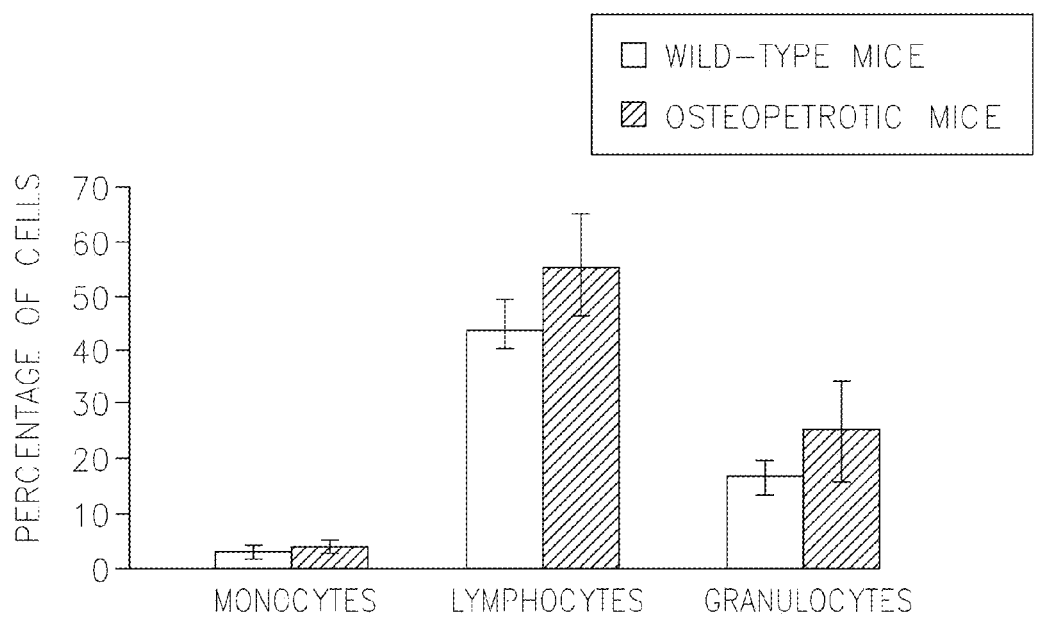
Figure 13F:
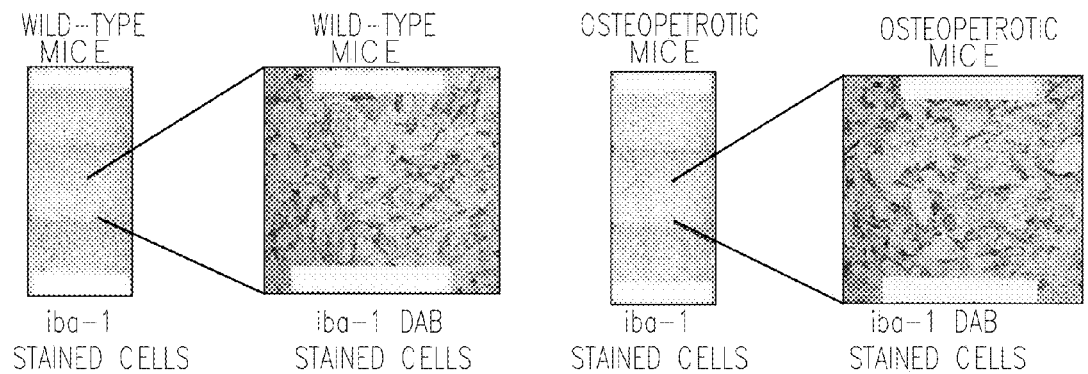
Figure 13G:
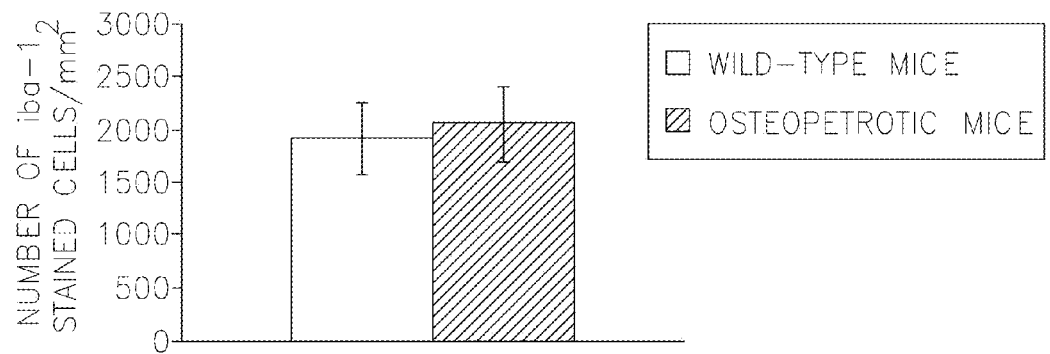

To determine the role of M-CSF in microglia/macrophage recruitment and glioma progression, osteopetrotic mice were implanted with syngenic EGFP-GL261 glioma cells. Flow cytometry analysis did not show any difference in the percentage of glioma infiltrating CD11b$^+$CD45$^{low}$ microglia and CD11b$^+$CD45$^{high}$ macrophages in the brains of wild-type and op/op mice (grey bars) (FIG. 13D). The percentage of peripheral blood monocytes in op/op and wild-type mice bearing glioma was similar, and the percentage of granulocytes increased similarly in both mice strains (FIG. 13E). Staining with anti-Iba1 antibody used to detect microglia/ macrophages in tumor-bearing brains, evidenced similar accumulation and morphology of glioma-infiltrating Iba1 positive cells in wild type and op/op mice. Most Iba1 positive cells acquired amoeboid morphology of activated macrophages in glioma-bearing op/op mice (FIGS. 13F and G).

Figure 13H:
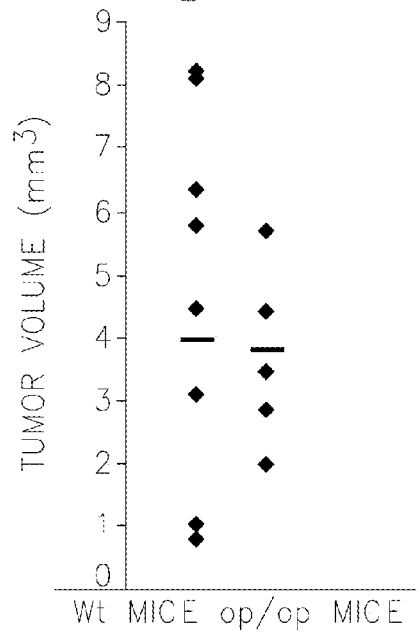

Staining of blood vessels with anti-vWF (von Willebrand factor) antibody on sections from glioma-bearing brains showed similar formation of a tumor vessel network in the CSF-1 null mice as compared to WT controls (data not shown). Quantification of tumor volumes showed no difference in tumor size between op/op and wild-type mice (FIG. 13H). These results demonstrate that despite the reduced number of microglia/macrophages in naive op/op mice, tumor implantation induces similar infiltration of microglia/ macrophages, vessel density and tumor progression suggesting that CSF-1 is not the cytokine responsible for accumulation of microglia/macrophages in gliomas.

Example 11

Figure 14A:
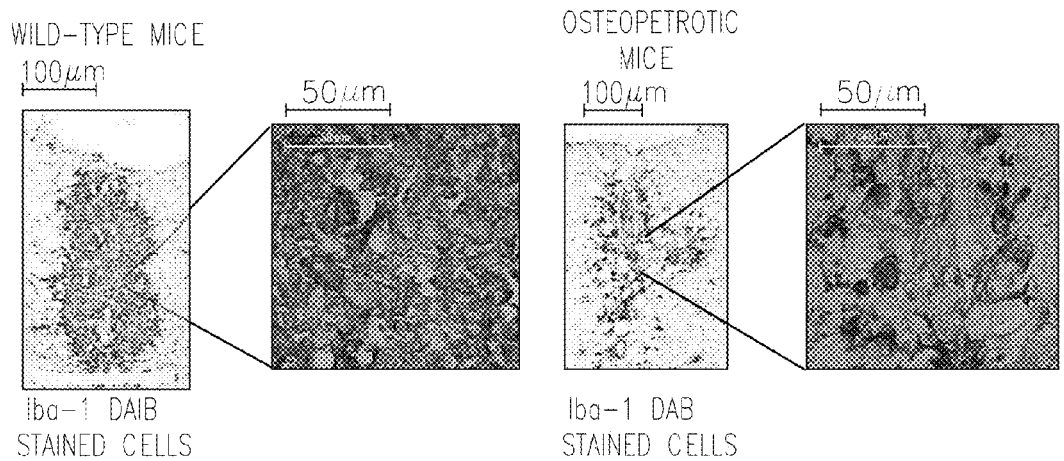
FIGS. 14A-14B show reduction of accumulated microglia/macrophages in spinal cord focal demyelinating lesions of osteopetrotic op/op mice: (A) Microscopy analysis of microglia/macrophages stained with anti-Iba-1 antibody and visualized with DAB in WT and op/op mice with spinal cord lesions; (B) Quantification of (A).
Figure 14B:
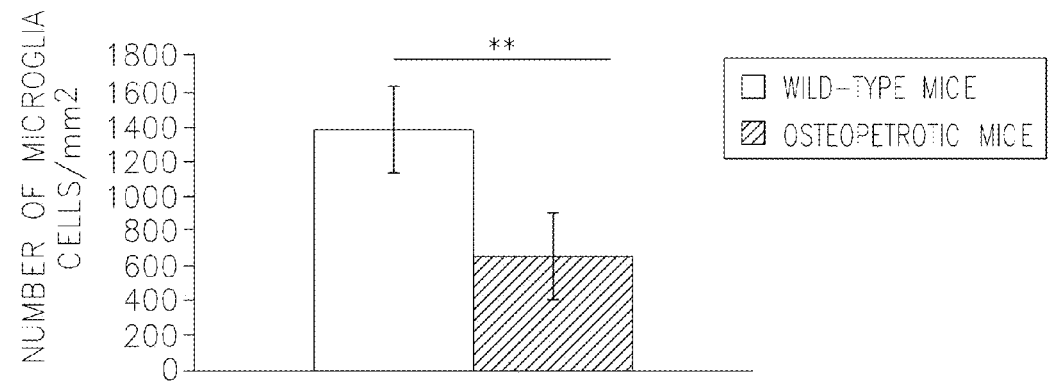

Reduced Accumulation of Microglia/Macrophages in the Spinal Cord Demyelinating Lesion of M-CSF Deficient Mice To determine whether M-CSF deficiency generally affects infiltration of microglia/macrophages, the response to spinal cord damage in wild type and op/op mice was examined. A focal demyelinating lesion in the spinal cord white matter was induced and the number and morphology of microglia/ macrophages in op/op mice and wild type controls after 10 days was investigated. A significant reduction in the number of Iba-1 positive cells within the lesion of op/op mice as compared to wild-type control was observed (676±94 cells/ mm$^2$ in op/op vs. 1389±129 cells/mm$^2$ in WT; p<0.001) (FIGS. 14 A and B).

Example 12

Figure 15A:
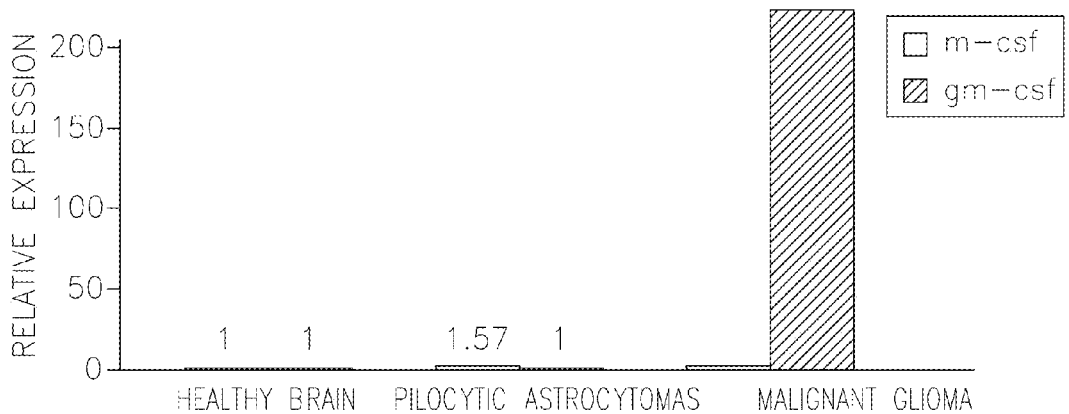
FIGS. 15A-15B show correlation between CSF-2 expression, high tumor grade and poor patient survival: (A) Quantitative analysis of CSF-1 and CSF-2 expression in human glioma biopsies; (B). Kaplan-Meier survival plot of patients with CSF-2 up- and down-regulation respectively.
Figure 15B:
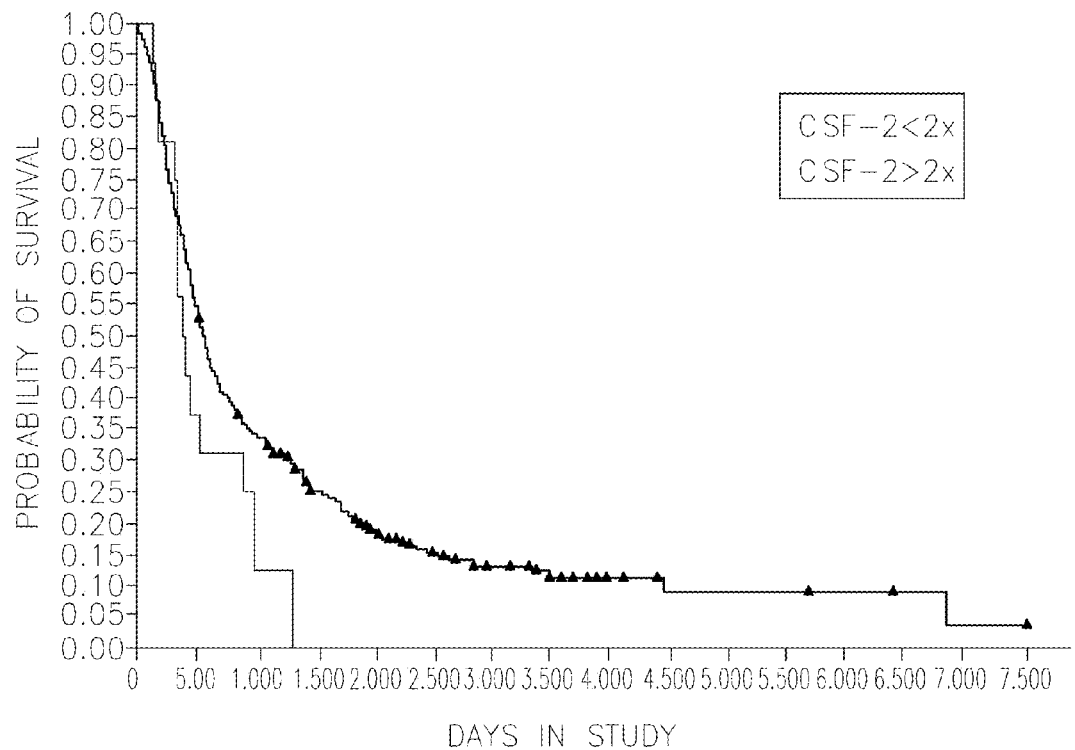

CSF-2 is Highly Expressed in GBM but not Low Grade Gliomas or in Normal Cortex and Shows Correlation with Patient Survival In order to relate in vitro findings to actual human patient tumor specimens, CSF-1 and CSF2 expression in GBM, healthy brain, and lower grade gliomas was evaluated by quantitative PCR. FIG. 15A shows highly up-regulated expression of CSF-2 but not CSF-1 in glioblastoma multiforme (GBM, WHO grade IV) biopsies as compared to low grade pilocytic gliomas (WHO grade 1) and normal brain. A Kaplan-Meier survival curve based on differential CSF-1 and CSF-2 expression among 343 glioma patients whose data is publicly available in the NCI Repository for Molecular Brain Neoplasia Data (REMBRANDT) was generated (FIG. 15B). Up- and down-regulation were defined as a two-fold increase or decrease in CSF-1/CSF-2 expression, compared to the mean expression level within the data set. Based on these criteria, CSF-2 was up-regulated in 16 and down-regulated in 22 of all glioma patients. Survival time of patients with decreased CSF-2 expression was improved as compared to the worse prognosis observed in patients with CSF-2 up-regulation. Such correlation was not observed for CSF-1 expression. Statistical significance was reached when comparing survival in these two extreme patient populations (p=0.0217).

Example 13

Inhibition of GM-CSF Prolongs Life of Animal with Gliomas

Mice were randomly assigned to receive intracranial implantation of shNeg or shRNA glioma cells and observed until becoming moribund. EGFP-GL261 glioma cells, shGM-CSF glioma cells or shNeg glioma cells were inoculated in a right striatum using a syringe with a 26-gauge needle in a stereotactic apparatus according to the coordinates (+1.5 mm AP, −1.5 mL). Mice were resuscitated using i.p. administration of atipamazole and treated with the Tolfedine 4% (4 mg/kg s.c.) analgesic. Kaplan-Meier analysis of mice implanted with shGM-CSF and shNeg glioma cells (n=10 mice per group) was performed.

Figure 16:
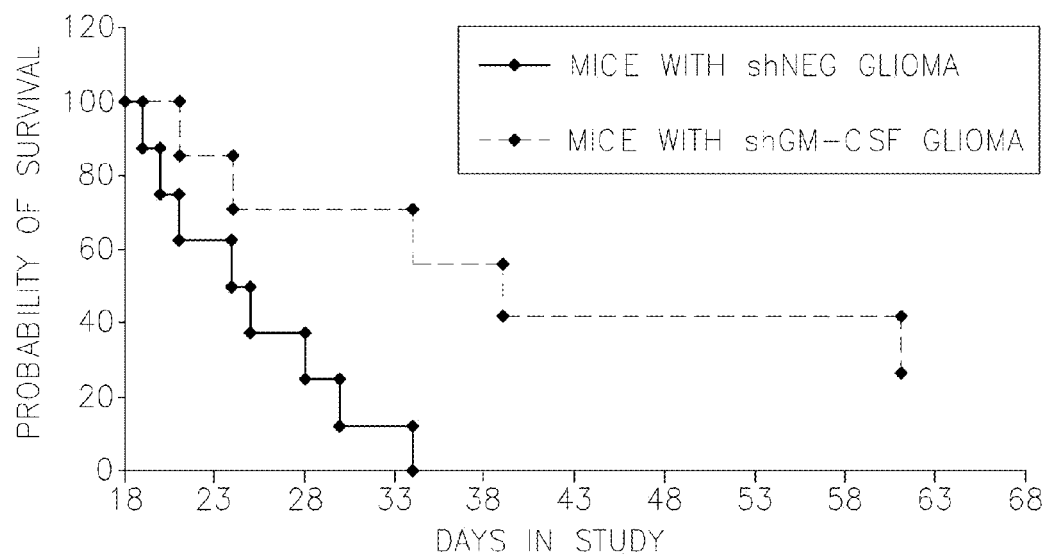
FIG. 16 shows survival curves for mice with intracranial gliomas expressing control or GM-CSF specific shRNA.

Survival curves for mice with intracranial gliomas expressing control or GMC-SF specific shRNA showed a significant survival benefit for mice implanted with GM-CSF depleted gliomas (FIG. 16). Two mice having shGM-CSF-gliomas were alive 63 days post implantation.

Example 14

Inhibiting Peptides of OPN, GM-CSF and GM-CSFR Attenuate Expression of Markers of Alternative Microglia Activation (M2 Phenotype)

U87-MG human glioma cells were plated on 100 mm culture dishes in a total volume of 8 mL culture medium for 24 h. Subsequently, medium was conditioned by glioma cells (GCM, glioma-conditioned medium) for another 24 h. After conditioning, medium was collected and centrifuged at 1000×g for 5 min at room temperature. 500 μL medium was supplemented with selected peptides to a final concentration of 500 μM, and microglia cells were treated with GCM supplemented with peptides for 6 h. Cells were lysed, total RNA was isolated and cDNA was synthesized using reverse-transcriptase and random hexamer primers. The following inhibiting peptides were used.

| | | |
|---|---|---|
| GMCSF1 | QPWEHVNAIQEARRLLNLSR | (SEQ ID NO: 3) |
| GMCSF2 | KDFLLVIPFDCWEPVQE | (SEQ ID NO: 4) |
| GMCSFR1 | FQYQLDVHRKN | (SEQ ID NO: 5) |
| GMCSFR2 | ADVRILN | (SEQ ID NO: 6) |
| OPN | DGRGDSV | (SEQ ID NO: 7) |
| MFGE8 | EVRGDVF | (SEQ ID NO: 8) |
| MFGE8rat | TQRGDIF | (SEQ ID NO: 18) |

The expression level of genes that were previously identified as markers of the M2 microglia/macrophage phenotype (see FIG. 4.) such as: Arg1, Id1, c-Myc and MMP-14 was determined using Real-Time PCR. Likewise, the expression level of iNOS was determined to evaluate induction of an immune response. The expression level of all genes tested was normalized to their expression level in control, microglia-conditioned medium treated (MGCM) cells.

The line on the charts represents a threshold for the gene expression level in control cells (CTRL1) treated with a control peptide DQIGFRT (SEQ ID NO: 43).

Figure 17A:
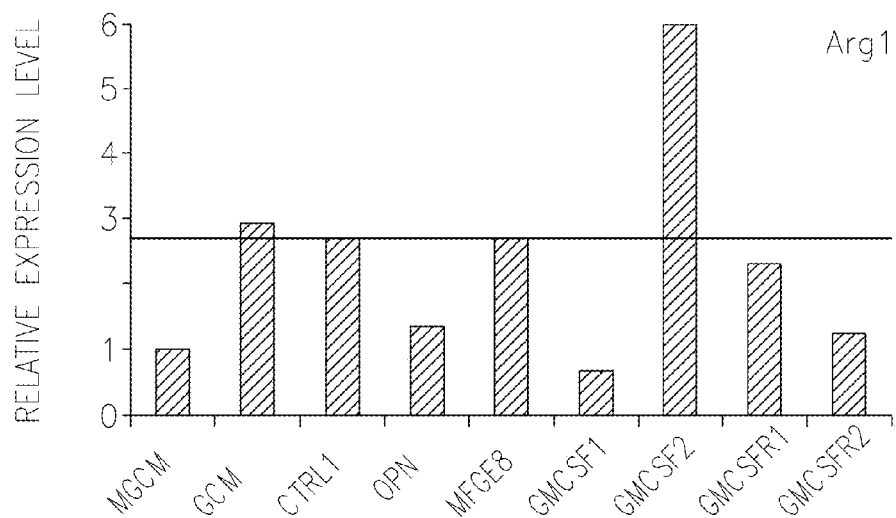
FIGS. 17A-17F show attenuated expression of alternative microglia activation markers in human glioma cells incubated with mouse microglia cells treated with peptide inhibitors of OPN, GM-CSF and GM-CSFR: (A) Real time PCR of Arg1 in U87-MG human glioma cells cultured in GCM supplemented with the indicated peptides; (B) and (C) Real time PCR of Id1 in U87-MG human glioma cells cultured in GCM supplemented with the indicated peptides; (D) Real time PCR of c-Myc in U87-MG human glioma cells cultured in GCM supplemented with the indicated peptides; (E) Real time PCR of MMP-14 in U87-MG human glioma cells cultured in GCM supplemented with the indicated peptides; (F) Real time PCR of iNOS in U87-MG human glioma cells cultured in GCM supplemented with the indicated peptides.
Figure 17B:
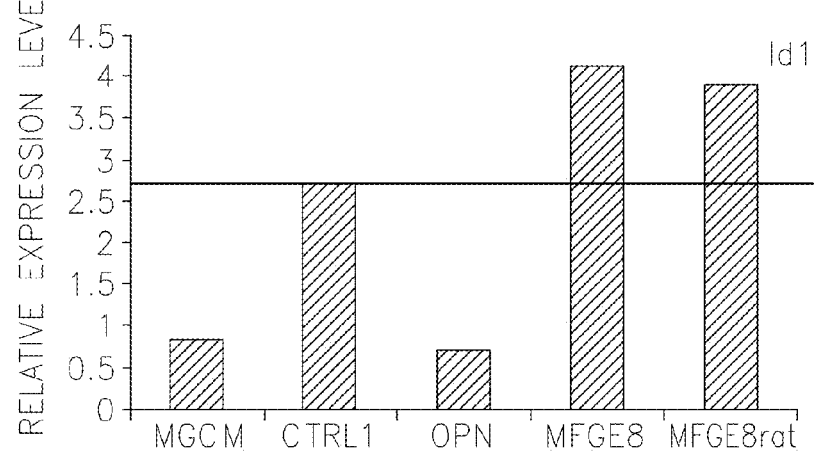
Figure 17C:
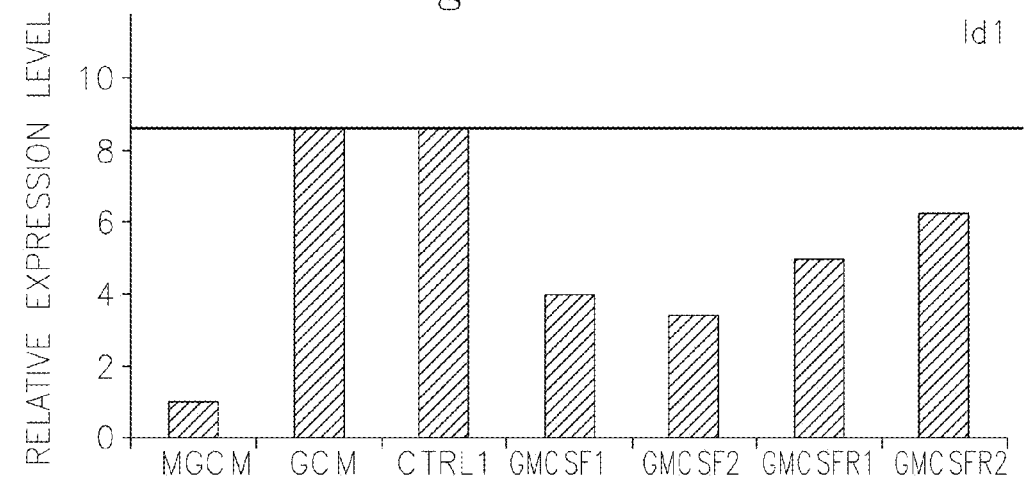
Figure 17D:
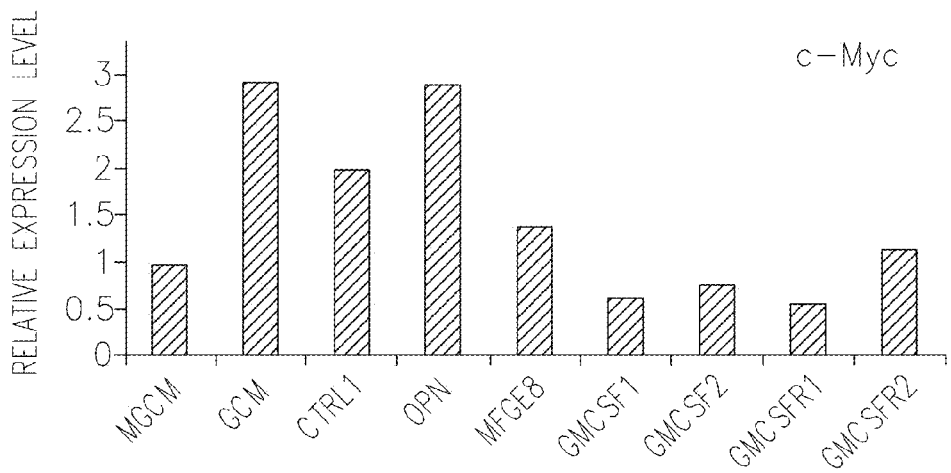
Figure 17E:
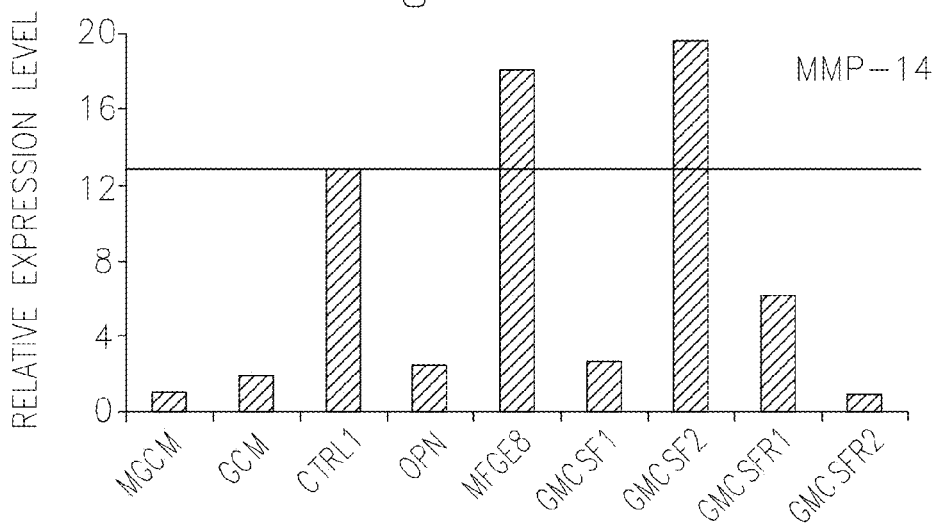
Figure 17F:
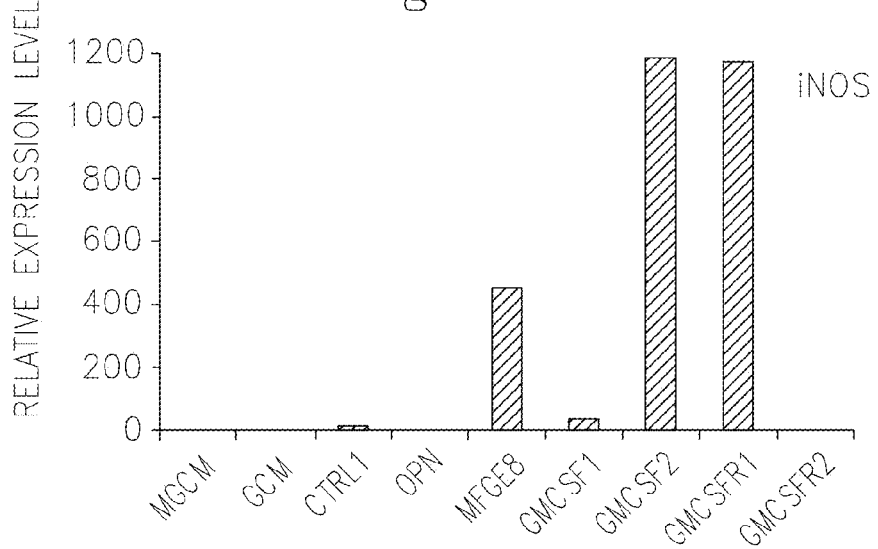

As seen in FIG. 17A-B, the OPN inhibiting peptide (SEQ ID NO: 7) down-regulated the most relevant markers of M2 phenotype in microglia cells—Arg1 and Id1. Likewise inhibitors of both GM-CSF and GM-CSFR down-regulated markers of the M2 phenotype such as Arg1, Id1, c-Myc and MMP14 in microglia cells (FIG. 17 A, C-E). Surprisingly, peptides inhibiting GM-CSF and GM-CSFR were also able to induce the expression of the pro-inflammatory gene iNOS (FIG. 17F).

Example 15

Inhibiting Peptides of OPN, GM-CSF and GM-CSFR Attenuate Invasiveness of U87-MG Human Glioma Cells BV2 immortalized mouse microglia cells were plated on 24-well culture dish in a total volume of 0.7 mL culture medium for 24 h. Culture medium was subsequently replaced with 0.7 mL of a fresh medium (2% FBS, DMEM with Glutamax, PenStrep) supplemented with peptides at a final concentration of 500 μM for 1 h. U87-MG human glioma cells were seeded on Matrigel-coated inserts. 18 hours later the Matrigel was removed from the inserts and cells were fixed with 10% methanol and stained with DAPI. The number of cells that migrated through the Matrigel (invasive cells) was calculated using a fluorescent microscope. U87-MG co-cultured with BV2 cells, (NULL+BV2) served as a positive control of invasiveness; and U87-MG alone (NULL) served as a negative control of invasiveness.

Statistical analysis was performed using analysis of variance (ANOVA: single factor). "P-values" define probability, that the observed results were random events.

The line on the charts represents a threshold for invasiveness of untreated cells co-cultured with BV2/microglia cells (NULL+BV2).

Figure 18:
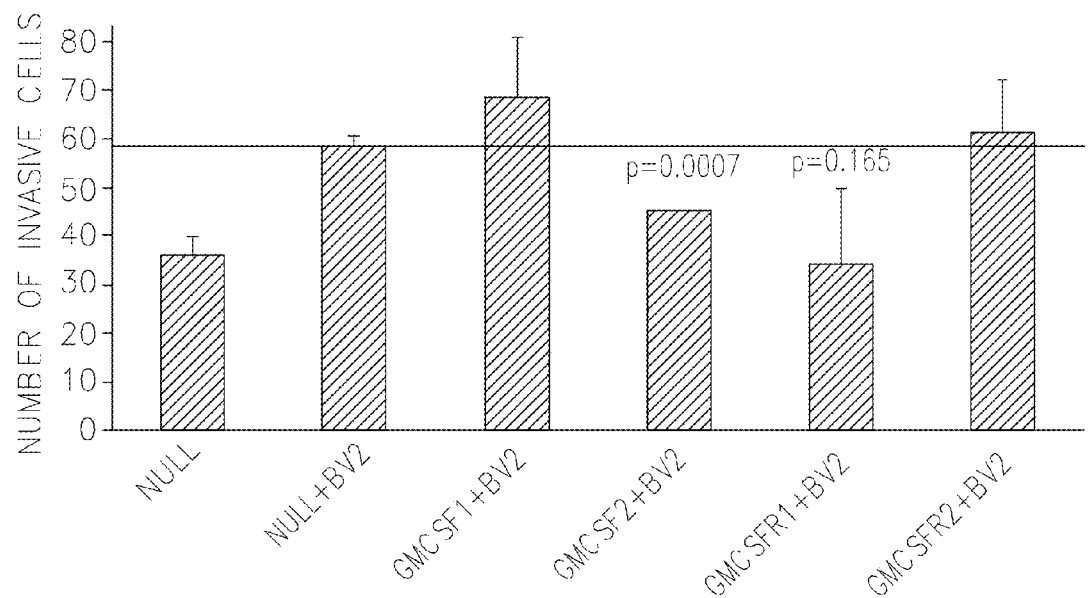
FIG. 18 shows matrigel matrix invasion assay of glioma cells in the presence or absence of microglia cells treated with GM-CSF/GM-CSFR peptide inhibitors.

As seen in FIG. 18, GMCSF and GMCSFR peptides were able to attenuate the invasiveness of glioma cells in the presence of microglia cells.

Example 16

Figures 19A, 19B:
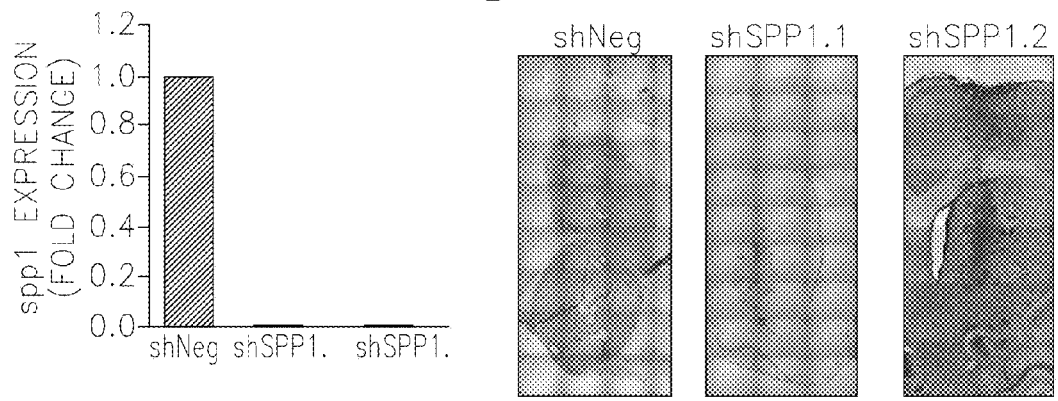
FIGS. 19A-19C show attenuated tumor growth in an in vivo rat glioma model with RNAi mediated permanent silencing of osteopontin: (A) Quantitative PCR of osteopontin (spp1) in rat C6 glioma clones with RNAi mediated permanent silencing of osteopontin; (B) Representative images of tumors 15 days after implantation of C6 glioma into Wistar rats expressing control shRNA (shNeg) or osteopontin shRNA (shSPP1); (C) Tumor volume 15 days after implantation of C6 glioma expressing control shRNA (shNeg) or osteopontin shRNA (shSPP1).
Figure 19C:
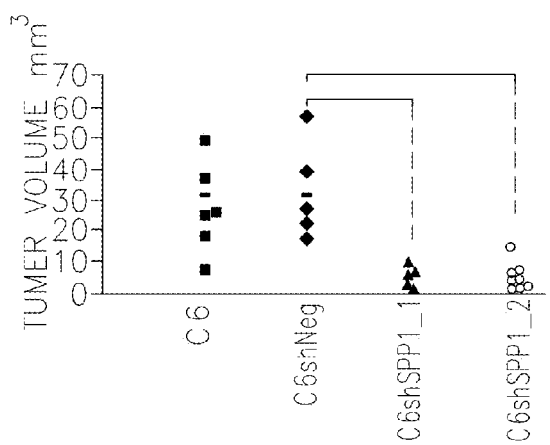

RNAi Mediated Permanent Silencing of Osteopontin Attenuates Tumor Growth in Rat Glioma Model In Vivo RNA was isolated from rat C6 glioma clones stably expressing shRNA against osteopontin cells and cDNA was synthesized using reverse-transcriptase and random hexamer primers. Knock down efficiency of osteopontin was confirmed by Real Time PCR (FIG. 19A). C6 glioma cells expressing control shRNA (shNeg) or glioma cells depleted of osteopontin (shSPP1) (5×10$^4$ cells/2.5 μl of DMEM) were implanted into the right striatum of 8-10 weeks old Wistar rats. 15 days after glioma implantation, the animals were sacrificed and intracardially perfused with 4% paraformaldehyde. The brains were removed, frozen with dry $CO^2$ and serial 20- or 12-μm-thick coronal sections were collected using a cryostat. To quantify the tumor size, 20 μm-thick sections were stained with toluidine blue, images were acquired using a Leica DM4000B microscope. Tumor areas were measured using ImageJ software in an every fourth brain slice and tumor volumes were calculated according to the Cavalieri principle (Gabrusiewicz et al, 2011). Representative photomicrographs of toluidine blue-stained sections of rat brains show that animals implanted with C6-shSPP1 cells developed significantly smaller tumors compared to animals implanted with C6-shNeg cells (FIG. 19B). Moreover, gliomas from implanted C6-Neg were of similar sizes as WT C6 cells (n=5, 28.33±14.53 mm$^3$). Quantification of tumor volumes showed an 88% reduction in tumor volumes of osteopontin depleted gliomas (mean values for C6-Neg=34.02 mm$^3$, C6-shSSP1=6.03 mm$^3$) (FIG. 19C). Results are expressed as the means±s.d. from 2 independent experiments (U-Mann-Whitney test).

These data show that glioma-derived osteopontin contribute to glioma growth in vivo.

Example 17

Figure 20:
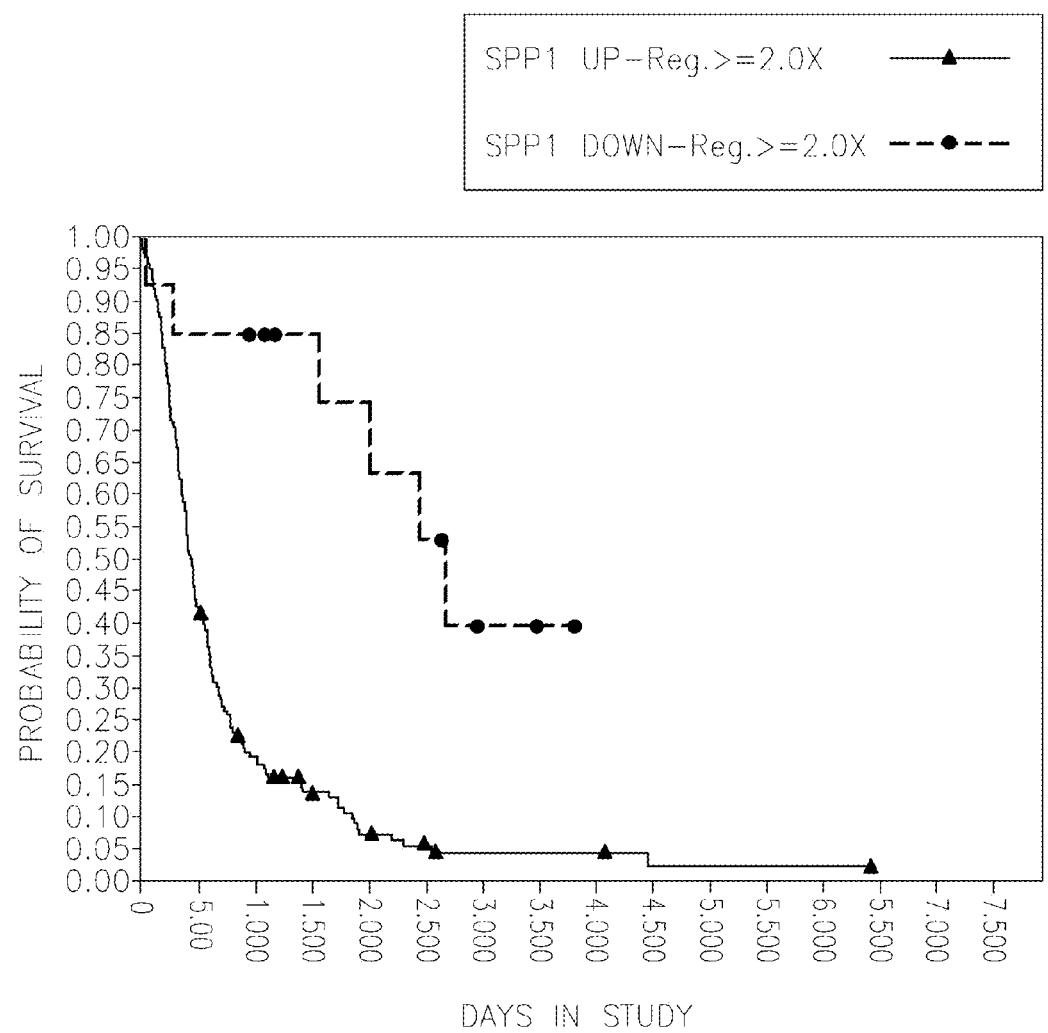
FIG. 20 shows a correlation between OPN over-expression and poor patient survival. Kaplan-Meier survival plot for patients with differential osteopontin (SPP1) expression.

OPN Expression Correlates with Poor Survival of Patients Suffering from Grade II-IV Gliomas A Kaplan-Meier survival curve based on differential SPP1 expression among 343 glioma patients whose data is publicly available in the NCI Repository for Molecular Brain Neoplasia Data (REMBRANDT) was generated. The curve illustrates a negative correlation between osteopontin expression and predicted survival time for patients with ≥2-fold up-regulated osteopontin expression (SPP1), n=162, (worse prognosis) vs. patients with ≥2-fold down-regulated osteopontin expression (SPP1), n=13, (better prognosis) (FIG. 20).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

What is claimed is:

1. An isolated peptide for inhibiting GM-CSF activity, wherein said peptide consists of the amino acid sequence SEQ ID NO: 5; and wherein the isolated peptide is fused to a peptide assisting transport through the blood brain barrier (BBB).

2. The isolated peptide of claim 1, wherein said peptide is a cyclic peptide.

3. A pharmaceutical composition comprising the isolated peptide of claim 1 and a pharmaceutical acceptable carrier.

4. The pharmaceutical composition of claim 3, wherein said pharmaceutical acceptable carrier is selected from the group consisting of: an aqueous solution, vegetable oil, alcohol, polyethylene glycol, propylene glycol or glycerin.

5. The isolated peptide of claim 1, wherein said peptide assisting transport through the BBB is a molecular Trojan horse (MTH).

* * * * *